(12) United States Patent
Shinohata et al.

(10) Patent No.: US 8,293,934 B2
(45) Date of Patent: Oct. 23, 2012

(54) ISOCYANATES AND AROMATIC HYDROXY COMPOUNDS

(75) Inventors: Masaaki Shinohata, Tokyo (JP); Nobuhisa Miyake, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 13/150,318

(22) Filed: Jun. 1, 2011

(65) Prior Publication Data

US 2011/0319648 A1 Dec. 29, 2011

Related U.S. Application Data

(62) Division of application No. 12/743,767, filed as application No. PCT/JP2008/070765 on Nov. 14, 2008, now Pat. No. 7,977,504.

(30) Foreign Application Priority Data

| Nov. 19, 2007 | (JP) | 2007-299497 |
| Nov. 19, 2007 | (JP) | 2007-299504 |
| Nov. 19, 2007 | (JP) | 2007-299703 |

(51) Int. Cl.
*C07C 261/00* (2006.01)
*C07C 269/00* (2006.01)
*C07C 271/00* (2006.01)

(52) U.S. Cl. ...................................................... 560/25
(58) Field of Classification Search .................. None
See application file for complete search history.

(56) References Cited

U.S. PATENT DOCUMENTS

| 2,692,275 A | 10/1954 | Bortnick |
| 3,734,941 A | 5/1973 | Sydor |
| 3,992,430 A | 11/1976 | Bacskai |
| 4,081,472 A | 3/1978 | Tsumura et al. |
| 4,097,676 A | 6/1978 | Romano |
| 4,290,970 A | 9/1981 | Merger et al. |
| 4,386,033 A | 5/1983 | Konig et al. |
| 4,388,246 A | 6/1983 | Sundermann et al. |
| 4,388,426 A | 6/1983 | Schure et al. |
| 4,482,499 A | 11/1984 | Merger et al. |
| 4,613,466 A | 9/1986 | Merger et al. |
| 4,659,845 A | 4/1987 | Rivetti et al. |
| 4,692,550 A | 9/1987 | Engbert et al. |
| 5,364,957 A | 11/1994 | Arnoldy et al. |
| 5,386,053 A | 1/1995 | Otterbach et al. |
| 5,391,802 A | 2/1995 | Buysch et al. |
| 5,773,643 A | 6/1998 | Yagii et al. |
| 6,034,265 A | 3/2000 | Bosetti et al. |
| 2003/0125579 A1 | 7/2003 | Yoshida et al. |
| 2003/0162995 A1 | 8/2003 | Cesti et al. |

FOREIGN PATENT DOCUMENTS

| CA | 2721357 A1 | 11/2009 |
| JP | 52-71443 | 6/1977 |
| JP | 61-183257 | 8/1986 |
| JP | 64-85956 | 3/1989 |
| JP | 1-230550 | 9/1989 |
| JP | 6-25086 A | 2/1994 |
| JP | 3382289 B | 2/1994 |
| JP | 6-56985 | 3/1994 |
| JP | 2002-212335 | 7/2002 |
| JP | 2003-231774 | 8/2003 |
| JP | 2003-252846 | 9/2003 |
| JP | 2004-262834 | 9/2004 |
| JP | 2004-262835 | 9/2004 |
| JP | 2004-339147 | 12/2004 |
| WO | 2005/118584 A2 | 12/2005 |

OTHER PUBLICATIONS

Dyer et al., Thermal Degradation of Alkyl N-Phenylcarbamates, J. Am. Chem., 81:2138-2143 (1958).
Hofmann, Ueber die Aromatischen Cyanate, Berchete der Deutechen Chemischen Gesellschaft, 3:653-658 (1870).
Tarbell et al., Acidic and Basic Catalysis in Urethan Formation, J. Am. Chem. 64:2229-2230 (1942).
Polymer Chemistry, 20(214):102-107 (1963).
The Collection of Preliminary Manuscripts or the Study Group of the Research Association for Feedstock Recycling of Plastics, 3:31-32 (2001).
Polymer Preprints, Japan, vol. 54, No. 1 (2005).

*Primary Examiner* — Johann Richter
*Assistant Examiner* — Jennifer C Sawyer
(74) *Attorney, Agent, or Firm* — Morgan, Lewis & Bockius LLP

(57) ABSTRACT

An object of the present invention is to provide a process for producing isocyanates, which are industrially useful compounds, without using phosgene, and to provide a process for chemically recycling waste polycarbonate resin. The present invention discloses a process enabling isocyanate compounds to be produced without using phosgene as a raw material by subjecting a carbamic acid ester compound obtained by a reaction between an aromatic polycarbonate resin and an amine compound to a thermal decomposition reaction, while at the same time disclosing a process enabling chemical recycling of aromatic polycarbonate resin by recovering a divalent aromatic hydroxy compound forming aromatic polycarbonates.

11 Claims, 9 Drawing Sheets

ISOCYANATES AND AROMATIC HYDROXY COMPOUNDS

RELATED APPLICATIONS

This application is a Divisional Application of U.S. application Ser. No. 12/743,767, filed May 19, 2010, now U.S. Pat. No. 7,977,504 which is a U.S. National Phase Application of International Application No. PCT/JP2008/070765, filed Nov. 14, 2008, which claims the benefit of Japanese Patent Application No. 2007-299703, filed Nov. 19, 2007, Japanese Patent Application No. 2007-299497, filed Nov. 19, 2007, and Japanese Patent Application No. 2007-299504, filed Nov. 19, 2007, all of which are herein incorporated by reference in their entireties.

TECHNICAL FIELD

The present invention relates to a process for producing isocyanate compounds and aromatic hydroxy compounds, which are useful for raw materials for aromatic polycarbonate.

BACKGROUND ART

Plastics are used as product materials in all fields of daily life, and the amount of plastics used is increasing each year. Accompanying this increase, the amount of discarded plastics is also extremely large, thus resulting in the treatment of plastics becoming a significant social issue.

At present, the majority of plastic products are simply disposed of by being incinerated or buried following completion of their use. However, when waste plastic having high heat of combustion in terms of calories is disposed of by incinerating in an ordinary refuse incinerator, abnormal combustion occurs resulting in the problem of damage to the incinerator furnace. In addition, not only does this manner of disposal result in wasted resources, but it also causes environmental problems in terms of environmental contamination and discharge of carbon dioxide gas. Thus, it is extremely important to recycle waste plastics from the viewpoint of the formation of a recycling society as well.

Methods used to recycle waste plastics include material recycling, in which waste plastics are reused as is, chemical recycling, in which waste plastics are chemically degraded followed by recovery of monomers and other useful chemical raw materials, and thermal recycling, in which thermal energy is recovered from waste plastics. Among these, since material recycling is accompanied by heat treatment of the waste plastics, the heat treatment has a considerable effect on both the chemical properties and physical properties of the waste plastics, and frequently results in problems such as deterioration of impact resistance, deformation under a load or high temperatures, tensile strength, bending strength, fluidity and other properties. In addition, although thermal recycling offers the advantage of being able to inhibit the amount of fossil fuels used as a result of effectively utilizing thermal energy, there are also numerous problems such as damage to the incinerator furnace, discharge of carbon dioxide gas and the need to implement measures against dioxins as described above.

Aromatic polycarbonate resins constitute a typical engineering plastic having superior transparency, optical properties and mechanical properties, and are extremely high added value materials used in a wide range of applications such as CDs, DVDs and other optical fields, various home appliances, cameras, cell phones, OA equipment, medical equipment, automobiles and other industrial fields, sports and other recreational fields, and roofing materials, alternative glass materials and other construction fields.

Various methods have been proposed thus far for chemically recycling aromatic polycarbonates.

According to Non-patent document 1, although a process is described for obtaining bisphenol A by chemically decomposing polycarbonate resin with ammonia water, decomposition of the polycarbonate resin requires a long period of time, thereby resulting in the problem of being unsuitable for large-volume processing of waste plastics.

In addition, Patent document 1 discloses a process for recovering bisphenol A by decomposing polycarbonate resin by adding ammonia water and an organic solvent in the form of aluminum chloride to a polycarbonate resin. However, there are many cases in which chemical decomposition of the polycarbonate requires a long period of time with this process as well.

Examples of processes for shortening the time required to decompose polycarbonate resins in this manner may include a process for recovering useful materials from waste plastics having polycarbonate resin for the main component thereof disclosed in Patent document 2 which comprises a step of chemically decomposing a polycarbonate resin in a solution containing waste plastic and a decomposition agent in the form of a primary amine, and a step of recovering the decomposition product in the form of a useful material. In this process, the polycarbonate resin is reacted with an excess of primary amine equivalent to six or more times the number of moles of carbonic acid ester groups as calculated from the molecular weight of the repetitive units of the polycarbonate resin, followed by recovery of useful materials such as the degradation product in the form of bisphenol A and urea derivatives. In addition, according to Non-patent document 2, it is described that bisphenol A and 1,3-dimethyl-2-imidazolidinone (DMI) are obtained by decomposing polycarbonate with N,N'-dimethyl-1,2-diaminoethane. Among these recovery products, although bisphenol A can be easily imagined to be used as a raw material for the production of polycarbonate resin, there are no descriptions regarding the use of urea derivatives or DMI, and the usefulness thereof is unclear.

In addition, according to Patent document 3, for example, a process is disclosed for obtaining bisphenols and diaryl carbonate by cleaving polycarbonate resin by carrying out a transesterification reaction between polycarbonate resin and phenol in the presence of a catalyst. It is described to the effect that monomers obtained by this process can be recondensed to produce polymer plastics. In addition, in Patent document 4, for example, a process for recovering useful materials from waste plastics mainly composed of polycarbonate is disclosed whereby decomposition products are recovered in the form of useful materials by chemically decomposing polycarbonate resin in a solution containing an organic solvent that causes polycarbonate resin to dissolve or swell, a tertiary amine and a lower alcohol. In this process, examples of recovered useful materials are listed as being bisphenol A and carbonic acid ester. Since each of these processes requires an alkaline catalyst to decompose the polycarbonate by a transesterification reaction, there are many cases in which the procedure becomes complex, such as requiring deactivation of the alkaline catalyst during separation and purification of the decomposition products.

As an example of a process not requiring a catalyst, Non-patent document 3 discloses a process for producing bisphenol A by hydrolyzing polycarbonate under supercritical conditions (supercritical aqueous or subcritical aqueous conditions). Although there is no description regarding yield and the reaction efficiency is not clearly stated in this document, since the reaction is carried out under high temperature and high pressure conditions, not only is there the possibility of the concurrent occurrence of thermal decomposition of the bisphenol A under such conditions, but also due to the extremely strong acidity of the water itself under supercritical aqueous conditions along with the high temperature in excess of 300° C. and high pressure in excess of 200 atm, the apparatus and equipment become excessively complex, thereby making it difficult to carry out the process economically.

Patent document 5 discloses a process for recovering aromatic bisphenol and carbonic acid ester formed by reacting polycarbonate obtained by melting and filtration from disk-shaped optical recording media with an aliphatic alcohol having 1 to 6 carbon atoms in a subcritical or supercritical state. In this process, in addition to the reaction vessel being large since an excess of aliphatic alcohol is used based on the polycarbonate, similar to the case of the process described in Non-patent document 3, since the reaction vessel is required to be of a design capable of withstanding a high temperature and high pressure state, the large reactors used in typical commercial plants encounter difficulties both in terms of design and economy.

Although polycarbonates have a typical structure in which, for example, a bisphenol A unit and a carbonyl unit are alternately arranged in a polymer chain, the chemical recycling processes disclosed thus far disclose technologies that only attempt to effectively recycle one of these units or technologies that only attempt to recover the bisphenol A. However, there have been no successful examples of chemically recycling both units in the form of effective compounds at a high recovery yield.

Thus, although there has been a strong desire for the development of a process for chemically recycling waste aromatic polycarbonate resins, an effective process has yet to be found.

As previously described, polycarbonate resins are formed from, for example, bisphenol A and carbonyl units. The recovery of this carbonyl unit in the form of an industrially effective compound is an important issue for chemical recycling of polycarbonate resins. Examples of industrially effective compounds having a carbonyl group may include carbonic acid esters and isocyanates. Isocyanates are widely used as production raw materials of polyurethane foam, paints and adhesives. The most commonly used process for industrial production of isocyanates consists of reacting an amine compound with phosgene (phosgene method), and nearly the entire amount of isocyanates produced throughout the world are produced according to the phosgene method. However, the phosgene method has numerous problems.

Firstly, this method requires the use of a large amount of phosgene as raw material. Phosgene is extremely toxic and requires special handling precautions to prevent exposure of handlers thereof, and also requires special apparatuses to detoxify waste.

Secondly, since highly corrosive hydrogen chloride is produced in large amounts as a by-product of the phosgene method, in addition to requiring a process for detoxifying the hydrogen chloride, in many cases hydrolytic chlorine is contained in the isocyanates produced, which may have a detrimental effect on the weather resistance and heat resistance of polyurethane products in the case of using isocyanates produced using the phosgene method.

On the basis of this background, a process for producing isocyanates has been sought that does not use phosgene. One example of a method for producing isocyanate compounds without using phosgene that has been proposed involves thermal decomposition of carbamic acid esters. Isocyanates and hydroxy compounds have long been known to be obtained by thermal decomposition of carbamic acid esters (see, for example, Non-patent document 4). The basic reaction is illustrated by the following formula:

$$R(NHCOOR')_a \rightarrow R(NCO)_a + aR'OH \quad (1)$$

(wherein R represents an organic residue having a valence of a, R' represents a monovalent organic residue, and a represents an integer of 1 or more).

Among carbamic acid esters, aryl carbamates, in which the ester group is an aromatic group, offer the advantage of allowing the setting of a lower temperature for the thermal decomposition reaction as compared with alkyl carbamates in which the ester group is an alkyl group (see, for example, Patent document 6).

Various processes have been disclosed thus far as processes for producing aryl carbamates. Patent document 7 describes the obtaining of a corresponding alkyl aryl monocarbamate at a yield of 90 to 95% by reacting an alkyl monoamine and a diaryl carbonate in the presence of a solvent such as benzene, dioxane or carbon tetrachloride. In addition, Patent document 8 proposes a process for continuously producing methyl carbamic acid phenyl ester from methylamine and diphenyl carbonate.

However, each of these processes produces alkyl aryl carbamate using a lower alkyl monoamine for the amine, and do not constitute a process for producing an alkyl aryl polycarbamate. In the case of producing a corresponding alkyl polycarbamic acid aryl ester from an alkyl polyamine such as alkyl diamine or alkyl triamine, there are difficult problems that are completely different from those in the case of using an alkyl monoamine. This is because, although only urea compounds are produced as by-products due to side reactions represented by formula (3) and/or formula (4) in addition to the reaction represented by formula (2) in the case of an alkyl monoamine, in the case of an alkyl polyamine such as alkyl diamine or alkyl triamine, an extremely large number of types of urea compounds are produced as by-products, such as the compounds represented by formula (5) and/or formula (6) and/or formula (7).

(2)

(3)

(4)

(5)

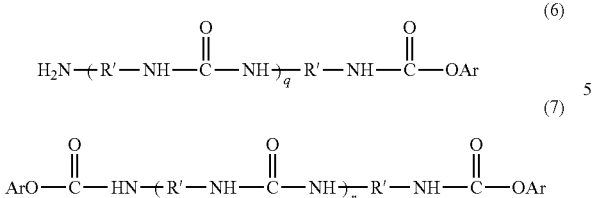

(6)

(7)

(wherein R' represents a monovalent alkyl group or aromatic group, Ar represents a monovalent aromatic group, and p, q and r respectively represent an integer of 1 or more.)

Namely, there are the problems of these various urea compound side reactions causing a decrease in the yield of the target compound in the form of the alkyl aryl polycarbamate, as well as the extreme difficulty in separating and purifying the target product from a mixture of these urea compounds and polyurea compounds.

Although Patent document 9 describes a process for synthesizing an aromatic urethane by reacting an aromatic amine and a diaryl carbonate in the presence of a Lewis acid catalyst at a temperature of 140 to 230° C., in this process as well, the use of a Lewis acid results in the problem of corrosion of the apparatus as well as difficulty in separating and recovering the product.

Patent document 10 discloses a process for producing alkyl aryl polycarbamate comprising the use of 1 to 3 equivalents of diaryl carbonate based on 1 equivalent of amino group of alkyl polyamine, using an aromatic hydroxy compound for the reaction solvent, and carrying out the reaction in the state of a substantially homogeneous solution when producing alkyl polycarbamic acid aryl ester by reacting alkyl polyamine and diaryl carbonate. According to this patent document, alkyl polycarbamic acid aryl ester is obtained with high selectivity and at a high yield of normally 96% or more and 98% or more in preferable embodiments thereof. However, since the formation of urea compounds has been confirmed, although in very small amounts, this process is unable to completely avoid the formation of urea compounds.

On the other hand, thermal decomposition of carbamic acid esters is susceptible to the simultaneous occurrence of various irreversible side reactions such as thermal denaturation reactions undesirable for carbamic acid esters or condensation of isocyanates formed by the thermal decomposition. Examples of these side reactions may include a reaction in which urea bonds are formed as represented by the following formula (8), a reaction in which carbodiimides are formed as represented by the following formula (9), and a reaction in which isocyanurates are formed as represented by the following formula (10) (see, Non-patent document 4 and Non-patent document 5).

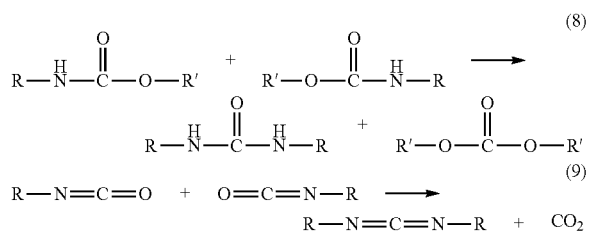

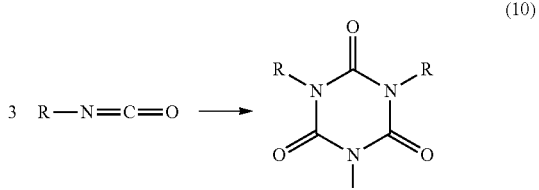

(10)

(wherein R and R' independently represent monovalent alkyl groups or aromatic groups.)

In addition to these side reactions leading to a decrease in yield and selectivity of the target isocyanate, in the production of polyisocyanates in particular, these reactions may make long-term operation difficult as a result of, for example, causing the precipitation of polymeric solids that clog the reaction vessel.

Various processes have been proposed thus far for producing isocyanates using a carbamic acid ester for the raw material.

According to Patent document 11, an aromatic diisocyanate and/or polyisocyanate is produced by going through the following two steps. More specifically, in the first step, an aromatic primary amine and/or an aromatic primary polyamine is reacted with an O-alkyl carbamate in the presence or absence of a catalyst and in the presence or absence of urea and alcohol to form an aryl diurethane and/or aryl polyurethane followed by removal of the ammonia formed as necessary. In the second step, an aromatic isocyanate and/or aromatic polyisocyanate are obtained by thermal decomposition of the aryl diurethane and/or aryl polyurethane.

There are several known methods for forming a corresponding isocyanate and alcohol by thermal decomposition of a (cyclic) aliphatic, and particularly an aromatic, monourethane and diurethane, including methods carried out in the gaseous phase at a high temperature, and methods carried out in a liquid phase under comparatively low temperature conditions. In these methods, however, the reaction mixture gives rise to the side reactions described above, thereby causing, for example, the formation of sediment, polymeric substances and obstructions in the reaction vessel and recovery apparatus, or the formation of substances that adhere to the sidewalls of the reaction vessel, thereby resulting in poor economic efficiency in the case of producing isocyanates over a long period of time.

Thus, the use of a chemical method, such as the use of a special catalyst (see, for example, Patent document 12 and Patent document 13) or a catalyst combined with an inert solvent (see, for example, Patent document 14), has been disclosed to improve the yield in the thermal decomposition of urethane.

More specifically, Patent document 15 describes a process for producing hexamethylene diisocyanate consisting of thermal decomposition of hexamethylene diethyl urethane in the presence of dibenzyl toluene used as a catalyst and in the presence of a catalyst mixture composed of methyl toluene sulfonate and diphenyl tin dichloride. However, since there are no detailed descriptions of production or isolation of the starting components or purification and arbitrary recovery of the solvent and catalyst mixture, the economic efficiency of this process could not be evaluated.

According to the method described in Patent document 16, urethane can be easily broken down into isocyanate and alcohol in a carbon-containing fluidized bed without using a catalyst. In addition, according to the description of Patent document 17, hexamethylene dialkyl urethane can be decomposed in the gaseous phase at a temperature in excess of 300° C. in the presence or absence of a gas permeable packaging material made of, for example, carbon, copper, brass, steel, zinc, aluminum, titanium, chromium, cobalt or quartz to form hexamethylene diisocyanate. According to the description of Patent document 16, this method is carried out in the presence of a hydrogen halide and/or hydrogen halide donor. However, this method is unable to achieve a yield of hexamethylene diisocyanate of 90% or more. This is because the decomposition products are partially recombined resulting in the formation of urethane bonds. Thus, the hexamethylene diisocyanate is required to be additionally purified by distillation, which frequently increases yield loss.

Moreover, according to the description of Patent document 18, a monocarbamate is disclosed to be able to be decomposed with favorable yield without using a solvent and in the presence or absence of a catalyst and/or stabilizer at a comparatively low temperature and advantageously under a reduced pressure. The decomposition products (monoisocyanate and alcohol) are removed from a boiling reaction mixture by distillation and separately captured by separative condensation. A method for removing by-products formed during thermal decomposition consisting of partially removing the reaction mixture outside the system is described in a generic form. Thus, although by-products can be removed from the bottom of the reaction vessel, problems remain with respect to the case of adherence to the sidewalls of the reaction vessel as previously described, and problems with respect to long-term operation remain unsolved. In addition, there is no description regarding industrial utilization of the removed reaction mixture (containing large amounts of useful components).

According to the description of Patent document 19, thermal decomposition of an aliphatic, alicyclic or aromatic polycarbamate is carried out in the presence of an inert solvent at 150° C. to 350° C. and 0.001 to 20 bar, and in the presence or absence of a catalyst and an assistant in the form of hydrogen chloride, organic acid chloride, alkylation agent or organic tin chloride. By-products formed, can be continuously removed from the reaction vessel together with the reaction solution, for example, and a corresponding amount of fresh solvent or recovered solvent is added simultaneously. A shortcoming of this method is, for example, a reduction in the space-time yield of polyisocyanate as a result of using a refluxing solvent, while also requiring considerable energy, including that for recovery of the solvent. Moreover, the assistants used are volatile under the reaction conditions, resulting in the potential for contamination of the decomposition products. In addition, the amount of residue is large based on the formed polyisocyanate, thus leaving room for doubt regarding economic efficiency and the reliability of industrial methods.

According to the description of Patent document 20, a method is described for continuous thermal decomposition of a carbamate such as the alicyclic diurethane, 5-(ethoxycarbonylamino)-1-(ethoxycarbonylaminomethyl)-1,3,3-trimethylcyclohexane, supplied along the inner surface of a tubular reactor in a liquid form in the presence of a high boiling point solvent. This method has the shortcomings of low yield during production of (cyclic) aliphatic diisocyanates and low selectivity. In addition, there is no description of a continuous method accompanying recovery of recombined or partially decomposed carbamates, while there is also no mention made of post-treatment of solvent containing the by-products and catalyst.

Patent document 1: Japanese Patent Application Laid-open No. H6-25086
Patent document 2: Japanese Patent Application Laid-open No. 2003-231774
Patent document 3: Japanese Patent Application Laid-open No. H6-56985
Patent document 4: Japanese Patent Application Laid-open No. 2002-212335
Patent document 5: Japanese Patent Application Laid-open No. 2004-339147
Patent document 6: U.S. Pat. No. 3,992,430
Patent document 7: Japanese Patent Application Laid-open No. S52-71443
Patent document 8: Japanese Patent Application Laid-open No. S61-183257
Patent document 9: Japanese Patent Application Laid-open No. 2004-262834
Patent document 10: Japanese Patent Application Laid-open No. H1-230550
Patent document 11: U.S. Pat. No. 4,290,970
Patent document 12: U.S. Pat. No. 2,692,275
Patent document 13: U.S. Pat. No. 3,734,941
Patent document 14: U.S. Pat. No. 4,081,472
Patent document 15: U.S. Pat. No. 4,388,426
Patent document 16: U.S. Pat. No. 4,482,499
Patent document 17: U.S. Pat. No. 4,613,466
Patent document 18: U.S. Pat. No. 4,386,033
Patent document 19: U.S. Pat. No. 4,388,246
Patent document 20: U.S. Pat. No. 4,692,550
Non-patent document 1: Polymer Chemistry, Vol. 20, No. 214, 1963
Non-patent document 2: the Collection of Preliminary Manuscripts of the Study Group of the Research Association for Feedstock Recycling of Plastics, Vol. 3, pp. 31-32, 2001
Non-patent document 3: Polymer Preprints, Japan, Vol. 54, No. 1, 2005
Non-patent document 4: Berchte der Deutechen Chemischen Gesellschaft, Vol. 3, p. 653, 1870
Non-patent document 5: Journal of American Chemical Society, Vol. 81, p. 2138, 1959

DISCLOSURE OF INVENTION

Problems to be Solved by the Invention

An object of the present invention is to provide a process for producing isocyanates, which are industrially useful compounds, without using phosgene as described above, while at the same time providing a process for chemically recycling waste aromatic polycarbonate resin.

Means for Solving the Problems

As a result of conducting extensive studies on the above-mentioned problems, the inventors of the present invention found that the above-mentioned problems can be solved by a process in which a carbamic acid ester compound obtained by a reaction between an aromatic polycarbonate resin and a specific polyamine compound is subjected to a thermal decomposition reaction, thereby leading to completion of the present invention.

Namely, in a first aspect of the present invention, there is provided:

[1] a process for producing a divalent aromatic hydroxy compound and an isocyanate compound, comprising the steps of:
reacting an aromatic polycarbonate resin and an amine compound having a primary amino group to obtain a mixture containing a carbamic acid ester and a compound having an aromatic hydroxyl group, which are originated from the aromatic polycarbonate; and
subjecting the carbamic acid ester to a thermal decomposition reaction to obtain the divalent aromatic hydroxy compound and the isocyanate compound,

[2] the process according to item [1], wherein the reaction between the aromatic polycarbonate resin and the amine compound is carried out in the presence of a monovalent aromatic hydroxy compound as a reaction solvent,

[3] the process according to item [1] or [2], wherein the reaction between the aromatic polycarbonate resin and the amine compound is carried out in the absence of a catalyst,

[4] the process according to any one of items [1] to [3], wherein the thermal decomposition reaction of the carbamic acid ester is carried out in the absence of a catalyst,

[5] the process according to any one of items [1] to [4], wherein a reactor in which the reaction between the aromatic polycarbonate resin and the amine compound is carried out differs from a reactor used for the thermal decomposition reaction of the carbamic acid ester,

[6] the process according to item [5], further comprising transferring the mixture containing the carbamic acid ester obtained by reacting the aromatic polycarbonate resin with the amine compound to the reactor used for the thermal decomposition reaction of the carbamic acid ester,

[7] the process according to item [6], wherein the mixture containing the carbamic acid ester is transferred while maintaining a temperature within a range of from 10° C. to 180° C.,

[8] the process according to any one of items [1] to [7], wherein a low boiling point component formed in the thermal decomposition reaction of the carbamic acid ester is recovered from the reactor in a form of a gaseous phase component, and a liquid phase component is recovered from a bottom of the reactor,

[9] the process according to item [8], wherein the recovery of the gaseous phase component and the recovery of the liquid phase component are carried out continuously,

[10] the process according to item [8] or [9], wherein the low boiling point component is an isocyanate compound and/or a monovalent aromatic hydroxy compound,

[11] the process according to item [8] or [9], wherein the liquid phase component contains a divalent aromatic hydroxy compound and/or carbamic acid ester,

[12] the process according to any one of items [8] to [11], wherein the liquid phase component is recycled to a top of the reactor in which the thermal decomposition reaction is carried out,

[13] the process according to any one of items [1] to [12], wherein the aromatic polycarbonate resin is a waste polycarbonate resin,

[14] the process according to any one of items [1] to [13], wherein the amine compound is a compound represented by the following formula (11):

$$R^1 \!-\!\!\!+\!\!NH_2)_n \tag{11}$$

(wherein $R^1$ represents a group selected from the group consisting of aliphatic groups having 1 to 20 carbon atoms and aromatic groups having 6 to 20 carbon atoms, the above groups contain an atom selected from carbon and oxygen atoms, and have an atomic number equal to n, and n represents an integer of from 2 to 10),

[15] the process according to item [14], wherein the amine compound is a diamine compound in which n is 2 in formula (11),

[16] the process according to item [2], wherein a standard boiling point of the monovalent aromatic hydroxy compound is lower than a standard boiling point of the divalent aromatic hydroxy compound,

[17] the process according to item [2] or [16], wherein the monovalent aromatic hydroxy compound is an aromatic hydroxy compound which is represented by the following formula (12) and which has at least one substituent $R^2$:

(12)

(wherein ring A represents an aromatic hydrocarbon ring which has 6 to 20 carbon atoms and which may have a substituent, and the ring A may be a monocyclic or heterocyclic ring, and $R^2$ represents an aliphatic group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the above groups contain an atom selected from the group consisting of carbon, oxygen and nitrogen atoms, and $R^2$ may also bond with A to form a ring structure),

[18] the process according to item [17], wherein the monovalent aromatic hydroxy compound has a structure in which the ring A contains at least one structure selected from the group consisting of a benzene ring, a naphthalene ring and an anthracene ring.

In addition, in the second aspect of the present invention, there is provided:

[19] a carbamic acid ester compound represented by the following formula (13):

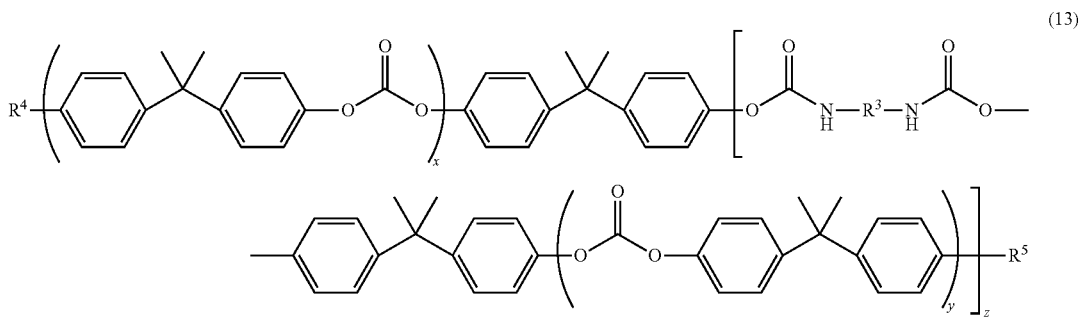

(13)

(wherein $R^3$ represents a group selected from the group consisting of aliphatic groups having 1 to 20 carbon atoms and aromatic groups containing 6 to 20 carbon atoms, the above groups contain an atom selected from carbon and oxygen atoms, each of $R^4$ and $R^5$ independently represents a substituent selected from the group represented by the following formula (14):

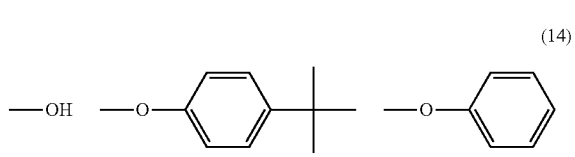

(14)

and, each of x, y and z independently represents an integer of 0 or more).

Advantageous Effects of the Invention

According to the present invention, in addition to being able to efficiently produce an isocyanate compound without using phosgene, a divalent aromatic hydroxy compound can be obtained by chemically recycling an aromatic polycarbonate resin.

Figure 1:
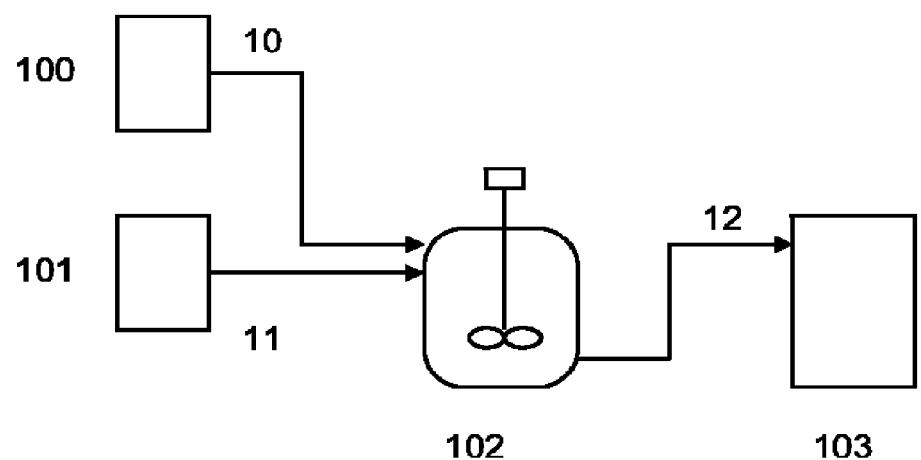
FIG. 1 illustrates a conceptual drawing showing an apparatus for preparing an aromatic polycarbonate-containing mixed liquid used in an example of the of the present invention.

DESCRIPTION OF REFERENCE NUMERICALS (FIG. 1)
100, 101, 103: storage tank, 102: reactor, 10, 11, 12: line
(FIG. 2)
103, 201, 203: storage tank, 202: reactor, 21, 22, 23: line
(FIG. 3)
203, 304, 308, 309, 311, 316, 317, 321, 322: storage tank,
301: thin film distillation apparatus, 302, 312, 313, 318: continuous multistage distillation column
303, 308, 314, 319: condenser
305, 310, 315, 320: reboiler
31, 32, 33, 34, 35, 36, 37, 38, 39, 40, 41, 42, 43, 44, 45, 46, 47, 48, 49, 50, 51, 52: line
(FIG. 4)
203, 407, 404, 409, 411, 416, 417, 421, 422: storage tank
401: thin film distillation apparatus, 402, 412, 413, 418: continuous multistage distillation column
403, 308, 414, 419: condensor, 405, 415, 420: reboiler
60, 61, 62, 63, 64, 65, 66, 67, 68, 69, 70, 71, 72, 73, 74, 75, 76, 77, 78, 79, 80, 81, 82: line
(FIG. 5)
203, 504, 506, 507, 510, 512, 515, 517: storage tank
501: thin film distillation apparatus, 502, 508, 513: continuous multistage distillation column
503, 509, 514: condenser, 505, 511, 516: reboiler
A1, A2, A3, A4, A5, A6, A7, A8, A9, A10, A11, A12, A13, A14, A15, A16, A17, A18, A19, A20, A21: line
(FIG. 6)
512, 603, 605, 608, 610: storage tank, 601, 606: continuous multistage distillation column
602, 607: condenser, 604, 609: reboiler
B1, B2, B3, B4, B5, B6, B7, B8, B9, B10, B11, B12: line
(FIG. 7)
700, 701, 702, 714, 715: storage tank, 703: reactor
704, 707, 710: continuous multistage distillation column, 705, 708, 711: condenser
706, 709, 713: reboiler
C1, C2, C3, C4, C5, C6, C7, C8, C9, C10, C11, C12, C13, C14, C15, C16, C17: line

BEST MODE FOR CARRYING OUT THE INVENTION

The following provides a detailed explanation of the best mode for carrying out the present invention (to be referred to as "the present embodiment"). Furthermore, the present invention is not limited to the following present embodiment, but rather can be modified in various ways within the scope of the gist thereof.

The process of the present embodiment is a process for producing a divalent aromatic hydroxy compound and an isocyanate compound, which comprises the steps of: reacting an aromatic polycarbonate resin and an amine compound having primary amino groups to obtain a mixture containing a carbamic acid ester and a compound having an aromatic hydroxyl group, which are originated from the aromatic polycarbonate; and subjecting the carbamic acid ester to a thermal decomposition reaction to obtain the divalent aromatic hydroxy compound and the isocyanate compound.

<Aromatic Polycarbonate>

An aromatic polycarbonate used in the present embodiment refers to a polymer having a carbonic acid ester of a divalent aromatic hydroxy compound as a repetitive unit thereof, and is represented by the following formula (15):

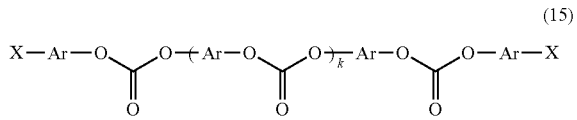

(15)

(wherein Ar represents a divalent aromatic group having 6 to 20 carbon atoms, and k represents an integer of 0 or more).

There are no particular limitations on the Ar constituting the aromatic polycarbonate, and is an aromatic group having the structure $Ar(OH)_2$, in which two hydroxyl groups are added to the Ar group, or in other words, an aromatic group in which two hydroxyl groups have been removed from a divalent aromatic hydroxy compound. Examples of the divalent aromatic hydroxy compound represented by $Ar(OH)_2$ may preferably include a divalent aromatic hydroxy compound represented by the following formula (16):

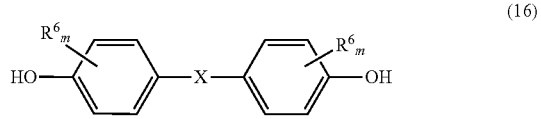

(16)

(wherein X represents an alkylidene or cycloalkylidene, which has 1 to 8 carbon atoms, S, $SO_2$, O, C=O or a single bond, $R^6$ represents an alkyl group having 1 to 5 carbon atoms, Cl or Br, and m represents an integer of 0 to 2).

Examples of such divalent aromatic hydroxy compounds may include 4,4'-dihydroxydiphenyl, α,α'-bis-(4-hydroxyphenyl)-m-diisopropylbenzene, 4,4'-dihydroxydiphenyl sulfide, 2,2-bis-(4-hydroxyphenyl)-propane, 2,2-bis-(3,5-dimethyl-4-hydroxyphenyl)-propane, 2,2-bis-(3,5-dichloro-4-hydroxyphenyl)-propane, 2,2-bis-(3,5-dibromo-4-hydroxyphenyl)-propane, 1,1-bis-(4-hydroxyphenyl)-cyclohexane and 1,1-bis-(4-hydroxyphenyl)-3,3,5-trimethylcyclohexane.

Among these divalent aromatic hydroxy compounds, 4,4'-dihydroxyphenyl, α,α'-bis-(4-hydroxyphenyl)-m-diisopropylbenzene, 2,2-bis-(4-hydroxyphenyl)-propane and 1,1-bis-(4-hydroxyphenyl)-3,3,5-trimethylcyclohexane are preferable, 2,2-bis-(4-hydroxyphenyl)-propane is more preferable.

The aromatic polycarbonate used in the present embodiment may also be produced by any polymerization method. Although generally produced by a method such as interfacial polymerization using phosgene or melt polymerization using diphenyl carbonate, either method may be used and production is independent of the production method.

Although there are no particular limitations on the degree of polymerization of the aromatic polycarbonate provided it has thermoplasticity, the weight average molecular weight is generally within a range of from 1,000 to 500,000, preferably within a range of from 5,000 to 200,000, and more preferably within a range of from 10,000 to 80,000. The weight average molecular weight of the aromatic polycarbonate can be measured by gel permeation chromatography (solvent: tetrahydrofuran, standard: polystyrene).

The aromatic polycarbonate used in the present embodiment may also have a branched structure as a result of incorporating a multifunctional branching agent in the molecular chain thereof. Examples of branching agents may include phloroglucinol, 4,6-dimethyl-2,4,6-tri-(4-hydroxyphenyl)-heptane, 1,3,5-tri-(4-hydroxyphenylbenzene), 1,1,1-tri-(4-hydroxyphenyl)-ethane, tri-(4-hydroxyphenyl)-phenyl-methane, 2,2-bis-[4,4-bis-(4-hydroxyphenyl)-cyclohexyl]-propane, 2,4-bis-(4-hydroxyphenyl-isopropyl)-phenol, 2,6-bis-(2-hydroxy-5'-methyl-benzyl)-4-methylphenol, 2-(4-hydroxyphenyl)-2-(2,4-dihydroxyphenyl)-propane, hexa-(4-(4-hydroxyphenyl-isopropyl)-phenyl)-orthophthalic acid ester, tetra-(4-hydroxyphenyl)-methane, tetra-(4-(4-hydroxyphenyl-isopropyl)-phenoxy-methane, isatin-bis-cresol, pentaerythritol, 2,4-dihydroxybenzoic acid, trimesic acid, cyanuric acid, 1,4-bis-((4',4''-dihydroxytriphenyl)-methyl)-benzene, α,α',α''-tris-(4-hydroxyphenyl)-1,3,4-triisopropenyl benzene and the like.

In addition, there are cases in which the aromatic polycarbonate contains a chain terminator and/or a group originated from a chain terminator following the use of a chain terminator such as phenol, octylphenol (including isomers), cumylphenol (including isomers) or butylphenol (including isomers) during production thereof, and even such aromatic polycarbonates can be used in the process of the present embodiment without any problems whatsoever.

Although aromatic polycarbonates are generally used in lenses, compact disks, construction materials, automobile parts, chasses of OA equipment and camera bodies and the like, aromatic polycarbonates that have become waste following completion of use can also be used in the present embodiment. In addition, aromatic polycarbonates in the form of, for example, waste generated during the production of moldings, cuttings or moldings no longer able to be used, defective moldings or aromatic polycarbonates used to clean molding machines can also be used in the present embodiment. Thus, aromatic polycarbonates may contain commonly used known additives such as mineral fillers such as quartz powder, glass powder, glass fibers, stabilizers, UV protectants, lubricants, pigments or dyes, as well as polymeric blended components using as raw materials thereof styrene, acrylonitrile or butadiene and the like. In such cases, these aromatic polycarbonates may be used as is in a state of being contained within a range that does not impair the essence of the present embodiment, or these aromatic polycarbonates may be used following the removal of such additives or blended components by suitable methods. Known methods can be used to remove these additives and the like, examples of which may include methods such as filtration, membrane separation, centrifugal separation, precipitation, distillative separation or crystallization in a state of an aromatic polycarbonate melt or, for example, a solution containing a solvent to be described later and the aromatic polycarbonate, and methods using adsorptive separation using, for example, activated charcoal, diatomaceous earth, cellulose or zeolite.

The aromatic polycarbonate used in the present embodiment is preferably used in a state of being granulated or crushed to a suitable size. From the viewpoint of allowing the reaction with the polyamine compound to proceed rapidly, the mean dimension is preferably 10 mm or less, and from the viewpoints of ease of granulation or crushing and handling ease, preferably 0.5 mm or more. Namely, the mean dimension is preferably from 0.1 to 10 mm and more preferably from 0.5 to 5 mm.

<Amine Compound>

An amine compound represented by the following formula (17) is used for the amine compound having primary amino groups used in the present embodiment:

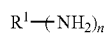

$$R^1 \!\!-\!\!(NH_2)_n \tag{17}$$

(wherein $R^1$ represents a group selected from the group consisting of aliphatic groups having 1 to 20 carbon atoms and aromatic groups having 6 to 20 carbon atoms, the above groups contain an atom selected from carbon and oxygen atoms, and have an atomic number equal to n, and n represents an integer of 2 to 10).

In formula (17) above, a polyamine compound in which n is 2 or more is used preferably, and a diamine compound in which n is 2 is used more preferably.

Examples of $R^1$ in formula (17) above may include alkyl groups having 1 to 20 carbon atoms and cycloalkyl groups having 5 to 20 carbon atoms, and examples of such $R^1$ groups may include linear hydrocarbon groups such as a methylene, dimethylene, trimethylene, tetramethylene, pentamethylene, hexamethylene or octamethylene group; unsubstituted alicyclic hydrocarbon groups such as a cyclopentane, cyclohexane, cycloheptane, cyclooctane or bis(cyclohexyl)alkane; alkyl-substituted cyclohexanes such as methylcyclopentane, ethylcyclopentane, methylcyclohexane (including isomers), ethylcyclohexane (including isomers), propylcyclohexane (including isomers), butylcyclohexane (including isomers), pentylcyclohexane (including isomers) or hexylcyclohexane (including isomers); dialkyl-substituted cyclohexanes such as dimethylcyclohexane (including isomers), diethylcyclohexane (including isomers) or dibutylcyclohexane (including isomers); trialkyl-substituted cyclohexanes such as 1,5,5-trimethylcyclohexane, 1,5,5-triethylcyclohexane, 1,5,5-tripropylcyclohexane (including isomers) or 1,5,5-tributylcyclohexane (including isomers); monoalkyl-substituted benzenes such as toluene, ethylbenzene or propylbenzene; dialkyl-substituted benzenes such as xylene, diethylbenzene or dipropylbenzene; and aromatic hydrocarbons such as diphenylalkane or benzene. Among these, groups such as hexamethylene, phenylene, diphenylmethane, toluene, cyclohexane, xylenyl, methylcyclohexane, isophorone and dicyclohexylmethane are used preferably.

Examples of such amine compounds may include aliphatic diamines such as hexamethylene diamine, 4,4'-methylenebis(cyclohexylamine) (including isomers), cyclohexane diamine (including isomers) or 3-aminomethyl-3,5,5-trimethylcyclohexylamine (including isomers); and aromatic diamines such as phenylene diamine (including isomers), toluene diamine (including isomers) or 4,4'-methylene dianiline. Among these, aliphatic diamines such as hexamethylene diamine, 4,4'-methylenebis(cyclohexylamine) (including isomers), cyclohexane diamine (including isomers) or 3-aminomethyl-3,5,5-trimethylcyclohexylamine (including isomers) are used preferably, hexamethylene diamine, 4,4'-methylenebis(cyclohexylamine) and 3-aminomethyl-3,5,5-trimethylcyclohexylamine are used more preferably.

<Reaction of Aromatic Polycarbonate and Amine Compound Having Primary Amino Groups>

Next, an explanation is provided of the reaction between an aromatic polycarbonate and an amine compound having primary amino groups in the present embodiment.

Although varying according to the reacted compounds, the reaction conditions under which the reaction between the aromatic polycarbonate and the amine compound having primary amino groups is carried out are such that the stiochiometric ratio of the amino groups of the amine compound to the carbonate bonds that comprises the aromatic polycarbonate is preferably within a range of from 0.0001 to 2. This stoichiometric ratio is preferably 1 or less, more preferably 0.5 or less and even more preferably 0.2 or less in order to reduce urea compound by-products and enhance the yield of the target compound in the form of carbamic acid ester. In addition, although it is preferable that the amino groups of the amine compound be as few as possible with respect to carbonate bonds constituting the aromatic polycarbonate in order to increase the reaction rate and allow the reaction to rapidly be completed, in consideration of the size of the reactor, the stiochiometric ratio is more preferably 0.001 or more and even more preferably 0.01 or more.

The reaction temperature is generally within a range of from 0 to 300° C. Although a high temperature is preferable in order to increase the reaction rate, since undesirable reactions may occur at high temperatures, the reaction temperature is preferably within a range of from 10° C. to 250° C. and more preferably within a range of from 20° C. to 200° C. A known cooling apparatus or heating apparatus may be installed in the reactor used to carry out the reaction in order to maintain a constant reaction temperature. The reaction is preferably carried out in an inert gas atmosphere such as nitrogen, helium, argon or neon. In addition, although varying according to the types of compounds used and reaction temperature, the reaction may be carried out at decreased pressure, normal pressure or increased pressure, and the reaction pressure is generally within a range of from 20 to $1 \times 10^{-6}$ Pa. There are no particular limitations on the reaction time (residence time in the case of a continuous process), and is generally from 0.001 to 50 hours, preferably from 0.01 to 20 hours and more preferably from 0.1 to 10 hours. In addition, the reaction can also be completed after confirming the formation of a desired amount of carbamic acid ester by liquid chromatography, for example, by sampling the reaction liquid, the reaction can be completed after confirming that the average degree of polymerization of aromatic polycarbonate present in the reaction liquid has decreased to a prescribed value by, for example, gel permeation chromatography, or the reaction can be completed after confirming that amino groups and/or carbonate groups have been consumed to a prescribed level by, for example, NMR.

In the present embodiment, a catalyst is preferably not used in the reaction between the aromatic polycarbonate and the amine compound having primary amino groups. When a carbamic acid ester is heated in the presence of a metal component derived from a catalyst during transport of the reaction mixture and a thermal decomposition reaction of carbamic acid ester contained in the reaction mixture to be described later, a tendency may be observed in which a thermal denaturation reaction and the like of the carbamic acid ester occurs easily. Although a catalyst can be used when carrying out the reaction between the aromatic polycarbonate and the amine compound having primary amino groups, and transfer of the reaction mixture and a thermal decomposition reaction can be carried out after going through a step of removing the catalyst, this results in an increase in the number of steps, thereby making this undesirable.

However, the use of a catalyst is not negated for the purpose of completing the reaction in a short period of time, lowering the reaction temperature and the like. In general, since aromatic amine compounds have lower reactivity than aliphatic amines, in the case of using an aromatic amine compound for the amine compound, the use of a catalyst may be effective. In the case of using a catalyst, examples of catalysts that can be used may include organic metal compounds and inorganic metal compounds of tin, lead, copper or titanium, and basic catalysts such as alcoholates of alkaline metals or alkaline earth metals in the form of methylates, ethylates or butyrates (including isomers) of lithium, sodium, potassium, calcium or barium.

Although the reaction between the aromatic hydroxy compounds and the amine compounds having primary amino groups as described above can be carried out in the presence or absence of solvent, it is preferably carried out in the presence of a solvent, and more preferably carried out in a homogeneous solution in the presence of a solvent. Although there are no particular limitations on the solvent, solvents that dissolve or swell aromatic polycarbonates are preferable, and examples of solvents that are used preferably may include aliphatic ethers such as tetrahydrofuran or 1,4-dioxane; aromatic ethers such as diphenyl ether, di(methylphenyl)ether (including isomers), di(ethylphenyl)ether (including isomers) or di(propylphenyl)ether; aromatic hydrocarbons such as benzene, toluene or xylene (including isomers); aromatic hydroxy compounds such as phenol; and halogen compounds such as methylene chloride, chloroform, carbon tetrachloride or chlorobenzene. Among these, aromatic hydroxy compounds are more preferable since they easily dissolve aromatic polycarbonates and the carbamic acid ester formed, and demonstrate the effect of inhibiting the occurrence of thermal denaturation reactions on the carbamic acid ester formed as will be described later.

More preferably, the solvent is a monovalent aromatic hydroxy compound having a single hydroxyl group directly bonded to the aromatic hydrocarbon ring constituting the aromatic hydroxy compound. Although an aromatic hydroxy compound having two or more hydroxyl groups bonded directly to the aromatic hydrocarbon ring constituting the aromatic hydroxy compound can also be used as an aromatic hydroxy compound constituting the composition of the present embodiment, since there are cases in which the viscosity of the solution increases in the reaction between the aromatic polycarbonate and the amine compound, this may cause a decrease in reaction efficiency or a decrease in efficiency when transferring the reaction solution to be described later.

An aromatic hydroxy compound having at least one substituent $R^2$ as represented by the following formula (18) is preferable for the monovalent aromatic hydroxy compound mentioned above:

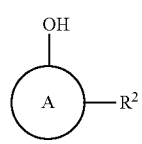

(18)

(wherein ring A represents an aromatic hydrocarbon ring which has 6 to 20 carbon atoms, and which may have a substituent, and the ring A may be a monocyclic or heterocyclic ring, $R^2$ represents an aliphatic group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the above groups contain an atom selected from the group consisting of carbon, oxygen and nitrogen atoms, and $R^2$ may bond with A to form a ring structure).

Examples of $R^2$ in formula (18) above may include aliphatic alkyl groups in which the number of carbon atoms constituting the group is a number selected from integers of from 1 to 20, such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), a dodecyl group (including isomers) or an octadecyl group (including isomers); aliphatic alkoxy groups in which the number of carbon atoms constituting the group is a number selected from integers of from 1 to 20, such as a methoxy group, an ethoxy group, a propoxy group (including isomers), a butyloxy group (including isomers), a pentyloxy group (including isomers), a hexyloxy group (including isomers), a heptyloxy group (including isomers), an octyloxy group (including isomers), a nonyloxy group (including isomers), a decyloxy group (including isomers), a decyloxy group (including isomers), a dodecyloxy group (including isomers) or an octadecyloxy group (including isomers); aryl groups in which the number of carbon atoms constituting the group is from 6 to 20, such as a phenyl group, a methylphenyl group (including isomers), an ethylphenyl group (including isomers), a propylphenyl group (including isomers), a butylphenyl group (including isomers), a pentylphenyl group (including isomers), a hexylphenyl group (including isomers), a heptylphenyl group (including isomers), an octylphenyl group (including isomers), a nonylphenyl group (including isomers), a decylphenyl group (including isomers), a biphenyl group (including isomers), a dimethylphenyl group (including isomers), a diethylphenyl group (including isomers), a dipropylphenyl group (including isomers), a dibutylphenyl group (including isomers), a dipentylphenyl group (including isomers), a dihexylphenyl group (including isomers), a diheptylphenyl group (including isomers), a terphenyl group (including isomers), a trimethylphenyl group (including isomers), a triethylphenyl group (including isomers), a tripropylphenyl group (including isomers) or a tributylphenyl group (including isomers); aryloxy groups in which the number of carbon atoms constituting the group is from 6 to 20, such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a heptylphenoxy group (including isomers), an octylphenoxy group (including isomers), a nonylphenoxy group (including isomers), a decylphenoxy group (including isomers), a phenylphenoxy group (including isomers), a dimethylphenoxy group (including isomers), a diethylphenoxy group (including isomers), a dipropylphenoxy group (including isomers), a dibutylphenoxy group (including isomers), a dipentylphenoxy group (including isomers), a dihexylphenoxy group (including isomers), a diheptylphenoxy group (including isomers), a diphenylphenoxy group (including isomers), a trimethylphenoxy group (including isomers), a triethylphenoxy group (including isomers), a tripropylphenoxy group (including isomers) or a tributylphenoxy group (including isomers); aralkyl groups in which the number of carbon atoms constituting the group is from 7 to 20, such as a phenylmethyl group, a phenylethyl group (including isomers), a phenylpropyl group (including isomers), a phenylbutyl group (including isomers), a phenylpentyl group (including isomers), a phenylhexyl group (including isomers), a phenylheptyl group (including isomers), a phenyloctyl group (including isomers) or a phenylnonyl group (including isomers); and aralkyloxy groups in which the number of carbon atoms constituting the group is from 7 to 20, such as a phenylmethoxy group, a phenylethoxy group (including isomers), a phenylpropyloxy group (including isomers), a phenylbutyloxy group (including isomers), a phenylpentyloxy group (including isomers), a phenylhexyloxy group (including isomers), a phenylheptyloxy group (including isomers), a phenyloctyloxy group (including isomers) or a phenylnonyloxy group (including isomers).

Examples of ring A in formula (18) above may include a benzene ring, a naphthalene ring, an anthracene ring, a phenanthracene ring, a naphthacene ring, a chrysene ring, a pyrene ring, a triphenylene ring, a pentalene ring, an azulene ring, a heptalene ring, an indacene ring, a biphenylene ring, an acenaphthylene ring, an aceanthrylene ring and an acephenanthrylene ring, while preferable examples may include rings selected from the group consisting of a benzene ring, a naphthalene ring and an anthracene ring. In addition, these rings may have a substituent other than the above-mentioned $R^2$, examples of which may include aliphatic alkyl groups in which the number of carbon atoms constituting the group is a number selected from integers of from 1 to 20, such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), a dodecyl group (including isomers) or an octadecyl group (including isomers); aliphatic alkoxy groups in which the number of carbon atoms constituting the group is a number selected from integers of from 1 to 20, such as a methoxy group, an ethoxy group, a propoxy group (including isomers), a butyloxy group (including isomers), a pentyloxy group (including isomers), a hexyloxy group (including isomers), a heptyloxy group (including isomers), an octyloxy group (including isomers), a nonyloxy group (including isomers), a decyloxy group (including isomers), a dodecyloxy group (including isomers) or an octadecyloxy group (including isomers); aryl groups in which the number of carbon atoms constituting the group is from 6 to 20, such as a phenyl group, a methylphenyl group (including isomers), an ethylphenyl group (including isomers), a propylphenyl group (including isomers), a butylphenyl group (including isomers), a pentylphenyl group (including isomers), a hexylphenyl group (including isomers), a heptylphenyl group (including isomers), an octylphenyl group (including isomers), a nonylphenyl group (including isomers), a decylphenyl group (including isomers), a biphenyl group (including isomers), a dimethylphenyl group (including isomers), a diethylphenyl group (including isomers), a dipropylphenyl group (including isomers), a dibutylphenyl group (including isomers), a dipentylphenyl group (including isomers), a dihexylphenyl group (including isomers), a diheptylphenyl group (including isomers), a terphenyl group (including isomers), a trimethylphenyl group (including isomers), a triethylphenyl group (including isomers), a tripropylphenyl group (including isomers) or a tributylphenyl group (including isomers); aryloxy groups in which the number of carbon atoms constituting the group is from 6 to 20, such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a heptylphenoxy group (including isomers), an octylphenoxy group (including isomers), a nonylphenoxy group (including isomers), a decylphenoxy group (including isomers), a phenylphenoxy group (including isomers), a dimethylphenoxy group (including isomers), a diethylphenoxy group (including isomers), a dipropylphenoxy group (including isomers), a dibutylphenoxy group (including isomers), a dipentylphenoxy group (including isomers), a dihexylphenoxy group (including isomers), a diheptylphenoxy group (including isomers), a diphenylphenoxy group (including isomers), a trimethylphenoxy group (including isomers), a triethylphenoxy group (including isomers), a tripropylphenoxy group (including isomers) or a tributylphenoxy group (including isomers); aralkyl groups in which the number of carbon atoms constituting the group is from 7 to 20, such as a phenylmethyl group, a phenylethyl group (including isomers), a phenylpropyl group (including isomers), a phenylbutyl group (including isomers), a phenylpentyl group (including isomers), a phenylhexyl group (including isomers), a phenylheptyl group (including isomers), a phenyloctyl group (including isomers) or a phenylnonyl group (including isomers); and aralkyloxy groups in which the number of carbon atoms constituting the group is from 7 to 20, such as a phenylmethoxy group, a phenylethoxy group (including isomers), a phenylpropyloxy group (including isomers), a phenylbutyloxy group (including isomers), a phenylpentyloxy group (including isomers), a phenylhexyloxy group (including isomers), a phenylheptyloxy group (including isomers), a phenyloctyloxy group (including isomers) or a phenylnonyloxy group (including isomers).

Examples of such monovalent aromatic hydroxy compounds may include mono-substituted phenols such as phenol, methyl-phenol (including isomers), ethyl-phenol (including isomers), propyl-phenol (including isomers), butyl-phenol (including isomers), pentyl-phenol (including isomers), hexyl-phenol (including isomers), heptyl-phenol (including isomers), octyl-phenol (including isomers), nonyl-phenol (including isomers), decyl-phenol (including isomers), dodecyl-phenol (including isomers), phenyl-phenol (including isomers), phenoxyphenol (including isomers) or cumyl-phenol (including isomers); di-substituted phenols such as dimethyl-phenol (including isomers), diethyl-phenol (including isomers), dipropyl-phenol (including isomers), dibutyl-phenol (including isomers), dipentyl-phenol (including isomers), dihexyl-phenol (including isomers), diheptyl-phenol (including isomers), dioctyl-phenol (including isomers), dinonyl-phenol (including isomers), didecyl-phenol (including isomers), didodecyl-phenol (including isomers), diphenyl-phenol (including isomers), diphenoxyphenol (including isomers), dicumyl-phenol (including isomers), methyl-ethyl-phenol (including isomers), methyl-propyl-phenol (including isomers), methyl-butyl-phenol (including isomers), methyl-pentyl-phenol (including isomers), methyl-hexyl-phenol (including isomers), methyl-heptyl-phenol (including isomers), methyl-octyl-phenol (including isomers), methyl-nonyl-phenol (including isomers), methyl-decyl-phenol (including isomers), methyl-dodecyl-phenol (including isomers), methyl-phenyl-phenol (including isomers), methyl-phenoxyphenol (including isomers), methyl-cumyl-phenol (including isomers), ethyl-propyl-phenol (including isomers), ethyl-butyl-phenol (including isomers), ethyl-pentyl-phenol (including isomers), ethyl-hexyl-phenol (including isomers), ethyl-heptyl-phenol (including isomers), ethyl-octyl-phenol (including isomers), ethyl-nonyl-phenol (including isomers), ethyl-decyl-phenol (including isomers), ethyl-dodecyl-phenol (including isomers), ethyl-phenyl-phenol (including isomers), ethyl-phenoxyphenol (including isomers), ethyl-cumyl-phenol (including isomers), propyl-butyl-phenol (including isomers), propyl-pentyl-phenol (including isomers), propyl-hexyl-phenol (including isomers), propyl-heptyl-phenol (including isomers), propyl-octyl-phenol (including isomers), propyl-nonyl-phenol (including isomers), propyl-decyl-phenol (including isomers), propyl-dodecyl-phenol (including isomers), propyl-phenyl-phenol (including isomers), propyl-phenoxyphenol (including isomers), propyl-cumyl-phenol (including isomers), butyl-pentyl-phenol (including isomers), butyl-hexyl-phenol (including isomers), butyl-heptyl-phenol (including isomers), butyl-octyl-phenol (including isomers), butyl-nonyl-phenol (including isomers), butyl-decyl-phenol (including isomers), butyl-dodecyl-phenol (including isomers), butyl-phenyl-phenol (including isomers), butyl-phenoxyphenol (including isomers), butyl-cumyl-phenol (including isomers), pentyl-hexyl-phenol (including isomers), pentyl-heptyl-phenol (including isomers), pentyl-octyl-phenol (including isomers), pentyl-nonyl-phenol (including isomers), pentyl-decyl-phenol (including isomers), pentyl-dodecyl-phenol (including isomers), pentyl-phenyl-phenol (including isomers), pentyl-phenoxyphenol (including isomers), pentyl-cumyl-phenol (including isomers), hexyl-heptyl-phenol (including isomers), hexyl-octyl-phenol (including isomers), hexyl-nonyl-phenol (including isomers), hexyl-decyl-phenol (including isomers), hexyl-dodecyl-phenol (including isomers), hexyl-phenyl-phenol (including isomers), hexyl-phenoxyphenol (including isomers), hexyl-cumyl-phenol (including isomers), heptyl-octyl-phenol (including isomers), heptyl-nonyl-phenol (including isomers), heptyl-decyl-phenol (including isomers), heptyl-dodecyl-phenol (including isomers), heptyl-phenyl-phenol (including isomers), heptyl-phenoxyphenol (including isomers), heptyl-cumyl-phenol (including isomers), octyl-nonyl-phenol (including isomers), octyl-decyl-phenol (including isomers), octyl-dodecyl-phenol (including isomers), octyl-phenyl-phenol (including isomers), octyl-phenoxyphenol (including isomers), octyl-cumyl-phenol (including isomers), nonyl-decyl-phenol (including isomers), nonyl-dodecyl-phenol (including isomers), nonyl-phenyl-phenol (including isomers), nonyl-phenoxyphenol (including isomers), nonyl-cumyl-phenol (including isomers), dodecyl-phenyl-phenol (including isomers), dodecyl-phenoxyphenol (including isomers) or dodecyl-cumyl-phenol (including isomers); and tri-substituted phenols such as trimethyl-phenol (including isomers), triethyl-phenol (including isomers), tripropyl-phenol (including isomers), tributyl-phenol (including isomers), tripentyl-phenol (including isomers), trihexyl-phenol (including isomers), triheptyl-phenol (including isomers), trioctyl-phenol (including isomers), trinonyl-phenol (including isomers), tridecyl-phenol (including isomers), tridodecyl-phenol (including isomers), triphenyl-phenol (including isomers), triphenoxyphenol (including isomers), tricumyl-phenol (including isomers), dimethyl-ethyl-phenol (including isomers), dimethyl-propyl-phenol (including isomers), dimethyl-butyl-phenol (including isomers), dimethyl-pentyl-phenol (including isomers), dimethyl-hexyl-phenol (including isomers), dimethyl-heptyl-phenol (including isomers), dimethyl-octyl-phenol (including isomers), dimethyl-nonyl-phenol (including isomers), dimethyl-decyl-phenol (including isomers), dimethyl-dodecyl-phenol (including isomers), dimethyl-phenyl-phenol (including isomers), dimethyl-phenoxyphenol (including isomers), dimethyl-cumyl-phenol (including isomers), diethyl-methyl-phenol (including isomers), diethyl-propyl-phenol (including isomers), diethyl-butyl-phenol (including isomers), diethyl-pentyl-phenol (including isomers), diethyl-hexyl-phenol (including isomers), diethyl-heptyl-phenol (including isomers), diethyl-octyl-phenol (including isomers), diethyl-nonyl-phenol (including isomers), diethyl-decyl-phenol (including isomers), diethyl-dodecyl-phenol (including isomers), diethyl-phenyl-phenol (including isomers), diethyl-phenoxyphenol (including isomers), diethyl-cumyl-phenol (including isomers), dipropyl-methyl-phenol (including isomers), dipropyl-ethyl-phenol (including isomers), dipropyl-butyl-phenol (including isomers), dipropyl-pentyl-phenol (including isomers), dipropyl-hexyl-phenol (including isomers), dipropyl-heptyl-phenol (including isomers), dipropyl-octyl-phenol (including isomers), dipropyl-nonyl-phenol (including isomers), dipropyl-decyl-phenol (including isomers), dipropyl-dodecyl-phenol (including isomers), dipropyl-phenyl-phenol (including isomers), dipropyl-phenoxyphenol (including isomers), dipropyl-cumyl-phenol (including isomers), dibutyl-methyl-phenol (including isomers), dibutyl-ethyl-phenol (including isomers), dibutyl-propyl-phenol (including isomers), dibutyl-pentyl-phenol (including isomers), dibutyl-hexyl-phenol (including isomers), dibutyl-heptyl-phenol (including isomers), dibutyl-octyl-phenol (including isomers), dibutyl-nonyl-phenol (including isomers), dibutyl-decyl-phenol (including isomers), dibutyl-dodecyl-phenol (including isomers), dibutyl-phenyl-phenol (including isomers), dibutyl-phenoxyphenol (including isomers), dibutyl-cumyl-phenol (including isomers), dipentyl-methyl-phenol (including isomers), dipentyl-ethyl-phenol (including isomers), dipentyl-propyl-phenol (including isomers), dipentyl-butyl-phenol (including isomers), dipentyl-hexyl-phenol (including isomers), dipentyl-heptyl-phenol (including isomers), dipentyl-octyl-phenol (including isomers), dipentyl-nonyl-phenol (including isomers), dipentyl-decyl-phenol (including isomers), dipentyl-dodecyl-phenol (including isomers), dipentyl-phenyl-phenol (including isomers), dipentyl-phenoxyphenol (including isomers), dipentyl-cumyl-phenol (including isomers), dihexyl-methyl-phenol (including isomers), dihexyl-ethyl-phenol (including isomers), dihexyl-propyl-phenol (including isomers), dihexyl-butyl-phenol (including isomers), dihexyl-pentyl-phenol (including isomers), dihexyl-heptyl-phenol (including isomers), dihexyl-octyl-phenol (including isomers), dihexyl-nonyl-phenol (including isomers), dihexyl-decyl-phenol (including isomers), dihexyl-dodecyl-phenol (including isomers), dihexyl-phenyl-phenol (including isomers), dihexyl-phenoxyphenol (including isomers), dihexyl-cumyl-phenol (including isomers), diheptyl-methyl-phenol (including isomers), diheptyl-ethyl-phenol (including isomers), diheptyl-propyl-phenol (including isomers), diheptyl-butyl-phenol (including isomers), diheptyl-pentyl-phenol (including isomers), diheptyl-hexyl-phenol (including isomers), diheptyl-octyl-phenol (including isomers), diheptyl-nonyl-phenol (including isomers), diheptyl-decyl-phenol (including isomers), diheptyl-dodecyl-phenol (including isomers), diheptyl-phenyl-phenol (including isomers), diheptyl-phenoxyphenol (including isomers), diheptyl-cumyl-phenol (including isomers), dioctyl-methyl-phenol (including isomers), dioctyl-ethyl-phenol (including isomers), dioctyl-propyl-phenol (including isomers), dioctyl-butyl-phenol (including isomers), dioctyl-pentyl-phenol (including isomers), dioctyl-hexyl-phenol (including isomers), dioctyl-heptyl-phenol (including isomers), dioctyl-nonylphenol (including isomers), dioctyl-decyl-phenol (including isomers), dioctyl-dodecyl-phenol (including isomers), dioctyl-phenyl-phenol (including isomers), dioctyl-phenoxyphenol (including isomers), dioctyl-cumyl-phenol (including isomers), dinonyl-methyl-phenol (including isomers), dinonyl-ethyl-phenol (including isomers), dinonyl-propyl-phenol (including isomers), dinonyl-butyl-phenol (including isomers), dinonyl-pentyl-phenol (including isomers), dinonyl-hexyl-phenol (including isomers), dinonyl-heptyl-phenol (including isomers), dinonyl-octyl-phenol (including isomers), dinonyl-decyl-phenol (including isomers), dinonyl-dodecyl-phenol (including isomers), dinonyl-phenyl-phenol (including isomers), dinonyl-phenoxyphenol (including isomers), dinonyl-cumyl-phenol (including isomers), didecyl-methyl-phenol (including isomers), didecyl-ethyl-phenol (including isomers), didecyl-propyl-phenol (including isomers), didecyl-butyl-phenol (including isomers), didecyl-pentyl-phenol (including isomers), didecyl-hexyl-phenol (including isomers), didecyl-heptyl-phenol (including isomers), didecyl-octyl-phenol (including isomers), didecyl-nonyl-phenol (including isomers), didecyl-dodecyl-phenol (including isomers), didecyl-phenyl-phenol (including isomers), didecyl-phenoxyphenol (including isomers), didecyl-cumyl-phenol (including isomers), didodecyl-methyl-phenol (including isomers), didodecyl-ethyl-phenol (including isomers), didodecyl-propyl-phenol (including isomers), didodecyl-butyl-phenol (including isomers), didodecyl-pentyl-phenol (including isomers), didodecyl-hexyl-phenol (including isomers), didodecyl-heptyl-phenol (including isomers), didodecyl-octyl-phenol (including isomers), didodecyl-nonyl-phenol (including isomers), didodecyl-decyl-phenol (including isomers), didodecyl-dodecyl-phenol (including isomers), didodecyl-phenyl-phenol (including isomers), didodecyl-phenoxyphenol (including isomers), didodecyl-cumyl-phenol (including isomers), diphenyl-methyl-phenol (including isomers), diphenyl-ethyl-phenol (including isomers), diphenyl-propyl-phenol (including isomers), diphenyl-butyl-phenol (including isomers), diphenyl-pentyl-phenol (including isomers), diphenyl-hexyl-phenol (including isomers), diphenyl-heptyl-phenol (including isomers), diphenyl-octyl-phenol (including isomers), diphenyl-nonyl-phenol (including isomers), diphenyl-decyl-phenol (including isomers), diphenyl-dodecyl-phenol (including isomers), diphenyl-phenoxyphenol (including isomers), diphenyl-cumyl-phenol (including isomers), diphenoxymethyl-phenol (including isomers), diphenoxyethyl-phenol (including isomers), diphenoxypropyl-phenol (including isomers), diphenoxybutyl-phenol (including isomers), diphenoxypentyl-phenol (including isomers), diphenoxyhexyl-phenol (including isomers), diphenoxyheptyl-phenol (including isomers), diphenoxyoctyl-phenol (including isomers), diphenoxynonyl-phenol (including isomers), diphenoxydecyl-phenol (including isomers), diphenoxydodecyl-phenol (including isomers), diphenoxyphenyl-phenol (including isomers), diphenoxycumyl-phenol (including isomers), dicumyl-methyl-phenol (including isomers), dicumyl-ethyl-phenol (including isomers), dicumyl-propyl-phenol (including isomers), dicumyl-butyl-phenol (including isomers), dicumyl-pentyl-phenol (including isomers), dicumyl-hexyl-phenol (including isomers), dicumyl-heptyl-phenol (including isomers), dicumyl-octyl-phenol (including isomers), dicumyl-nonyl-phenol (including isomers), dicumyl-decyl-phenol (including isomers), dicumyl-dodecyl-phenol (including isomers), dicumyl-phenyl-phenol (including isomers), dicumyl-phenoxyphenol (including isomers), methyl-ethyl-propyl-phenol (including isomers), methyl-ethyl-butyl-phenol (including isomers), methyl-ethyl-pentyl-phenol (including isomers), methyl-ethyl-hexyl-phenol (including isomers), methyl-ethyl-heptyl-phenol (including isomers), methyl-ethyl-octyl-phenol (including isomers), methyl-ethyl-nonyl-phenol (including isomers), methyl-ethyl-decyl-phenol (including isomers), methyl-ethyl-dodecyl-phenol (including isomers), methyl-ethyl-phenyl-phenol (including isomers), methyl-ethyl-phenoxyphenol (including isomers), methyl-ethyl-cumyl-phenol (including isomers), methyl-propyl-butyl-phenol (including isomers), methyl-propyl-pentyl-phenol (including isomers), methyl-propyl-hexyl-phenol (including isomers), methyl-propyl-heptyl-phenol (including isomers), methyl-propyl-octyl-phenol (including isomers), methyl-propyl-nonyl-phenol (including isomers), methyl-propyl-decyl-phenol (including isomers), methyl-propyl-dodecyl-phenol (including isomers), methyl-propyl-phenyl-phenol (including isomers), methyl-propyl-phenoxyphenol (including isomers), methyl-propyl-cumyl-phenol (including isomers), methyl-butyl-pentyl-phenol (including isomers), methyl-butyl-hexyl-phenol (including isomers), methyl-butyl-heptyl-phenol (including isomers), methyl-butyl-octyl-phenol (including isomers), methyl-butyl-nonyl-phenol (including isomers), methyl-butyl-decyl-phenol (including isomers), methyl-butyl-dodecyl-phenol (including isomers), methyl-butyl-phenyl-phenol (including isomers), methyl-butyl-phenoxyphenol (including isomers), methyl-butyl-cumyl-phenol (including isomers), methyl-pentyl-hexyl-phenol (including isomers), methyl-pentyl-heptyl-phenol (including isomers), methyl-pentyl-octyl-phenol (including isomers), methyl-pentyl-nonyl-phenol (including isomers), methyl-pentyl-decyl-phenol (including isomers), methyl-pentyl-dodecyl-phenol (including isomers), methyl-pentyl-phenyl-phenol (including isomers), methyl-pentyl-phenoxyphenol (including isomers), methyl-pentyl-cumyl-phenol (including isomers), methyl-hexyl-heptyl-phenol (including isomers), methyl-hexyl-octyl-phenol (including isomers), methyl-hexyl-nonyl-phenol (including isomers), methyl-hexyl-decyl-phenol (including isomers), methyl-hexyl-dodecyl-phenol (including isomers), methyl-hexyl-phenyl-phenol (including isomers), methyl-hexyl-phenoxyphenol (including isomers), methyl-hexyl-cumyl-phenol (including isomers), ethyl-propyl-butyl-phenol (including isomers), ethyl-propyl-pentyl-phenol (including isomers), ethyl-propyl-hexyl-phenol (including isomers), ethyl-propyl-heptyl-phenol (including isomers), ethyl-propyl-octyl-phenol (including isomers), ethyl-propyl-nonyl-phenol (including isomers), ethyl-propyl-decyl-phenol (including isomers), ethyl-propyl-dodecyl-phenol (including isomers), ethyl-propyl-phenyl-phenol (including isomers), ethyl-propyl-phenoxyphenol (including isomers), ethyl-propyl-cumyl-phenol (including isomers), ethyl-butyl-phenol (including isomers), ethyl-butyl-pentyl-phenol (including isomers), ethyl-butyl-hexyl-phenol (including isomers), ethyl-butyl-heptyl-phenol (including isomers), ethyl-butyl-octyl-phenol (including isomers), ethyl-butyl-nonyl-phenol (including isomers), ethyl-butyl-decyl-phenol (including isomers), ethyl-butyl-dodecyl-phenol (including isomers), ethyl-butyl-phenyl-phenol (including isomers), ethyl-butyl-phenoxyphenol (including isomers), ethyl-butyl-cumyl-phenol (including isomers), ethyl-pentyl-hexyl-phenol (including isomers), ethyl-pentyl-heptyl-phenol (including isomers), ethyl-pentyl-octyl-phenol (including isomers), ethyl-pentyl-nonyl-phenol (including isomers), ethyl-pentyl-decyl-phenol (including isomers), ethyl-pentyl-dodecyl-phenol (including isomers), ethyl-pentyl-phenyl-phenol (including isomers), ethyl-pentyl-phenoxyphenol (including isomers), ethyl-pentyl-cumyl-phenol (including isomers), ethyl-hexyl-heptyl-phenol (including isomers), ethyl-hexyl-octyl-phenol (including isomers), ethyl-hexyl-nonyl-phenol (including isomers), ethyl-hexyl-decyl-phenol (including isomers), ethyl-hexyl-dodecyl-phenol (including isomers), ethyl-hexyl-phenyl-phenol (including isomers), ethyl-hexyl-phenoxyphenol (including isomers), ethyl-hexyl-cumyl-phenol (including isomers), ethyl-heptyl-octyl-phenol (including isomers), ethyl-heptyl-nonyl-phenol (including isomers), ethyl-heptyl-decyl-phenol (including isomers), ethyl-heptyl-dodecyl-phenol (including isomers), ethyl-heptyl-phenyl-phenol (including isomers), ethyl-heptyl-phenoxyphenol (including isomers), ethyl-heptyl-cumyl-phenol (including isomers), ethyl-octyl-phenol (including isomers), ethyl-octyl-nonyl-phenol (including isomers), ethyl-octyl-decyl-phenol (including isomers), ethyl-octyl-dodecyl-phenol (including isomers), ethyl-octyl-phenyl-phenol (including isomers), ethyl-octyl-phenoxyphenol (including isomers), ethyl-octyl-cumyl-phenol (including isomers), ethyl-nonyl-decyl-phenol (including isomers), ethyl-nonyl-dodecyl-phenol (including isomers), ethyl-nonyl-phenyl-phenol (including isomers), ethyl-nonyl-phenoxyphenol (including isomers), ethyl-nonyl-cumyl-phenol (including isomers), ethyl-decyl-dodecyl-phenol (including isomers), ethyl-decyl-phenyl-phenol (including isomers), ethyl-decyl-phenoxyphenol (including isomers), ethyl-decyl-cumyl-phenol (including isomers), ethyl-dodecyl-phenyl-phenol (including isomers), ethyl-dodecyl-phenoxyphenol (including isomers), ethyl-dodecyl-cumyl-phenol (including isomers), ethyl-phenyl-phenoxyphenol (including isomers), ethyl-phenyl-cumyl-phenol (including isomers), propyl-butyl-phenol (including isomers), propyl-butyl-pentyl-phenol (including isomers), propyl-butyl-hexyl-phenol (including isomers), propyl-butyl-heptyl-phenol (including isomers), propyl-butyl-octyl-phenol (including isomers), propyl-butyl-nonyl-phenol (including isomers), propyl-butyl-decyl-phenol (including isomers), propyl-butyl-dodecyl-phenol (including isomers), propyl-butyl-phenyl-phenol (including isomers), propyl-butyl-phenoxyphenol (including isomers), propyl-butyl-cumyl-phenol (including isomers), propyl-pentyl-phenol (including isomers), propyl-pentyl-hexyl-phenol (including isomers), propyl-pentyl-heptyl-phenol (including isomers), propyl-pentyl-octyl-phenol (including isomers), propyl-pentyl-nonyl-phenol (including isomers), propyl-pentyl-decyl-phenol (including isomers), propyl-pentyl-dodecyl-phenol (including isomers), propyl-pentyl-phenyl-phenol (including isomers), propyl-pentyl-phenoxyphenol (including isomers), propyl-pentyl-cumyl-phenol (including isomers), propyl-hexyl-phenol (including isomers), propyl-hexyl-heptyl-phenol (including isomers), propyl-hexyl-octyl-phenol (including isomers), propyl-hexyl-nonyl-phenol (including isomers), propyl-hexyl-decyl-phenol (including isomers), propyl-hexyl-dodecyl-phenol (including isomers), propyl-hexyl-phenyl-phenol (including isomers), propyl-hexyl-phenoxyphenol (including isomers), propyl-hexyl-cumyl-phenol (including isomers), propyl-heptyl-octyl-phenol (including isomers), propyl-heptyl-nonyl-phenol (including isomers), propyl-heptyl-decyl-phenol (including isomers), propyl-heptyl-dodecyl-phenol (including isomers), propyl-heptyl-phenyl-phenol (including isomers), propyl-heptyl-phenoxyphenol (including isomers), propyl-heptyl-cumyl-phenol (including isomers), propyl-octyl-nonyl-phenol (including isomers), propyl-octyl-decyl-phenol (including isomers), propyl-octyl-dodecyl-phenol (including isomers), propyl-octyl-phenyl-phenol (including isomers), propyl-octyl-phenoxyphenol (including isomers), propyl-octyl-cumyl-phenol (including isomers), propyl-nonyl-decyl-phenol (including isomers), propyl-nonyl-dodecyl-phenol (including isomers), propyl-nonyl-phenyl-phenol (including isomers), propyl-nonyl-phenoxyphenol (including isomers), propyl-nonyl-cumyl-phenol (including isomers), propyl-decyl-dodecyl-phenol (including isomers), propyl-decyl-phenyl-phenol (including isomers), propyl-decyl-phenoxyphenol (including isomers), propyl-decyl-cumyl-phenol (including isomers), propyl-dodecyl-phenyl-phenol (including isomers), propyl-dodecyl-phenoxyphenol (including isomers), propyl-dodecyl-cumyl-phenol (including isomers), methyl-phenol (including isomers), ethyl-phenol (including isomers), propyl-phenol (including isomers), butyl-phenol (including isomers), pentyl-phenol (including isomers), hexyl-phenol (including isomers), heptyl-phenol (including isomers), octyl-phenol (including isomers), nonyl-phenol (including isomers), decyl-phenol (including isomers), dodecyl-phenol (including isomers), phenyl-phenol (including isomers), phenoxyphenol (including isomers) cumyl-phenol (including isomers) propyl-phenyl-phenoxyphenol (including isomers), propyl-phenyl-cumyl-phenol (including isomers), propyl-phenoxy-cumyl-phenol (including isomers), propyl-butyl-pentyl-phenol (including isomers), propyl-butyl-hexyl-phenol (including isomers), propyl-butyl-heptyl-phenol (including isomers), propyl-butyl-octyl-phenol (including isomers), propyl-butyl-nonyl-phenol (including isomers), propyl-butyl-decyl-phenol (including isomers), propyl-butyl-dodecyl-phenol (including isomers), propyl-butyl-phenyl-phenol (including isomers), propyl-butyl-phenoxyphenol (including isomers), propyl-butyl-cumyl-phenol (including isomers), propyl-pentyl-phenol (including isomers), propyl-pentyl-hexyl-phenol (including isomers), propyl-pentyl-heptyl-phenol (including isomers), propyl-pentyl-octyl-phenol (including isomers), propyl-pentyl-nonyl-phenol (including isomers), propyl-pentyl-decyl-phenol (including isomers), propyl-pentyl-dodecyl-phenol (including isomers), propyl-pentyl-phenyl-phenol (including isomers), propyl-pentyl-phenoxyphenol (including isomers), propyl-pentyl-cumyl-phenol (including isomers), propyl-hexyl-heptyl-phenol (including isomers), propyl-hexyl-octyl-phenol (including isomers), propyl-hexyl-nonyl-phenol (including isomers), propyl-hexyl-decyl-phenol (including isomers), propyl-hexyl-dodecyl-phenol (including isomers), propyl-hexyl-phenyl-phenol (including isomers), propyl-hexyl-phenoxyphenol (including isomers), propyl-hexyl-cumyl-phenol (including isomers), propyl-heptyl-octyl-phenol (including isomers), propyl-heptyl-nonyl-phenol (including isomers), propyl-heptyl-decyl-phenol (including isomers), propyl-heptyl-dodecyl-phenol (including isomers), propyl-heptyl-phenyl-phenol (including isomers), propyl-heptyl-phenoxyphenol (including isomers), propyl-heptyl-cumyl-phenol (including isomers), propyl-octyl-nonyl-phenol (including isomers), propyl-octyl-decyl-phenol (including isomers), propyl-octyl-dodecyl-phenol (including isomers), propyl-octyl-phenyl-phenol (including isomers), propyl-octyl-phenoxyphenol (including isomers), propyl-octyl-cumyl-phenol (including isomers), propyl-nonyl-decyl-phenol (including isomers), propyl-nonyl-dodecyl-phenol (including isomers), propyl-nonyl-phenyl-phenol (including isomers), propyl-nonyl-phenoxyphenol (including isomers), propyl-nonyl-cumyl-phenol (including isomers), propyl-decyl-dodecyl-phenol (including isomers), propyl-decyl-phenyl-phenol (including isomers), propyl-decyl-phenoxyphenol (including isomers), propyl-decyl-cumyl-phenol (including isomers), propyl-dodecyl-phenyl-phenol (including isomers), propyl-dodecyl-phenoxyphenol (including isomers), cumyl-phenol (including isomers) propyl-phenyl-phenoxyphenol (including isomers), propyl-phenyl-cumyl-phenol (including isomers), butyl-pentyl-hexyl-phenol (including isomers), butylpentyl-heptyl-phenol (including isomers), butyl-pentyl-octyl-phenol (including isomers), butyl-pentyl-nonyl-phenol (including isomers), butyl-pentyl-decyl-phenol (including isomers), butyl-pentyl-dodecyl-phenol (including isomers), butyl-pentyl-phenyl-phenol (including isomers), butyl-pentyl-phenoxyphenol (including isomers), butyl-pentyl-cumyl-phenol (including isomers), butyl-hexyl-heptyl-phenol (including isomers), butyl-hexyl-octyl-phenol (including isomers), butyl-hexyl-nonyl-phenol (including isomers), butyl-hexyl-decyl-phenol (including isomers), butyl-hexyl-dodecyl-phenol (including isomers), butyl-hexyl-phenyl-phenol (including isomers), butyl-hexyl-phenoxyphenol (including isomers), butyl-hexyl-cumyl-phenol (including isomers), butyl-heptyl-octyl-phenol (including isomers), butyl-heptyl-nonyl-phenol (including isomers), butyl-heptyl-decyl-phenol (including isomers), butyl-heptyl-dodecyl-phenol (including isomers), butyl-heptyl-phenyl-phenol (including isomers), butyl-heptyl-phenoxyphenol (including isomers), butyl-heptyl-cumyl-phenol (including isomers), butyl-octyl-nonyl-phenol (including isomers), butyl-octyl-decyl-phenol (including isomers), butyl-octyl-dodecyl-phenol (including isomers), butyl-octyl-phenyl-phenol (including isomers), butyl-octyl-phenoxyphenol (including isomers), butyl-octyl-cumyl-phenol (including isomers), butyl-nonyl-decyl-phenol (including isomers), butyl-nonyl-dodecyl-phenol (including isomers), butyl-nonyl-phenyl-phenol (including isomers), butyl-nonyl-phenoxyphenol (including isomers), butyl-nonyl-cumyl-phenol (including isomers), butyl-decyl-dodecyl-phenol (including isomers), butyl-decyl-phenyl-phenol (including isomers), butyl-decyl-phenoxyphenol (including isomers), butyl-decyl-cumyl-phenol (including isomers), butyl-dodecyl-phenol (including isomers), butyl-dodecyl-phenyl-phenol (including isomers), butyl-dodecyl-phenoxyphenol (including isomers), butyl-dodecyl-cumyl-phenol (including isomers), butyl-phenyl-phenol (including isomers), butyl-phenyl-phenoxyphenol (including isomers), butyl-phenyl-cumyl-phenol (including isomers), pentyl-hexyl-heptyl-phenol (including isomers), pentyl-hexyl-octyl-phenol (including isomers), pentyl-hexyl-nonyl-phenol (including isomers), pentyl-hexyl-decyl-phenol (including isomers), pentyl-hexyl-dodecyl-phenol (including isomers), pentyl-hexyl-phenyl-phenol (including isomers), pentyl-hexyl-phenoxyphenol (including isomers), pentyl-hexyl-cumyl-phenol (including isomers), pentyl-heptyl-octyl-phenol (including isomers), pentyl-heptyl-nonyl-phenol (including isomers), pentyl-heptyl-decyl-phenol (including isomers), pentyl-heptyl-dodecyl-phenol (including isomers), pentyl-heptyl-phenyl-phenol (including isomers), pentyl-heptyl-phenoxyphenol (including isomers), pentyl-heptyl-cumyl-phenol (including isomers), pentyl-octyl-nonyl-phenol (including isomers), pentyl-octyl-decyl-phenol (including isomers), pentyl-octyl-dodecyl-phenol (including isomers), pentyl-octyl-phenyl-phenol (including isomers), pentyl-octyl-phenoxyphenol (including isomers), pentyl-octyl-cumyl-phenol (including isomers), pentyl-nonyl-decyl-phenol (including isomers), pentyl-nonyl-dodecyl-phenol (including isomers), pentyl-nonyl-phenyl-phenol (including isomers), pentyl-nonyl-phenoxyphenol (including isomers), pentyl-nonyl-cumyl-phenol (including isomers), pentyl-decyl-dodecyl-phenol (including isomers), pentyl-decyl-phenyl-phenol (including isomers), pentyl-decyl-phenoxyphenol (including isomers), pentyl-decyl-cumyl-phenol (including isomers), pentyl-decyl-dodecyl-phenol (including isomers), pentyl-decyl-phenyl-phenol (including isomers), pentyl-decyl-phenoxyphenol (including isomers), pentyl-decyl-cumyl-phenol (including isomers), pentyl-dodecyl-phenyl-phenol (including isomers), pentyl-dodecyl-phenoxyphenol (including isomers), pentyl-dodecyl-cumyl-phenol (including isomers), pentyl-phenyl-phenoxyphenol (including isomers), pentyl-phenyl-cumyl-phenol (including isomers), hexyl-heptyl-octyl-phenol (including isomers), hexyl-heptyl-nonyl-phenol (including isomers), hexyl-heptyl-decyl-phenol (including isomers), hexyl-heptyl-dodecyl-phenol (including isomers), hexyl-heptyl-phenyl-phenol (including isomers), hexyl-heptyl-phenoxyphenol (including isomers), hexyl-heptyl-cumyl-phenol (including isomers), hexyl-octyl-nonyl-phenol (including isomers), hexyl-octyl-decyl-phenol (including isomers), hexyl-octyl-dodecyl-phenol (including isomers), hexyl-octyl-phenyl-phenol (including isomers), hexyl-octyl-phenoxyphenol (including isomers), hexyl-octyl-cumyl-phenol (including isomers), hexyl-nonyl-decyl-phenol (including isomers), hexyl-nonyl-dodecyl-phenol (including isomers), hexyl-nonyl-phenyl-phenol (including isomers), hexyl-nonyl-phenoxyphenol-decyl-dodecyl-phenol (including isomers), hexyl-decyl-phenyl-phenol (including isomers), hexyl-decyl-phenoxyphenol (including isomers), hexyl-decyl-cumyl-phenol (including isomers), hexyl-dodecyl-phenyl-phenol (including isomers), hexyl-dodecyl-phenoxyphenol (including isomers), hexyl-dodecyl-cumyl-phenol (including isomers), hexyl-phenyl-phenoxyphenol (including isomers), hexyl-phenyl-cumyl-phenol (including isomers), heptyl-octyl-nonyl-phenol (including isomers), heptyl-octyl-decyl-phenol (including isomers), heptyl-octyl-dodecyl-phenol (including isomers), heptyl-octyl-phenyl-phenol (including isomers), heptyl-octyl-phenoxyphenol (including isomers), heptyl-octyl-cumyl-phenol (including isomers), heptyl-nonyl-decyl-phenol (including isomers), heptyl-nonyl-dodecyl-phenol (including isomers), heptyl-nonyl-phenyl-phenol (including isomers), heptyl-nonyl-phenoxyphenol (including isomers), heptyl-nonyl-cumyl-phenol (including isomers), heptyl-decyl-dodecyl-phenol (including isomers), heptyl-decyl-phenyl-phenol (including isomers), heptyl-decyl-phenoxyphenol (including isomers), heptyl-decyl-cumyl-phenol (including isomers), heptyl-dodecyl-phenyl-phenol (including isomers), heptyl-dodecyl-phenoxyphenol (including isomers), heptyl-dodecyl-cumyl-phenol (including isomers), heptyl-phenyl-phenoxyphenol (including isomers), heptyl-phenyl-cumyl-phenol (including isomers), octyl-nonyl-decyl-phenol (including isomers), octyl-nonyl-dodecyl-phenol (including isomers), octyl-nonyl-phenyl-phenol (including isomers), octyl-nonyl-phenoxyphenol (including isomers), octyl-nonyl-cumyl-phenol (including isomers), octyl-decyl-dodecyl-phenol (including isomers), octyl-decyl-phenyl-phenol (including isomers), octyl-decyl-phenoxyphenol (including isomers), octyl-decyl-cumyl-phenol (including isomers), octyl-dodecyl-phenyl-phenol (including isomers), octyl-dodecyl-phenoxyphenol (including isomers), octyl-dodecyl-cumyl-phenol (including isomers), octyl-dodecyl-phenyl-phenol (including isomers), octyl-dodecyl-phenoxyphenol (including isomers), octyl-dodecyl-cumyl-phenol (including isomers), octyl-phenyl-phenoxyphenol (including isomers), octyl-phenyl-cumyl-phenol (including isomers), nonyl-decyl-dodecyl-phenol (including isomers), nonyl-decyl-phenyl-phenol (including isomers), nonyl-decyl-phenoxyphenol (including isomers), nonyl-decyl-cumyl-phenol (including isomers), nonyl-dodecyl-phenyl-phenol (including isomers), nonyl-dodecyl-phenoxyphenol (including isomers), nonyl-dodecyl-cumyl-phenol (including isomers), nonyl-phenyl-phenoxyphenol (including isomers), nonyl-phenyl-cumyl-phenol (including isomers), decyl-dodecyl-phenyl-phenol (including isomers), decyl-dodecyl-phenoxyphenol (including isomers), decyl-dodecyl-cumyl-phenol (including isomers), decyl-phenyl-phenoxyphenol (including isomers), decyl-phenyl-cumyl-phenol (including isomers), dodecyl-phenyl-phenoxyphenol (including isomers), dodecyl-phenyl-cumyl-phenol (including isomers) and phenyl-phenoxy-cumyl-phenol (including isomers).

In addition, the standard boiling point of the monovalent aromatic hydroxy compound is preferably lower than the standard boiling point of the divalent aromatic hydroxy compound produced according to the process of the present embodiment. Although there are cases on which a monovalent aromatic hydroxy compound having a standard boiling point higher than the standard boiling point of the divalent aromatic hydroxy compound can be used, in such cases, when the resulting isocyanate compound and the divalent aromatic hydroxy compound are extracted from a thermal decomposition reactor in the form of a gaseous phase component in a carbamic acid ester thermal decomposition step to be described later, there is the risk of a polymeric polycarbamic acid ester, formed by an addition reaction between the isocyanate and the divalent aromatic hydroxy compound, adhering to the walls of the reactor, thereby making this undesirable. There are no particular limitations on the combination of the monovalent aromatic hydroxy compound and the divalent aromatic hydroxy compound, and the combination thereof can be arbitrarily selected.

There are no particular limitations on the reactor used in the reaction, and a known reactor can be used. For example, conventionally known reactors such as a stirring tank, pressurized stirring tank, vacuum stirring tank or column reactor can be suitably combined and used. There are also no particular limitations on the material of the reactor, and known materials can be used. Examples of materials that can be used may include glass, stainless steel, carbon steel, Hastelloy, materials comprising a base material lined with glass, and those provided with a Teflon coating. Since there are cases in which corrosion caused by the amine compound and/or aromatic hydroxy compound can become remarkable depending on the step and conditions, in such cases, the reactor may be made of glass, have a glass lining or have a Teflon coating, or a Hastelloy reactors can be suitably selected.

The amine compound having primary amino groups is preferably supplied in a liquid form to the reactor where the reaction between the aromatic hydroxy compound and the amine compound having primary amino groups is carried out. In general, many of the previously listed examples of amine compounds are solids at normal temperatures (for example, 20° C.), and although these amine compounds can be supplied in the liquid form by heating to a temperature higher than the melting point thereof, since there are cases in which side reactions such as a thermal denaturation reaction occurs due to heating if the amine compound is supplied at an excessively high temperature, the amine compound is preferably supplied in the liquid form at a comparatively low temperature as a mixture with the above-mentioned aromatic hydroxy compound and water.

<Carbamic Acid Ester and Aromatic Hydroxy Compound Obtained by Reaction>

A mixture containing a carbamic acid ester and a compound having an aromatic hydroxyl group, which are originated from the aromatic polycarbonate, is obtained by the reaction between the aromatic polycarbonate resin and the amine compound having primary amino groups as previously described. The following provides an explanation of the carbamic acid ester and the compound having an aromatic hydroxyl group.

In the present embodiment, an aromatic polycarbonate compound is used having a repetitive unit represented by the following formula (19):

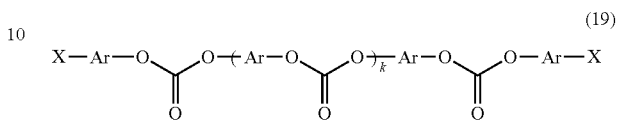

(wherein Ar represents a divalent aromatic group having 6 to 20 carbon atoms, X represents a terminal end group in a form of a residue of a chain terminator used when producing the aromatic polycarbonate, or a hydroxyl group, and k represents an integer of 0 or more); and a compound represented by the following formula (20) is used for the amine compound having primary amino groups:

(wherein $R^1$ represents a group selected from the group consisting of aliphatic groups having 1 to 20 carbon atoms and aromatic groups having 6 to 20 carbon atoms, the above groups contain an atom selected from carbon and oxygen atoms, and have an atomic number equal to n, and n represents an integer of from 2 to 10).

The compound having an aromatic hydroxyl group, which is originated from the aromatic polycarbonate obtained by carrying out the above reaction, is a compound represented by the following formula (21) having a structure in which a hydroxyl group (OH) is added to the Ar group constituting the main chain skeleton of the repetitive unit:

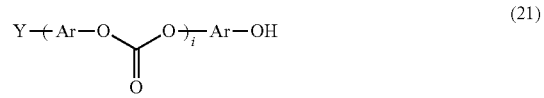

(wherein Ar represents a group as previously defined, Y represents a terminal end group X or —OH group as previously defined, and i represents an integer of from 0 to k).

On the other hand, the carbamic acid ester originated from the aromatic polycarbonate obtained by the above reaction is a compound represented by the following formula (22):

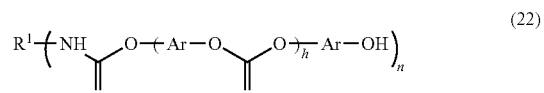

(wherein, Ar represents a group originated from the aromatic polycarbonate as previously defined, $R^1$ represents a group originated from the amine compound as previously defined, h represents an integer of from 0 to k, and n represents a value as previously defined).

In addition, in the reaction between the aromatic polycarbonate and the amine compound, in the case of using a monovalent aromatic hydroxy compound represented by the following formula (23) as previously described as a reaction solvent:

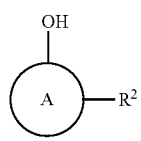
(23)

(wherein ring A represents an aromatic hydrocarbon ring which has 6 to 20 carbon atoms and which may have a substituent, and the ring A may be a monocyclic or heterocyclic ring, and $R^2$ represents an aliphatic group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the above groups contain an atom selected from the group consisting of carbon, oxygen and nitrogen atoms, and $R^2$ may also bond with A to form a ring structure);

a transesterification reaction occurs between the aromatic polycarbonate and the monovalent aromatic hydroxy compound yielding a cleavaged product of the aromatic polycarbonate as represented by the following formula (24) or formula (25):

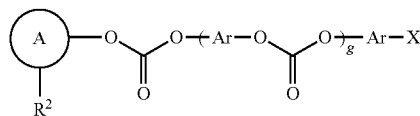
(24)

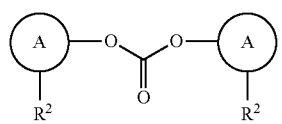
(25)

(wherein Ar represents a group originated from the aromatic polycarbonate as previously defined, A and $R^2$ represent groups originated from the monovalent aromatic hydroxy compound as previously defined, X represents the terminal end group X or —OH group as previously defined, and g represents an integer of from 0 to k).

In such cases, a compound represented by the following formula (26) may be contained in the form of a carbamic acid ester:

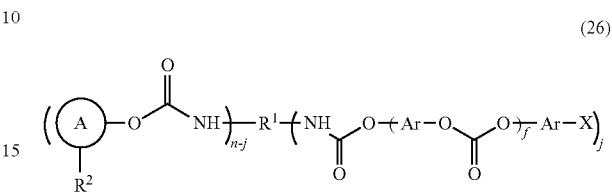
(26)

(wherein $R^1$ represents a group originated from the amine compound as previously defined, A and $R^2$ represent groups originated from the monovalent aromatic hydroxy compound as previously defined, X represents the terminal end group X or —OH group as previously defined, f represents an integer of from 0 to k, j represents an integer of from 1 to n, and n represents a value as previously defined).

The following provides a more detailed explanation.

In the case of carrying out the reaction using the aromatic polycarbonate in which the divalent aromatic hydroxy compound represented by the structure $Ar(OH)_2$, in which two hydroxyl groups are added to the Ar group in formula (19) above, is bisphenol A, and the terminal end group X is at least one group selected from the group consisting of a phenoxy group, p-tert-butylphenoxy group and hydroxyl group, is used for the aromatic polycarbonate, and a divalent amine compound represented by the following formula (27) is used for the amine compound:

$$H_2N-R^3-NH_2 \qquad (27)$$

(wherein $R^3$ represents a group selected from the group consisting of aliphatic groups having 1 to 20 carbon atoms and aromatic groups having 6 to 20 carbon atoms, the above groups contain an atoms selected from the group consisting of carbon atoms and oxygen atoms);

a carbamic acid ester produced according to the process of the present embodiment is a compound represented by the following formula (28):

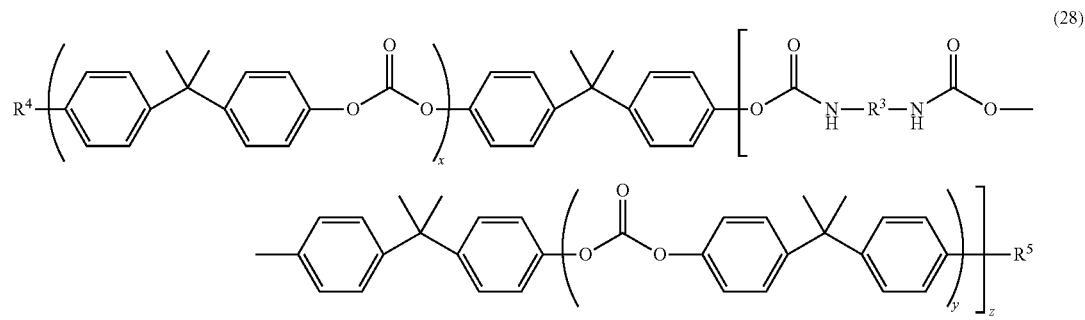
(28)

(wherein R³ represents a group selected from the group consisting of aliphatic groups having 1 to 20 carbon atoms and aromatic groups having 6 to 20 carbon atoms, the above groups contain an atom selected from the group consisting of carbon atoms and oxygen atoms, and each of R⁴ and R⁵ independently represents a substituent selected from the group represented by the following formula (29):

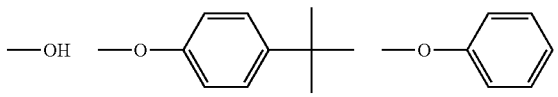

(29)

(wherein each of x, y and z independently represents an integer of 0 or more).

The R³ in formula (29) above is a group originated from the above-mentioned amine compound, and is preferably a group originated from a linear hydrocarbon group such as methylene, dimethylene, trimethylene, tetramethylene, pentamethylene, hexamethylene or octamethylene; unsubstituted acyclic hydrocarbon groups such as cyclopentane, cyclohexane, cycloheptane, cyclooctane or bis(cyclohexyl)alkane; alkyl-substituted cyclohexanes such as methylcyclopentane, ethylcyclopentane, methylcyclohexane (including isomers), ethylcyclohexane (including isomers), propylcyclohexane (including isomers), butylcyclohexane (including isomers), pentylcyclohexane (including isomers) or hexylcyclohexane (including isomers); dialkyl-substituted cyclohexanes such as dimethylcyclohexane (including isomers), diethylcyclohexane (including isomers) or dibutylcyclohexane (including isomers); trialkyl-substituted cyclohexanes such as 1,5,5-trimethylcyclohexane, 1,5,5-triethylcyclohexane, 1,5,5-tripropylcyclohexane (including isomers) or 1,5,5-tributylcyclohexane (including isomers); monoalkyl-substituted benzenes such as toluene, ethylbenzene or propylbenzene; dialkyl-substituted benzenes such as xylene, diethylbenzene or dipropylbenzene; and aromatic hydrocarbons such as diphenylalkane or benzene. Particularly preferable examples may include hexamethylene, phenylene, diphenylmethane, toluene, cyclohexane, xylene, methylcyclohexane, isophorone and cyclohexylmethane groups. Namely, groups originated from aliphatic diamines such as hexamethylene diamine, 4,4'-methylenebis(cyclohexylamine) (including isomers), cyclohexane diamine (including isomers) or 3-aminomethyl-3,5,5-trimethylcyclohexyl amine (including isomers); and aromatic diamines such as phenylene diamine (including isomers), toluene diamine (including isomers) or 4,4'-methylenedianiline (including isomers) are preferable, while groups originated from aliphatic diamines such as hexamethylene diamine, 4,4'-methylenebis(cyclohexylamine) (including isomers), cyclohexane diamine (including isomers) or 3-aminomethyl-3,5,5-trimethylcyclohexyl amine (including isomers) are particularly preferable, while groups originated from hexamethylene diamine, 4,4'-methylenebis(cyclohexylamine) or 3-aminomethyl-3,5,5-trimethylcyclohexyl amine are more preferable.

The carbamic acid ester is preferably used as a raw material for producing an isocyanate compound in particular. Although the details thereof will be described later, an isocyanate and divalent aromatic hydroxy compound (bisphenol A) are formed by subjecting the carbamic acid ester to a thermal decomposition reaction. The bisphenol A unexpectedly demonstrates the effect of improving the yield of isocyanate by inhibiting thermal denaturation of the carbamic acid ester represented by formula (8) above. In addition, since the boiling point of bisphenol A is higher than that of the isocyanate compound formed, the isocyanate can be recovered in the form of a gaseous phase component while the bisphenol A can be recovered in the form of a liquid phase component, thereby facilitating separation of the thermal decomposition products. Moreover, since the bisphenol A dissolves by-products from the thermal denaturation reaction as represented by, for example, the formulas (8) and/or (9) and/or (10) above attributable to the carbamic acid ester and/or the thermal decomposition product in the form of the isocyanate, by-products from the thermal denaturation reaction can be expelled from the reactor where the thermal decomposition reaction is carried out in the form of a solution of bisphenol A, thereby making it possible to prevent adherence and accumulation on the walls of the reactor while also enabling operation of the isocyanate production process based on a thermal decomposition reaction over a long period of time.

<Transfer of Reaction Liquid>

The reaction liquid containing carbamic acid ester produced by the process according to the present embodiment is preferably removed from the reactor where the reaction was carried out and transferred to a reaction where the thermal decomposition reaction is carried out on the carbamic acid ester (to be referred to as "the thermal decomposition reactor") followed by carrying out the thermal decomposition reaction on the carbamic acid ester. In this manner, by using separator reactors for the reactor where the carbamic acid ester is produced and the thermal decomposition reactor, a suitable reactor can be selected for each reaction and the reaction conditions can be flexibly set, thereby making it possible to enhance the yield of each reaction.

Since these carbamic acid esters easily form intermolecular hydrogen bonds by bonding urethane constituting the carbamic acid esters, they frequently have a high melting point. In the transfer of such carbamic acid esters, for example, a solid carbamic acid ester can be transferred after subjecting to excipiation treatment such as by crushing or forming into pellets. However, in the case of transferring a solid carbamic acid ester that has been subjected to excipiation treatment, there are many cases in which a complex apparatus for stably transferring a fixed amount of carbamic acid ester is required or a step is required for unifying the form of the carbamic acid ester within a certain range is required in cases of frequent clogging of the transfer line or variations in the form of the carbamic acid ester. Thus, the carbamic acid ester is preferably supplied to the thermal decomposition reactor in a liquid form.

The method used to supply the carbamic acid ester to the thermal decomposition reactor in the liquid form can preferably employ a method in which it is supplied in the form of a reaction mixture obtained by reaction of the aromatic polycarbonate and the amine compound having primary amino groups.

The inventors of the present invention unexpectedly found that when the carbamic acid ester is transferred in the form of a mixture with an aromatic hydroxy compound, reductions in carbamic acid ester caused by thermal denaturation of the carbamic acid ester and the like as well as decreases in yield of the isocyanate compound can be inhibited. Although the reason for demonstrating this effect is uncertain, the inventors of the present invention presumed that, in a reaction that forms urea bonds as represented by the formula (8) above, as a result of urethane bonds (—NHCOO—) of the carbamic acid ester and the aromatic hydroxy compound contained in the reaction mixture forming hydrogen bonds, since the urethane bonds are formed in a state in which it is difficult for them to approach each other, it is difficult for the reaction resulting in the formation of urea bonds to occur.

There are no particular limitations on the method used to obtain a mixture of the carbamic acid ester and the aromatic hydroxy compound, and for example, the carbamic acid ester obtained by the reaction between the aromatic polycarbonate and the amine compound having primary amino groups as previously described may be separated and recovered by the known method such as crystallization, distillative separation or membrane separation followed by mixing the carbamic acid ester and the aromatic hydroxy compound. In addition, the aromatic hydroxy compound may be added and mixed with a mixture containing the carbamic acid ester obtained by reacting the aromatic polycarbonate and the amine compound having primary amino groups.

Alternatively, a reaction mixture containing the carbamic acid ester and the aromatic hydroxy compound, obtained by carrying out the reaction between the aromatic polycarbonate and the amine compound having primary amino groups as described above using the aromatic hydroxy compound as a reaction solvent, may be used directly. Since this method enables the reaction mixture to be transferred directly, the process is simplified, thereby making this more preferable.

The transfer of the mixture is preferably carried out within a temperature range of from 10° C. to 180° C., more preferably within a range of from 70° C. to 170° C. and even more preferably within a range of from 100° C. to 150° C. If the temperature is excessively high, the effect of the aromatic hydroxy compound of inhibiting thermal denaturation of the carbamic acid ester tends to be difficult to obtain, while on the other hand, if the temperature is excessively low, the viscosity of the mixture increases, which may cause problems during transfer.

<Thermal Decomposition of Carbamic Acid Ester>

The following provides an explanation of the production of the isocyanate and divalent aromatic hydroxy compound by thermal decomposition of the carbamic acid ester.

The thermal decomposition reaction of the present embodiment is a reaction for forming the corresponding isocyanate compound from the carbamic acid ester. In particular, the divalent aromatic hydroxy compound is formed simultaneous to the isocyanate from a carbamic acid ester in which h and g are both 0 in the above-mentioned formula (22) or formula (26).

The reaction temperature is generally within a range of from 100 to 300° C., and although a high temperature is preferable to increase the reaction rate, on the other hand, since there are cases in which side reactions as previously described may be induced at high temperatures depending on the carbamic acid ester and/or product in the form of the isocyanate compound, the reaction temperature is preferably within a range of from 150 to 250° C. A known cooling apparatus or heating apparatus may be installed to maintain a constant reaction temperature. In addition, although varying according to the types of compounds used and the reaction temperature, the reaction pressure is such that the reaction may be carried out at decreased pressure, normal pressure or increased pressure, and the reaction is generally carried out within a range of from 20 to $1 \times 10^6$ Pa. There are no particular limitations on the reaction time (residence time in the case of a continuous process), and is generally within a range of from 0.001 to 100 hours, preferably within a range of from 0.005 to 50 hours and more preferably within a range of from 0.01 to 10 hours.

A catalyst is preferably not used in the present embodiment. Although the thermal decomposition reaction may be promoted by using a catalyst, this is not preferable since there are many cases in which there is increased susceptibility to the occurrence of side reactions attributable to the carbamic acid ester and/or product isocyanate compound as previously described.

The above-mentioned side reactions may occur in the case a carbamic acid ester is held for a long time at a high temperature. In addition, the isocyanate compound formed by the thermal decomposition reaction may also cause side reactions as previously described. Thus, the time during which the carbamic acid ester and the isocyanate compound are held at a high temperature is preferably as short as possible, and the thermal decomposition reaction is preferably carried out with a continuous process. A continuous process refers to a process in which the mixture containing the carbamic acid ester is continuously supplied to the reactor and subjected to the thermal decomposition reaction, and the resulting isocyanate compound and divalent aromatic hydroxy compound are continuously extracted from the thermal decomposition reactor. In this continuous process, low boiling point components formed by thermal decomposition of carbamic acid ester are preferably recovered from the top of the thermal decomposition reactor in the form of a gaseous phase component, while the remainder is recovered from the bottom of the thermal decomposition reactor in the form of a liquid phase component. Here, low boiling point components include the isocyanate compound and/or the reaction solvent in the form of the monovalent aromatic hydroxy compound. Although all compounds present in the thermal decomposition reactor can be recovered in the form of a gaseous phase component, the presence of a liquid component in the thermal decomposition reactor has the effect of preventing adherence and accumulation of polymeric compounds on the thermal decomposition reactor by dissolving polymeric compounds formed by side reactions induced by the carbamic acid ester and/or isocyanate compound. Although an isocyanate compound and divalent aromatic hydroxy compound are formed by thermal decomposition of the carbamic acid ester, at least one of these compounds is recovered in the form of a gaseous phase component. Although which of these compounds is recovered in the form of a gaseous phase component is dependent on the conditions of the thermal decomposition reaction, from the viewpoint of obtaining a highly pure isocyanate compound, the isocyanate compound is preferably extracted in the form of a gaseous phase component. In the case the carbamic acid ester is subjected to the thermal decomposition reaction after being supplied to the thermal decomposition reactor in the form of a mixture with the aromatic hydroxy compound as previously described, although whether the aromatic hydroxy compound is recovered as a gaseous phase component or a liquid phase component depends on the conditions of the thermal decomposition reaction, it is preferably recovered in the form of a gaseous phase component from the viewpoint of avoiding the carbamic acid ester being formed by reacting an isocyanate compound and the aromatic hydroxy compound, and the carbamic acid ester being recovered together with the isocyanate.

For example, a method can be employed whereby the isocyanate compound formed by the thermal decomposition reaction and the aromatic hydroxy compound are recovered in the form of a gaseous phase component, and a liquid component is recovered containing the divalent aromatic hydroxy compound and/or the carbamic acid ester. In this method, the isocyanate compound and the aromatic hydroxy compound may also be recovered separately in the thermal decomposition reactor. The gaseous phase component containing the recovered isocyanate compound is preferably supplied to a distillation apparatus for separating and purifying the isocyanate compound in the gaseous phase. Although the gaseous phase component containing the recovered isocyanate compound can be supplied to a distillation apparatus after being transformed to the liquid phase by a condenser and the like, there are many cases in which the apparatus becomes complex and the amount of energy used increases, thereby making this undesirable. On the other hand, the liquid phase component containing the divalent aromatic hydroxy compound and/or the carbamic acid ester is recovered from the bottom of the thermal decomposition reactor, and in the case the liquid phase component contains carbamic acid ester, all or a portion of the liquid phase component is supplied to the top of the thermal decomposition reactor after which the carbamic acid ester is resubjected to the thermal decomposition reaction. The top of the thermal decomposition reactor as referred to here indicates, for example, the level of the second plate or higher from the bottom in terms of the number of theoretical plates in the case the thermal decomposition reactor is a distillation column, and in the case the thermal decomposition reactor is a thin film distiller, indicates the portion higher than the heated transfer surface. When supplying all or a portion of the liquid phase component to the top of the thermal decomposition reactor, the liquid phase component is transferred while preferably maintaining at 10 to 300° C., more preferably 30° C. to 250° C. and even more preferably 50° C. to 120° C. In addition, when re-supplying all or a portion of the liquid phase component to the thermal decomposition reactor, this may be carried out after having removed all or a portion of the divalent aromatic hydroxy compound contained in the liquid phase component.

In addition, a method can also be employed whereby, for example, the isocyanate compound formed by the thermal decomposition reaction is recovered in the form of a gaseous phase component, while a liquid phase component is recovered containing the aromatic hydroxy compound, divalent aromatic hydroxy compound and/or carbamic acid ester. The gaseous phase component containing the recovered isocyanate compound is preferably supplied in the gaseous phase to a distillation apparatus for separating and purifying the isocyanate. Although the gaseous phase component containing the recovered isocyanate compound can be supplied to a distillation apparatus after transforming to a liquid phase by a condenser and the like, there are many cases in which the apparatus becomes complex and the amount of energy used increases, thereby making this undesirable. On the other hand, the liquid phase component containing the aromatic hydroxy compound, divalent aromatic hydroxy compound and/or carbamic acid ester is recovered from the bottom of the thermal decomposition reactor, and in the case the liquid phase component contains carbamic acid ester, all or a portion of the liquid phase component is preferably supplied to the top of the thermal decomposition reactor after which the carbamic acid ester is resubjected to the thermal decomposition reaction. When supplying all or a portion of the liquid phase component to the top of the thermal decomposition reactor, the liquid phase component is transferred while preferably maintaining at 10° C. to 300° C., more preferably 30° C. to 250° C. and even more preferably 50° C. to 120° C. In addition, when re-supplying all or a portion of the liquid phase component to the thermal decomposition reactor, this may be carried out after having removed all or a portion of the divalent aromatic hydroxy compound and after removing all or a portion of the aromatic hydroxy compound from the liquid phase component.

Although previously described, the liquid phase component is preferably recovered from the bottom of the thermal decomposition reactor in the thermal decomposition reaction. This is because, by allowing the liquid phase component to be present in the thermal decomposition reactor, the liquid phase component dissolves polymeric by-products formed by side reactions induced by the carbamic acid ester and/or isocyanate, thereby enabling these by-products to be expelled from the thermal decomposition reactor in the form of a liquid phase component and resulting in the effect of reducing adherence and accumulation of the polymeric compounds in the thermal decomposition reactor.

In the case carbamic acid ester is contained in the liquid phase component, although all or a portion of the liquid phase component is supplied to the top of the thermal decomposition reactor and the carbamic acid ester is resubjected to the thermal decomposition reaction, repetition of this step may result in the accumulation of polymeric by-products in the liquid phase component. In such cases, all or a portion of the liquid phase component can be removed from the reaction system, thereby reducing accumulation of polymeric by-products or maintaining at a fixed concentration thereof.

The aromatic hydroxy compound obtained in the above process can be recovered by separation and reused as a reaction solvent during production of the carbamic acid ester and/or as a solvent used during transfer of the mixture containing the carbamic acid ester and/or as a solvent in the carbamic acid ester thermal decomposition reaction.

In addition, the isocyanate recovered by the above process can be purified by the known method such as distillative separation or membrane separation. In addition, the divalent aromatic hydroxy compound recovered after going through the above process can be purified by the method such as distillative separation, film separation or crystallization.

Although there are no particular limitations on the type of the thermal decomposition reactor, the known distillation apparatus is used preferably in order to efficiency recover the gaseous phase component. Various known methods are used for such a reactor, examples of which may include types using reactors containing a distillation column, multistage distillation column, multitubular reactor, continuous multistage distillation column, packed column, thin film evaporator, reactor provided with a support inside, forced circulation reactor, falling film evaporator, falling drop evaporator, and types using combinations thereof. Methods using a tubular reactor are preferable from the viewpoint of rapidly removing low boiling point components from the reaction system, while a structure having a large gas-liquid contact area is preferable for being able to rapidly transfer the low boiling point components formed to the gaseous phase.

Although the material of the thermal decomposition reactor and lines may be any known material provided it does not have a detrimental effect on the carbamic acid ester, divalent aromatic hydroxy compound or isocyanate and the like, materials such as SUS304, SUS316 or SUS316L are inexpensive and can therefore be used preferably.

<Cleaning of Thermal Decomposition Reactor>

In the present embodiment, there are cases in which the reaction liquid containing carbamic acid ester obtained by reacting the aromatic polycarbonate and the amine compound having primary amino groups contains polymeric side reaction products represented by, for example, the above-mentioned formula (8), (9) and (10). Since these side reaction products easily dissolve in the aromatic hydroxy compound in many cases, they are dissolved in the reaction liquid containing the aryl carbamate. However, if the majority of the aromatic hydroxy compound is extracted from the thermal decomposition reactor in the form of a gaseous phase component, the side reaction products end up precipitating in the thermal decomposition reactor and frequency adhere thereto.

When these compounds that have adhered to the thermal decomposition reactor accumulated to a certain degree, they may impair operation of the thermal decomposition reactor and make long-term operation difficult, thereby resulting in the need to disassemble and clean the thermal decomposition reactor.

The inventors of the present invention unexpectedly found that compound adhered to the thermal decomposition reactor easily dissolve in an aromatic hydroxy compound. On the basis of this finding, in the case side reaction product have adhered to the thermal decomposition reactor, the inventors of the present invention proposed and perfected a method for keeping the inside of the thermal decomposition reactor clean by cleaning the walls of the thermal decomposition reactor with an aromatic hydroxy compound to dissolve these side reaction products and remove them from the thermal decomposition reactor. As a result of employing this method, since the walls of the thermal decomposition reactor can be cleaned without having to disassemble and separately clean the thermal decomposition reactor, the downtime of the thermal decomposition reactor can be minimized, thereby resulting in high isocyanate production efficiency.

There are no particular limitations on the cleaning solvent provided it dissolves the polymeric by-products, and although an organic acid or inorganic acid may be used, organic acid is used preferably. Although examples of organic acids may include carboxylic acid, sulfonic acid, sulfinic acid, phenols, enols, thiophenols, imides, oximes and aromatic sulfonamides, carboxylic acid and phenols are used preferably. Examples of such compounds may include saturated or unsaturated aliphatic monocarboxylic acids such as formic acid, acetic acid, propionic acid, n-butyric acid, isobutyric acid, valeric acid, isovaleric acid, 2-methylbutanoic acid, pivalic acid, hexanoic acid, isocaproic acid, 2-ethylbutanoic acid, 2,2-dimethylbutanoic acid, heptanoic acid (including isomers), octanoic acid (including isomers), nonanoic acid (including isomers), decanoic acid (including isomers), undecanoic acid (including isomers), dodecanoic acid (including isomers), tetradecanoic acid (including isomers), hexadecanoic acid (including isomers), acrylic acid, crotonic acid, isocrotonic acid, vinyl acetate, methacrylic acid, angelic acid, tiglic acid, allyl acetate or undecenoic acid (including isomers); saturated or unsaturated aliphatic dicarboxylic acids such as oxalic acid, malonic acid, succinic acid, glutaric acid, adipic acid, heptane diacid (including isomers), octane diacid (including isomers), nonane diacid (including isomers), decane diacid (including isomers), maleic acid, fumaric acid, methylmaleic acid, methylfumaric acid, pentene diacid (including isomers), itaconic acid or allylmalonic acid; saturated or unsaturated aliphatic tricarboxylic acids such as 1,2,3-propane tricarboxylic acid, 1,2,3-propene tricarboxylic acid or 2,3-dimethylbutane-1,2,3-tricarboxylic acid; aromatic carboxylic acids such as benzoic acid, methylbenzoic acid (including isomers), ethylbenzoic acid (including isomers), propyl benzoic acid (including isomers), dimethylbenzoic acid (including isomers) or trimethylbenzoic acid (including isomers); aromatic dicarboxylic acids such as phthalic acid, isophthalic acid, terephthalic acid or methylisophthalic acid (including isomers); aromatic tricarboxylic acids such as hemimellitic acid, trimellitic acid or trimesinic acid; and aromatic hydroxy compounds such as phenol. Among these, aromatic hydroxy compounds are preferable in consideration of the solubility of the polymeric by-products and effects in the case of the cleaning solvent remaining in the thermal decomposition reactor. Examples of such aromatic hydroxy compounds may include mono-substituted phenols such as phenol, methylphenol (including isomers), ethylphenol (including isomers), propylphenol (including isomers), butylphenol (including isomers), pentylphenol (including isomers), hexylphenol (including isomers), heptylphenol (including isomers), octylphenol (including isomers), nonylphenol (including isomers), decylphenol (including isomers), dodecylphenol (including isomers), phenylphenol (including isomers), phenoxyphenol (including isomers) or cumylphenol (including isomers); di-substituted phenols such as dimethylphenol (including isomers), diethylphenol (including isomers), dipropylphenol (including isomers), dibutylphenol (including isomers), dipentyphenol (including isomers), dihexylphenol (including isomers), diheptylphenol (including isomers), dioctylphenol (including isomers), dinonylphenol (including isomers), didecylphenol (including isomers), didodecylphenol (including isomers), diphenylphenol (including isomers), diphenoxyphenol (including isomers), dicumylphenol (including isomers), methylethylphenol (including isomers), methylpropylphenol (including isomers), methylbutylphenol (including isomers), methylpentylphenol (including isomers), methylhexylphenol (including isomers), methylheptylphenol (including isomers), methyloctylphenol (including isomers), methylnonylphenol (including isomers), methyldecylphenol (including isomers), methyldodecylphenol (including isomers), methylphenylphenol (including isomers), methylphenoxyphenol (including isomers), methylcumylphenol (including isomers), ethylpropylphenol (including isomers), ethylbutylphenol (including isomers), ethylpentylphenol (including isomers), ethylhexylphenol (including isomers), ethylheptylphenol (including isomers), ethyloctylphenol (including isomers), ethylnonylphenol (including isomers), ethyldecylphenol (including isomers), ethyldodecylphenol (including isomers), ethylphenylphenol (including isomers), ethylphenoxyphenol (including isomers), ethylcumylphenol (including isomers), propylbutylphenol (including isomers), propylpentylphenol (including isomers), propylhexylphenol (including isomers), propylheptylphenol (including isomers), propyloctylphenol (including isomers), propylnonylphenol (including isomers), propyldecylphenol (including isomers), propyldodecylphenol (including isomers), propylphenylphenol (including isomers), propylphenoxyphenol (including isomers), propylcumylphenol (including isomers), butylpentylphenol (including isomers), butylhexylphenol (including isomers), butylheptylphenol (including isomers), butyloctylphenol (including isomers), butylnonylphenol (including isomers), butyldecylphenol (including isomers), butyldodecylphenol (including isomers), butylphenylphenol (including isomers), butylphenoxyphenol (including isomers), butylcumylphenol (including isomers), pentylhexylphenol (including isomers), pentylheptylphenol (including isomers), pentyloctylphenol (including isomers), pentylnonylphenol (including isomers), pentyldecylphenol (including isomers), pentyldodecylphenol (including isomers), pentylphenylphenol (including isomers), pentylphenoxyphenol (including isomers), pentylcumylphenol (including isomers), hexylheptylphenol (including isomers), hexyloctylphenol (including isomers), hexylnonylphenol (including isomers), hexyldecylphenol (including isomers), hexyldodecylphenol (including isomers), hexylphenylphenol (including isomers), hexylphenoxyphenol (including isomers), hexylcumylphenol (including isomers), heptyloctylphenol (including isomers), heptylnonylphenol (including isomers), heptyldecylphenol (including isomers), heptyldodecylphenol (including isomers), heptylphenylphenol (including isomers), heptylphenoxyphenol (including isomers), heptylcumylphenol (including isomers), octylnonylphenol (including isomers), octyldecylphenol (including isomers), octyldodecylphenol (including isomers), octylphenylphenol (including isomers), octylphenoxyphenol (including isomers), octylcumylphenol (including isomers), nonyldecylphenol (including isomers), nonyldodecylphenol (including isomers), nonylphenylphenol (including isomers), nonylphenoxyphenol (including isomers), nonylcumylphenol (including isomers), dodecylphenylphenol (including isomers), dodecylphenoxyphenol (including isomers) or dodecylcumylphenol (including isomers); and tri-substituted phenols such as trimethylphenol (including isomers), triethylphenol (including isomers), tripropylphenol (including isomers), tributylphenol (including isomers), tripentylphenol (including isomers), trihexylphenol (including isomers), triheptylphenol (including isomers), trioctylphenol (including isomers), trinonylphenol (including isomers), tridecylphenol (including isomers), tridodecylphenol (including isomers), triphenylphenol (including isomers), triphenoxyphenol (including isomers), tricumylphenol (including isomers), dimethylethylphenol (including isomers), dimethylpropylphenol (including isomers), dimethylbutylphenol (including isomers), dimethylpentylphenol (including isomers), dimethylhexylphenol (including isomers), dimethylheptylphenol (including isomers), dimethyloctylphenol (including isomers), dimethylnonylphenol (including isomers), dimethyldecylphenol (including isomers), dimethyldodecylphenol (including isomers), dimethylphenylphenol (including isomers), dimethylphenoxyphenol (including isomers), dimethylcumylphenol (including isomers), diethylmethylphenol (including isomers), diethylpropylphenol (including isomers), diethylbutylphenol (including isomers), diethylpentylphenol (including isomers), diethylhexylphenol (including isomers), diethylheptylphenol (including isomers), diethyloctylphenol (including isomers), diethylnonylphenol (including isomers), diethyldecylphenol (including isomers), diethyldodecylphenol (including isomers), diethylphenylphenol (including isomers), diethylphenoxyphenol (including isomers), diethylcumylphenol (including isomers), dipropylmethylphenol (including isomers), dipropylethylphenol (including isomers), dipropylbutylphenol (including isomers), dipropylpentylphenol (including isomers), dipropylhexylphenol (including isomers), dipropylheptylphenol (including isomers), dipropyloctylphenol (including isomers), dipropylnonylphenol (including isomers), dipropyldecylphenol (including isomers), dipropyldodecylphenol (including isomers), dipropylphenylphenol (including isomers), dipropylphenoxyphenol (including isomers), dipropylcumylphenol (including isomers), dibutylmethylphenol (including isomers), dibutylethylphenol (including isomers), dibutylpropylphenol (including isomers), dibutylpentylphenol (including isomers), dibutylhexylphenol (including isomers), dibutylheptylphenol (including isomers), dibutyloctylphenol (including isomers), dibutylnonylphenol (including isomers), dibutyldecylphenol (including isomers), dibutyldodecylphenol (including isomers), dibutylphenylphenol (including isomers), dibutylphenoxyphenol (including isomers), dibutylcumylphenol (including isomers), dipentylmethylphenol (including isomers), dipentylethylphenol (including isomers), dipentylpropylphenol (including isomers), dipentylbutylphenol (including isomers), dipentylhexylphenol (including isomers), dipentylheptylphenol (including isomers), dipentyloctylphenol (including isomers), dipentylnonylphenol (including isomers), dipentyldecylphenol (including isomers), dipentyldodecylphenol (including isomers), dipentylphenylphenol (including isomers), dipentylphenoxyphenol (including isomers), dipentylcumylphenol (including isomers), dihexylmethylphenol (including isomers), dihexylethylphenol (including isomers), dihexylpropylphenol (including isomers), dihexylbutylphenol (including isomers), dihexylpentylphenol (including isomers), dihexylheptylphenol (including isomers), dihexyloctylphenol (including isomers), dihexylnonylphenol (including isomers), dihexyldecylphenol (including isomers), dihexyldodecylphenol (including isomers), dihexylphenylphenol (including isomers), dihexylphenoxyphenol (including isomers), dihexylcumylphenol (including isomers), diheptylmethylphenol (including isomers), diheptylethylphenol (including isomers), diheptylpropylphenol (including isomers), diheptylbutylphenol (including isomers), diheptylpentylphenol (including isomers), diheptylhexylphenol (including isomers), diheptyloctylphenol (including isomers), diheptylnonylphenol (including isomers), diheptyldecylphenol (including isomers), diheptyldodecylphenol (including isomers), diheptylphenylphenol (including isomers), diheptylphenoxyphenol (including isomers), diheptylcumylphenol (including isomers), dioctylmethylphenol (including isomers), dioctylethylphenol (including isomers), dioctylpropylphenol (including isomers), dioctylbutylphenol (including isomers), dioctylpentylphenol (including isomers), dioctylhexylphenol (including isomers), dioctylheptylphenol (including isomers), dioctylnonylphenol (including isomers), dioctyldecylphenol (including isomers), dioctyldodecylphenol (including isomers), dioctylphenylphenol (including isomers), dioctylphenoxyphenol (including isomers), dioctylcumylphenol (including isomers), dinonylmethylphenol (including isomers), dinonylethylphenol (including isomers), dinonylpropylphenol (including isomers), dinonylbutylphenol (including isomers), dinonylpentylphenol (including isomers), dinonylhexylphenol (including isomers), dinonylheptylphenol (including isomers), dinonyloctylphenol (including isomers), dinonyldecylphenol (including isomers), dinonyldodecylphenol (including isomers), dinonylphenylphenol (including isomers), dinonylphenoxyphenol (including isomers), dinonylcumylphenol (including isomers), didecylmethylphenol (including isomers), didecylethylphenol (including isomers), didecylpropylphenol (including isomers), didecylbutylphenol (including isomers), didecylpentylphenol (including isomers), didecylhexylphenol (including isomers), didecylheptylphenol (including isomers), didecyloctylphenol (including isomers), didecylnonylphenol (including isomers), didecyldodecylphenol (including isomers), didecylphenylphenol (including isomers), didecylphenoxyphenol (including isomers), didecylcumylphenol (including isomers), didodecylmethylphenol (including isomers), didodecylethylphenol (including isomers), didodecylpropylphenol (including isomers), didodecylbutylphenol (including isomers), didodecylpentylphenol (including isomers), didodecylhexylphenol (including isomers), didodecylheptylphenol (including isomers), didodecyloctylphenol (including isomers), didodecylnonylphenol (including isomers), didodecyldecylphenol (including isomers), didodecyldodecylphenol (including isomers), didodecylphenylphenol (including isomers), didodecylphenoxyphenol (including isomers), didodecylcumylphenol (including isomers), diphenylmethylphenol (including isomers), diphenylethylphenol (including isomers), diphenylpropylphenol (including isomers), diphenylbutylphenol (including isomers), diphenylpentylphenol (including isomers), diphenylhexylphenol (including isomers), diphenylheptylphenol (including isomers), diphenyloctylphenol (including isomers), diphenylnonylphenol (including isomers), diphenyldecylphenol (including isomers), diphenyldodecylphenol (including isomers), diphenylphenoxyphenol (including isomers), diphenylcumylphenol (including isomers), diphenoxymethylphenol (including isomers), diphenoxyethylphenol (including isomers), diphenoxypropylphenol (including isomers), diphenoxybutylphenol (including isomers), diphenoxypentylphenol (including isomers), diphenoxyhexylphenol (including isomers), diphenoxyheptylphenol (including isomers), diphenoxyoctylphenol (including isomers), diphenoxynonylphenol (including isomers), diphenoxydecylphenol (including isomers), diphenoxydodecylphenol (including isomers), diphenoxyphenylphenol (including isomers), diphenoxycumylphenol (including isomers), dicumylmethylphenol (including isomers), dicumylethylphenol (including isomers), dicumylpropylphenol (including isomers), dicumylbutylphenol (including isomers), dicumylpentylphenol (including isomers), dicumylhexylphenol (including isomers), dicumylheptylphenol (including isomers), dicumyloctylphenol (including isomers), dicumylnonylphenol (including isomers), dicumyldecylphenol (including isomers), dicumyldodecylphenol (including isomers), dicumylphenylphenol (including isomers), dicumylphenoxyphenol (including isomers), methylethylpropylphenol (including isomers), methylethylbutylphenol (including isomers), methylethylpentylphenol (including isomers), methylethylhexylphenol (including isomers), methylethylheptylphenol (including isomers), methylethyloctylphenol (including isomers), methylethylnonylphenol (including isomers), methylethyldecylphenol (including isomers), methylethyldodecylphenol (including isomers), methylethylphenylphenol (including isomers), methylethylphenoxyphenol (including isomers), methylethylcumylphenol (including isomers), methylpropylbutylphenol (including isomers), methylpropylpentylphenol (including isomers), methylpropylhexylphenol (including isomers), methypropylheptylphenol (including isomers), methylpropyloctylphenol (including isomers), methylpropylnonylphenol (including isomers), methylpropyldecylphenol (including isomers), methylpropyldodecylphenol (including isomers), methylpropylphenylphenol (including isomers), methylpropylphenoxyphenol (including isomers), methylpropylcumylphenol (including isomers), methylbutylpentylphenol (including isomers), methylbutylhexylphenol (including isomers), methylbutylheptylphenol (including isomers), methylbutyloctylphenol (including isomers), methylbutylnonylphenol (including isomers), methylbutyldecylphenol (including isomers), methylbutyldodecylphenol (including isomers), methylbutylphenylphenol (including isomers), methylbutylphenoxyphenol (including isomers), methylbutylcumylphenol (including isomers), methylpentylhexylphenol (including isomers), methypentylheptylphenol (including isomers), methylpentyloctylphenol (including isomers), methylpentylnonylphenol (including isomers), methylpentyldecylphenol (including isomers), methylpentyldodecylphenol (including isomers), methylpentylphenylphenol (including isomers), methylpentylphenoxyphenol (including isomers), methylpentylcumylphenol (including isomers), methyhexylheptylphenol (including isomers), methylhexyloctylphenol (including isomers), methylhexylnonylphenol (including isomers), methylhexyldecylphenol (including isomers), methylhexyldodecylphenol (including isomers), methylhexylphenylphenol (including isomers), methylhexylphenoxyphenol (including isomers), methylhexylcumylphenol (including isomers), ethylpropylbutylphenol (including isomers), ethylpropylpentylphenol (including isomers), ethylpropylhexylphenol (including isomers), ethylpropylheptylphenol (including isomers), ethylpropyloctylphenol (including isomers), ethylpropylnonylphenol (including isomers), ethylpropyldecylphenol (including isomers), ethylpropyldodecylphenol (including isomers), ethylpropylphenylphenol (including isomers), ethylpropylphenoxyphenol (including isomers), ethylpropylcumylphenol (including isomers), ethylbutylphenol (including isomers), ethylbutylpentylphenol (including isomers), ethylbutylhexylphenol (including isomers), ethylbutylheptylphenol (including isomers), ethylbutyloctylphenol (including isomers), ethylbutylnonylphenol (including isomers), ethylbutyldecylphenol (including isomers), ethylbutyldodecylphenol (including isomers), ethylbutylphenylphenol (including isomers), ethylbutylphenoxyphenol (including isomers), ethylbutylcumylphenol (including isomers), ethylpentylhexylphenol (including isomers), ethylpentylheptylphenol (including isomers), ethylpentyloctylphenol (including isomers), ethylpentylnonylphenol (including isomers), ethylpentyldecylphenol (including isomers), ethylpentyldodecylphenol (including isomers), ethylpentylphenylphenol (including isomers), ethylpentylphenoxyphenol (including isomers), ethylpentylcumylphenol (including isomers), ethylhexylheptylphenol (including isomers), ethylhexyloctylphenol (including isomers), ethylhexylnonylphenol (including isomers), ethylhexyldecylphenol (including isomers), ethylhexyldodecylphenol (including isomers), ethylhexylphenylphenol (including isomers), ethylhexylphenoxyphenol (including isomers), ethylhexylcumylphenol (including isomers), ethylheptyloctylphenol (including isomers), ethylheptylnonylphenol (including isomers), ethylheptyldecylphenol (including isomers), ethylheptyldodecylphenol (including isomers), ethylheptylphenylphenol (including isomers), ethylheptylphenoxyphenol (including isomers), ethylheptylcumylphenol (including isomers), ethyloctylnonylphenol (including isomers), ethyloctyldecylphenol (including isomers), ethyloctyldodecylphenol (including isomers), ethyloctylphenylphenol (including isomers), ethyloctylphenoxyphenol (including isomers), ethyloctylcumylphenol (including isomers), ethylnonyldecylphenol (including isomers), ethylnonyldodecylphenol (including isomers), ethylnonylphenylphenol (including isomers), ethylnonylphenoxyphenol (including isomers), ethylnonylcumylphenol (including isomers), ethyldecyldodecylphenol (including isomers), ethyldecylphenylphenol (including isomers), ethyldecylphenoxyphenol (including isomers), ethyldecylcumylphenol (including isomers), ethyldodecylphenylphenol (including isomers), ethyldodecylphenoxyphenol (including isomers), ethyldodecylcumylphenol (including isomers), ethylphenylphenoxyphenol (including isomers), ethylphenylcumylphenol (including isomers), propylbutylphenol (including isomers), propylbutylpentylphenol (including isomers), propylbutylhexylphenol (including isomers), propylbutylheptylphenol (including isomers), propylbutyloctylphenol (including isomers), propylbutylnonylphenol (including isomers), propylbutyldecylphenol (including isomers), propylbutyldodecylphenol (including isomers), propylbutylphenylphenol (including isomers), propylbutylphenoxyphenol (including isomers), propylbutylcumylphenol (including isomers), propylpentylphenol (including isomers), propylpentylhexylphenol (including isomers), propylpentylheptylphenol (including isomers), propylpentyloctylphenol (including isomers), propylpentylnonylphenol (including isomers), propylpentyldecylphenol (including isomers), propylpentyldodecylphenol (including isomers), propylpentylphenylphenol (including isomers), propylpentylphenoxyphenol (including isomers), propylpentylcumylphenol (including isomers), propyl-hexyl-phenol (including isomers), propylhexylheptylphenol (including isomers), propylhexyloctylphenol (including isomers), propylhexylnonylphenol (including isomers), propylhexyldecylphenol (including isomers), propylhexyldodecylphenol (including isomers), propylhexylphenylphenol (including isomers), propylhexylphenoxyphenol (including isomers), propylhexylcumylphenol (including isomers), propylheptyloctylphenol (including isomers), propylheptylnonylphenol (including isomers), propylheptyldecylphenol (including isomers), propylheptyldodecylphenol (including isomers), propylheptylphenylphenol (including isomers), propylheptylphenoxyphenol (including isomers), propylheptylcumylphenol (including isomers), propyloctylnonylphenol (including isomers), propyloctyldecylphenol (including isomers), propyloctyldodecylphenol (including isomers), propyloctylphenylphenol (including isomers), propyloctylphenoxyphenol (including isomers), propyloctylcumylphenol (including isomers), propylnonyldecylphenol (including isomers), propylnonyldodecylphenol (including isomers), propylnonylphenylphenol (including isomers), propylnonylphenoxyphenol (including isomers), propylnonylcumylphenol (including isomers), propyldecyldodecylphenol (including isomers), propyldecylphenylphenol (including isomers), propyldecylphenoxyphenol (including isomers), propyldecylcumylphenol (including isomers), propyldodecylphenylphenol (including isomers), propyldodecylphenoxyphenol (including isomers), propyldodecylcumylphenol (including isomers), methylphenol (including isomers), ethylphenol (including isomers), propylphenol (including isomers), butylphenol (including isomers), pentylphenol (including isomers), hexylphenol (including isomers), heptylphenol (including isomers), octylphenol (including isomers), nonylphenol (including isomers), decylphenol (including isomers), dodecylphenol (including isomers), phenylphenol (including isomers), phenoxyphenol (including isomers) cumylphenol (including isomers) propylphenylphenoxyphenol (including isomers), propylphenylcumylphenol (including isomers), propylphenoxycumylphenol (including isomers), propyl-butyl-pentyl-phenol (including isomers), propyl-butyl-hexyl-phenol (including isomers), propyl-butyl-heptyl-phenol (including isomers), propyl-butyl-octyl-phenol (including isomers), propyl-butyl-nonyl-phenol (including isomers), propyl-butyl-decyl-phenol (including isomers), propyl-butyl-dodecyl-phenol (including isomers), propyl-butyl-phenyl-phenol (including isomers), propyl-butyl-phenoxyphenol (including isomers), propyl-butyl-cumyl-phenol (including isomers), propyl-pentyl-phenol (including isomers), propyl-pentyl-hexyl-phenol (including isomers), propyl-pentyl-heptyl-phenol (including isomers), propyl-pentyl-octyl-phenol (including isomers), propyl-pentyl-nonyl-phenol (including isomers), propyl-pentyl-decyl-phenol (including isomers), propyl-pentyl-dodecyl-phenol (including isomers), propyl-pentyl-phenyl-phenol (including isomers), propyl-pentyl-phenoxyphenol (including isomers), propyl-pentyl-cumyl-phenol (including isomers), propyl-hexyl-heptyl-phenol (including isomers), propyl-hexyl-octyl-phenol (including isomers), propyl-hexyl-nonyl-phenol (including isomers), propyl-hexyl-decyl-phenol (including isomers), propyl-hexyl-dodecyl-phenol (including isomers), propyl-hexyl-phenyl-phenol (including isomers), propyl-hexyl-phenoxyphenol (including isomers), propyl-hexyl-cumyl-phenol (including isomers), propyl-heptyl-octyl-phenol (including isomers), propyl-heptyl-nonyl-phenol (including isomers), propyl-heptyl-decyl-phenol (including isomers), propyl-heptyl-dodecyl-phenol (including isomers), propyl-heptyl-phenyl-phenol (including isomers), propyl-heptyl-phenoxyphenol (including isomers), propyl-heptyl-cumyl-phenol (including isomers), propyl-octyl-nonyl-phenol (including isomers), propyl-octyl-decyl-phenol (including isomers), propyl-octyl-dodecyl-phenol (including isomers), propyl-octyl-phenyl-phenol (including isomers), propyl-octyl-phenoxyphenol (including isomers), propyl-octyl-cumyl-phenol (including isomers), propyl-nonyl-decyl-phenol (including isomers), propyl-nonyl-dodecyl-phenol (including isomers), propyl-nonyl-phenyl-phenol (including isomers), propyl-nonyl-phenoxyphenol (including isomers), propyl-nonyl-cumyl-phenol (including isomers), propyl-decyl-dodecyl-phenol (including isomers), propyl-decyl-phenyl-phenol (including isomers), propyl-decyl-phenoxyphenol (including isomers), propyl-decyl-cumyl-phenol (including isomers), propyl-dodecyl-phenyl-phenol (including isomers), propyl-dodecyl-phenoxyphenol (including isomers), cumyl-phenol (including isomers) propyl-phenyl-phenoxyphenol (including isomers), propyl-phenyl-cumyl-phenol (including isomers), butylpentylhexylphenol (including isomers), butylpentylheptylphenol (including isomers), butylpentyloctylphenol (including isomers), butylpentylnonylphenol (including isomers), butylpentyldecylphenol (including isomers), butylpentyldodecylphenol (including isomers), butylpentylphenylphenol (including isomers), butylpentylphenoxyphenol (including isomers), butylpentylcumylphenol (including isomers), butylhexylheptylphenol (including isomers), butylhexyloctylphenol (including isomers), butylhexylnonylphenol (including isomers), butylhexyldecylphenol (including isomers), butylhexyldodecylphenol (including isomers), butylhexylphenylphenol (including isomers), butylhexylphenoxyphenol (including isomers), butylhexylcumylphenol (including isomers), butylheptyloctylphenol (including isomers), butylheptylnonylphenol (including isomers), butylheptyldecylphenol (including isomers), butylheptyldodecylphenol (including isomers), butylheptylphenylphenol (including isomers), butylheptylphenoxyphenol (including isomers), butylheptylcumylphenol (including isomers), butyloctylnonylphenol (including isomers), butyloctyldecylphenol (including isomers), butyloctyldodecylphenol (including isomers), butyloctylphenylphenol (including isomers), butyloctylphenoxyphenol (including isomers), butyloctylcumylphenol (including isomers), butylnonyldecylphenol (including isomers), butylnonyldodecylphenol (including isomers), butylnonylphenylphenol (including isomers), butylnonylphenoxyphenol (including isomers), butylnonylcumylphenol (including isomers), butyldecyldodecylphenol (including isomers), butyldecylphenylphenol (including isomers), butyldecylphenoxyphenol (including isomers), butyldecylcumylphenol (including isomers), butyldodecylphenol (including isomers), butyldodecylphenylphenol (including isomers), butyldodecylphenoxyphenol (including isomers), butyldodecylcumylphenol (including isomers), butylphenylphenol (including isomers), butylphenylphenoxyphenol (including isomers), butylphenylcumylphenol (including isomers), pentylhexylheptylphenol (including isomers), pentylhexyloctylphenol (including isomers), pentylhexylnonylphenol (including isomers), pentylhexyldecylphenol (including isomers), pentylhexyldodecylphenol (including isomers), pentylhexylphenylphenol (including isomers), pentylhexylphenoxyphenol (including isomers), pentylhexylcumylphenol (including isomers), pentylheptyloctylphenol (including isomers), pentylheptylnonylphenol (including isomers), pentylheptyldecylphenol (including isomers), pentylheptyldodecylphenol (including isomers), pentylheptylphenylphenol (including isomers), pentylheptylphenoxyphenol (including isomers), pentylheptylcumylphenol (including isomers), pentyloctylnonylphenol (including isomers), pentyloctyldecylphenol (including isomers), pentyloctyldodecylphenol (including isomers), pentyloctylphenylphenol (including isomers), pentyloctylphenoxyphenol (including isomers), pentyloctylcumylphenol (including isomers), pentylnonyldecylphenol (including isomers), pentylnonyldodecylphenol (including isomers), pentylnonylphenylphenol (including isomers), pentylnonylphenoxyphenol (including isomers), pentylnonylcumylphenol (including isomers), pentyldecyldodecylphenol (including isomers), pentyldecylphenylphenol (including isomers), pentyldecylphenoxyphenol (including isomers), pentyldecylcumylphenol (including isomers), pentyldecyldodecylphenol (including isomers), pentyldecylphenylphenol (including isomers), pentyldecylphenoxyphenol (including isomers), pentyldecylcumylphenol (including isomers), pentyldodecylphenylphenol (including isomers), pentyldodecylphenoxyphenol (including isomers), pentyldodecylcumylphenol (including isomers), pentylphenylphenoxyphenol (including isomers), pentylphenylcumylphenol (including isomers), hexylheptyloctylphenol (including isomers), hexylheptylnonylphenol (including isomers), hexylheptyldecylphenol (including isomers), hexylheptyldodecylphenol (including isomers), hexylheptylphenylphenol (including isomers), hexylheptylphenoxyphenol (including isomers), hexylheptylcumylphenol (including isomers), hexyloctylnonylphenol (including isomers), hexyloctyldecylphenol (including isomers), hexyloctyldodecylphenol (including isomers), hexyloctylphenylphenol (including isomers), hexyloctylphenoxyphenol (including isomers), hexyloctylcumylphenol (including isomers), hexylnonyldecylphenol (including isomers), hexylnonyldodecylphenol (including isomers), hexylnonylphenylphenol (including isomers), hexylnonylphenoxyphenol (including isomers), hexyldecyldodecylphenol (including isomers), hexyldecylphenylphenol (including isomers), hexyldecylphenoxyphenol (including isomers), hexyldecylcumylphenol (including isomers), hexyldodecylphenylphenol (including isomers), hexyldodecylphenoxyphenol (including isomers), hexyldodecylcumylphenol (including isomers), hexylphenylphenoxyphenol (including isomers), hexylphenylcumylphenol (including isomers), heptyloctylnonylphenol (including isomers), heptyloctyldecylphenol (including isomers), heptyloctyldodecylphenol (including isomers), heptyloctylphenylhenol (including isomers), heptyloctylphenoxyphenol (including isomers), heptyloctylcumylphenol (including isomers), heptylnonyldecylphenol (including isomers), heptylnonyldodecylphenol (including isomers), heptylnonylphenylhenol (including isomers), heptylnonylphenoxyphenol (including isomers), heptylnonylcumylphenol (including isomers), heptyldecyldodecylphenol (including isomers), heptyldecylphenylphenol (including isomers), heptyldecylphenoxyphenol (including isomers), heptyldecylcumylphenol (including isomers), heptyldodecylphenylhenol (including isomers), heptyldodecylphenoxyphenol (including isomers), heptyldodecylcumylphenol (including isomers), heptylphenylphenoxyphenol (including isomers), heptylphenylcumylphenol (including isomers), octylnonyldecylphenol (including isomers), octylnonyldodecylphenol (including isomers), octylnonylphenylphenol (including isomers), octylnonylphenoxyphenol (including isomers), octylnonylcumylphenol (including isomers), octyldecyldodecylphenol (including isomers), octyldecylphenylphenol (including isomers), octyldecylphenoxyphenol (including isomers), octyldecylcumylphenol (including isomers), octyldodecylphenylphenol (including isomers), octyldodecylphenoxyphenol (including isomers), octyldodecylcumylphenol (including isomers), octyldodecylphenylphenol (including isomers), octyldodecylphenoxyphenol (including isomers), octyldodecylcumylphenol (including isomers), octylphenylphenoxyphenol (including isomers), octylphenylcumylphenol (including isomers), nonyldecyldodecylphenol (including isomers), nonyldecylphenylphenol (including isomers), nonyldecylphenoxyphenol (including isomers), nonyldecylcumylphenol (including isomers), nonyldodecylphenylphenol (including isomers), nonyldodecylphenoxyphenol (including isomers), nonyldodecylcumylphenol (including isomers), nonylphenylphenoxyphenol (including isomers), nonylphenylcumylphenol (including isomers), decyldoceylphenylphenol (including isomers), decyldodecylphenoxyphenol (including isomers), decyldodecylcumylphenol (including isomers), dodecylphenylphenoxyphenol (including isomers), dodecylphenylcumylphenol (including isomers) or phenylphenoxycumylphenol (including isomers). Among these aromatic hydroxy compounds, a compound of the same type as the aromatic hydroxy compound used in the reaction between the aromatic polycarbonate and the amine compound having primary amino groups is more preferable in consideration of the case of the cleaning solvent remaining after cleaning the thermal decomposition reactor.

Various methods can be used to clean the thermal decomposition reactor using the cleaning solvents listed above, examples of which may include a method whereby the thermal decomposition reactor is cleaned by introducing cleaning solvent from the top of the thermal decomposition reactor, and a method whereby the inside of the thermal decomposition reactor is cleaned by introducing cleaning solvent into the bottom of the thermal decomposition reactor and heating up the cleaning solvent inside the thermal decomposition reactor.

There are no particular limitations on the frequency at which cleaning is carried out, and the cleaning frequency can be arbitrarily determined according to the compounds used, operating rate and the like. The thermal decomposition reactor may also be provided with a line for introducing cleaning solvent in the thermal decomposition reactor.

In addition, when carrying out thermal decomposition of carbamic acid ester, the above-mentioned cleaning solvent can also be made to be present under the conditions of the thermal decomposition reaction for the purpose of cleaning the thermal decomposition reactor. This differs from the inert solvent as referred to in the prior art (see, for example, U.S. Pat. No. 4,081,472). For example, according to this patent document, although an inert solvent refers to a compound that does not react with isocyanate formed by thermal decomposition of carbamic acid ester, in contrast, as described in, for example, the Journal of the American Chemical Society, Vol. 64, p. 2229, 1942 that urethane is formed by the reaction of an aromatic hydroxy compound and phenyl isocyanate, aromatic hydroxy compounds are able to react with isocyanates. The aromatic hydroxy compound may be supplied to the thermal decomposition reactor after mixing when transferring the reaction mixture obtained by a reaction between diaryl carbonate and an amine compound to the thermal decomposition reactor, or may be supplied by providing a line for supplying the aromatic hydroxy compound separate from the line for supplying the reaction mixture.

The carbamic acid ester obtained in the process of the present embodiment is preferable as a raw material for producing isocyanate without using extremely toxic phosgene, and isocyanate obtained with the process of the present embodiment can be preferably used as a raw material for the production of polyurethane foam, paints, adhesives and the like. In addition, the divalent aromatic hydroxy compound obtained in the process of the present embodiment can be preferably used as a raw material for the production of aromatic polycarbonates. The process of the present embodiment also demonstrates the aspect of chemical recycling of aromatic polycarbonates. On the basis of the above, the present invention is industrially extremely important.

EXAMPLES

Although the following provides a detailed explanation of the present invention based on examples thereof, the scope of the present invention is not limited by these examples.

<Analytical Methods>

1) NMR Analysis

Apparatus: JNM-A400 FT-NMR system, JEOL Ltd., Japan (1) Preparation of $^1$H and $^{13}$C-NMR Analysis Samples About 0.3 g of sample solution were weighed followed by the addition of about 0.7 g of heavy chloroform (99.8%, Aldrich Corp., USA) and about 0.05 g of internal standard in the form of tetramethyl tin (guaranteed reagent, Wako Pure Chemical Industries, Ltd., Japan) and mixing to uniformity to obtain solutions used as NMR analysis samples.

(2) Quantitative Analysis

Analyses were performed on each standard and quantitative analyses were performed on the analysis sample solutions based on the resulting calibration curve.

2) Liquid Chromatography

Apparatus: LC-10AT system, Shimadzu Corp., Japan

Column: Silica-60 column, Tosoh Corp., Japan, two columns connected in series

Developing solvent: Mixed liquid of hexane/tetrahydrofuran (80/20) (v/v)

Solvent flow rate: 2 mL/min

Column temperature: 35° C.

Detector: R.I. (refractometer)

(1) Liquid Chromatography Analysis Samples

About 0.1 g of sample were weighed followed by the addition of about 1 g of tetrahydrofuran (dehydrated, Wako Pure Chemical Industries, Ltd., Japan) and about 0.02 g of internal standard in the form of bisphenol A (guaranteed reagent, Wako Pure Chemical Industries, Ltd., Japan) and mixing to uniformity to obtain solutions used as liquid chromatography analysis samples.

(2) Quantitative Analysis

Analyses were performed on each standard and quantitative analyses were performed on the analysis sample solutions based on the resulting calibration curve.

3) Gas Chromatography

Apparatus: GC-2010, Shimadzu Corp., Japan

Column: DB-1 column, Agilent Technologies Corp., USA, length: 30 m, inner diameter: 0.250 mm, film thickness: 1.00 μm Column temperature: Held at 50° C. for 5 minutes followed by increasing at the rate of 10° C./min to 200° C.; held at 200° C. for 5 minutes followed by increasing at the rate of 10° C./min to 300° C.

Detector: FID (1) Gas Chromatography Analysis Samples

About 0.05 g of sample were weighed followed by the addition of about 1 g of toluene (dehydrated, Wako Pure Chemical Industries, Ltd., Japan) and about 0.02 g of internal standard in the form of diphenyl ether (Tokyo Chemical Industry Co., Ltd., Japan) and mixing to uniformity to obtain solutions used as gas chromatography analysis samples.

(2) Quantitative Analysis

Analyses were performed on each standard and quantitative analyses were performed on the analysis sample solutions based on the resulting calibration curve.

Example 1

Step (1-1): Preparation of Mixture of Aromatic Polycarbonate and Aromatic Hydroxy Compound A mixture was prepared using an apparatus like that shown in FIG. 1.

20.6 kg (100 mol) of molten 4-t-octylphenol (Tokyo Chemical Industry Co., Ltd., Japan) were transferred from a storage tank 101 to a reactor 102 heated to 200° C. after replacing the inside thereof with nitrogen with a line 12 closed. 14.3 kg of bisphenol A polycarbonate (Aldrich Corp., USA, weight average molecular weight: 65,000) were loaded into the reactor 102 from a storage tank 100 and stirred. After confirming that the bisphenol A polycarbonate had dissolved, line 12 was opened and the mixture was transferred to a storage tank 103.

Step (1-2): Production of Carbamic Acid Ester

Figure 2:
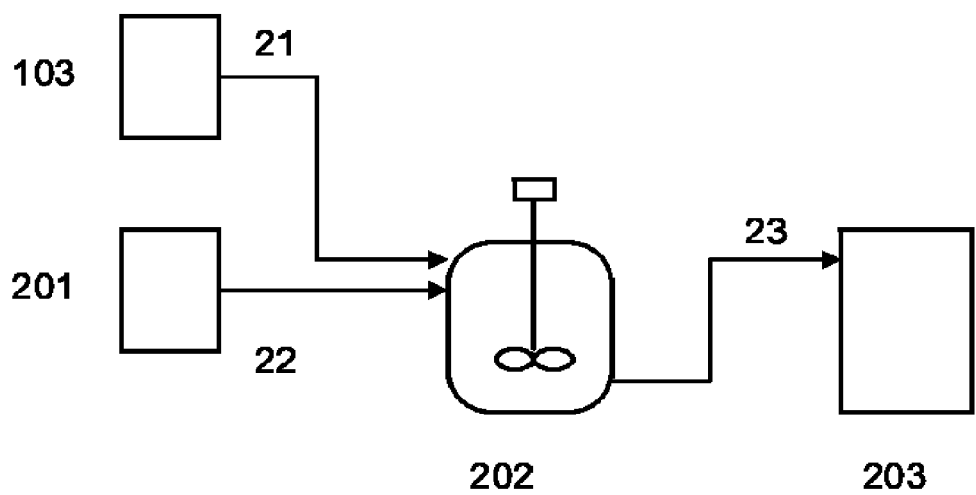
FIG. 2 illustrates a conceptual drawing showing an apparatus for producing a carbamic acid ester used in an example of the present invention.

A reaction was carried out using an apparatus like that shown in FIG. 2.

In a state where a line 23 was closed, the mixture produced in step (1-1) was supplied at a rate of 4.15 kg/hr via a line 21 from storage tank 103 to a baffled SUS reactor 202 maintained at about 150° C. after replacing the inside thereof with nitrogen. Hexamethylene diamine (Aldrich Corp., USA) was supplied at a rate of about 0.24 kg/hr via a line 22 from a storage tank 201 to the reactor 202. After analyzing the reaction liquid by gas chromatography and confirming that hexamethylene diamine was no longer detected, the line 23 was opened and the reaction liquid was transferred to a storage tank 203 via line 23.

Step (1-3): Production of Isocyanate by Thermal Decomposition of Carbamic Acid Ester A reaction was carried out using an apparatus like that shown in FIG. 3.

A thin film distillation apparatus 301 (Kobelco Eco-Solutions Co., Ltd., Japan) having a heat-conducting surface area of 0.1 m$^2$ was heated to 220° C., and an internal pressure was set to about 13 kPa. The mixture recovered in storage tank 203 in step (1-2) was heated to 150° C. and supplied to the top of the thin film distillation apparatus 301 at a rate of about 1120 g/hr via a line 31. A liquid phase component was extracted from a line 32 from the bottom of the thin film distillation apparatus 301 and circulated to the top of the thin film distillation apparatus 301 via a line 36. A gaseous phase component was extracted from a line 33 from the thin film distillation apparatus 301 and supplied to a continuous multistage distillation column 302.

The gaseous phase component extracted via the line 33 from the thin film distillation apparatus 301 was continuously fed to an intermediate stage of the continuous multistage distillation column 302 having an inner diameter of about 5 cm and column length of 2 m and packed with Dixon packing (diameter: 6 mm) to carry out distillative separation of the gaseous phase component. The amount of heat required for distillative separation was supplied by circulating the liquid in the bottom of the column through a line 39 and a reboiler 305. The liquid temperature in the bottom of the continuous multistage distillation column 302 was 150° C., and the pressure at the top of the column was about 15 kPa. A liquid phase component was extracted from the line 33 of the continuous multistage distillation column 302 provided at a location lower than a line 32 and supplied to a continuous multistage distillation column 312. The continuous multistage distillation column 312 was a continuous multistage distillation column having an inner diameter of about 5 cm and column length of 2 m packed with Dixon packing (diameter: 6 mm), and was used to carry out distillative separation of the liquid phase component extracted from the continuous multistage distillation column 302 with this distillation column. The amount of heat required for distillative separation was supplied by circulating liquid in the bottom of the column through a line 41 and a reboiler 310. The liquid temperature in the bottom of the multistage continuous distillation column 312 was 170° C., and the pressure at the top of the column was about 15 kPa. Gas distilled from the top of the continuous multistage distillation column 312 was condensed in a condenser 308 via a line 34, continuously extracted from a line 35 at the rate of about 89 g/hr and recovered in a storage tank 309. Liquid extracted from line was a solution containing about 99.8% by weight of hexamethylene diisocyanate, and the yield based on hexamethylene diamine was about 85%.

Step (1-4) Recovery of Aromatic Hydroxy Compound

Figure 3:
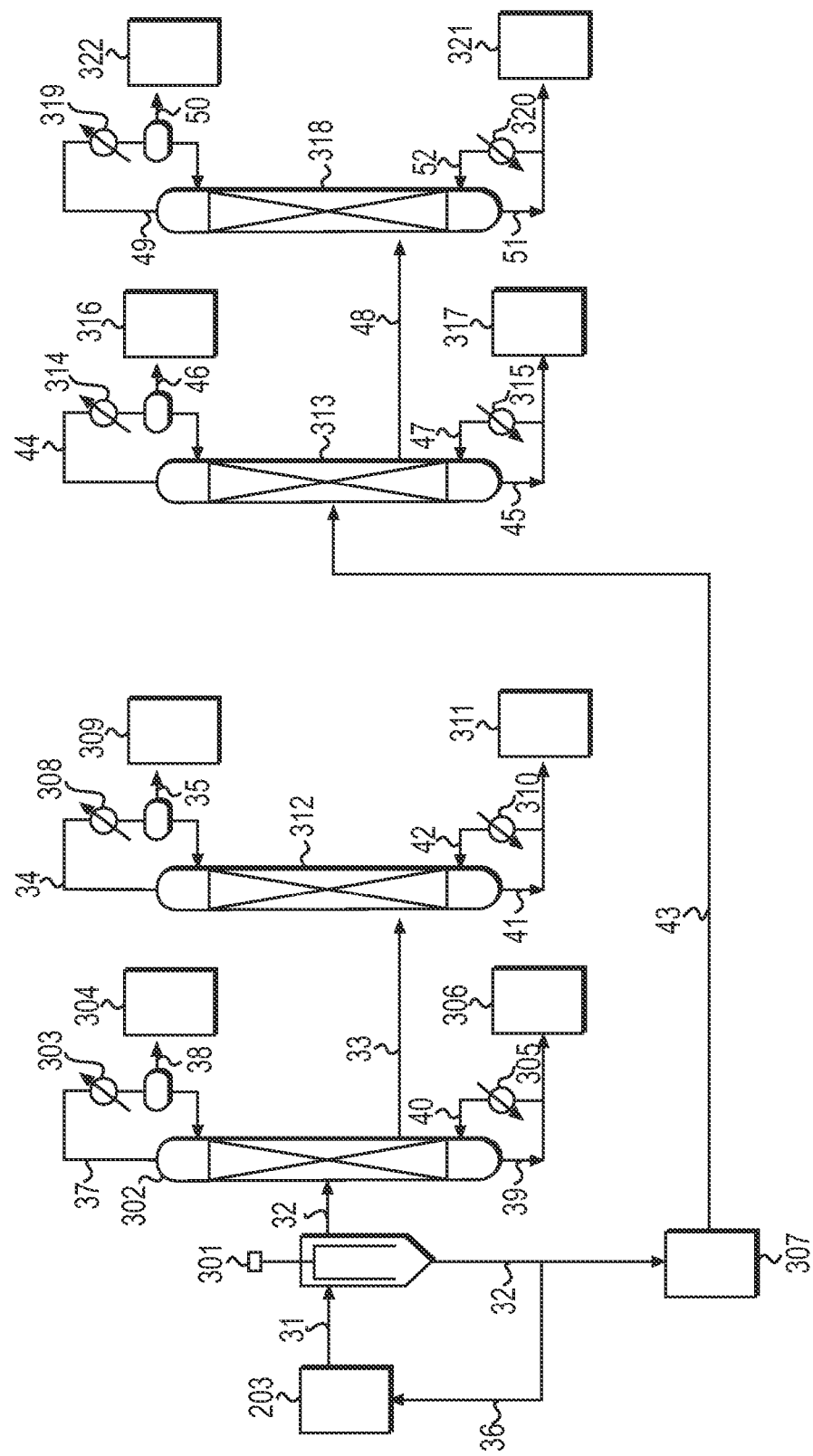
FIG. 3 illustrates a conceptual drawing showing an apparatus for producing an isocyanate and aromatic hydroxy compound used in an example of the present invention.

An apparatus was used like that shown in FIG. 3.

The liquid phase component recovered in storage tank 307 in step (1-3) was continuously fed to the intermediate stage of a continuous multistage distillation column 313 having an inner diameter of about 5 cm and a column length of 2 m and packed with Dixon packing (diameter: 6 mm) to carry out separative distillation of the liquid phase component. The amount of heat required for distillative separation was supplied by circulating a portion of the liquid in the bottom of the column through a line 45 and a reboiler 315. The liquid temperature of the liquid in the bottom of continuous multistage distillation column 313 was 260° C. and the pressure at the top of column was about 1.3 kPa. Gas distilled from the top of continuous multistage distillation column 313 was condensed in a condenser 316 via a line 44 and continuously extracted into a storage tank 316 via a line 46.

A liquid phase component was extracted from a line 48 of the continuous multistage distillation column 313 provided at a location lower than a line 43 and supplied to a continuous multistage distillation column 318.

The liquid phase component supplied to the continuous multistage distillation column 318 via the line 48 was separated by distillation in that distillation column. The liquid temperature at the bottom of the continuous multistage distillation column 318 was 240° C. and the pressure at the top of the column was about 0.5 kPa. Gas distilled from the top of the distillation column 318 was condensed in a condenser 319 via a line 49 and continuously extracted at a rate of about 180 g/hr into a storage tank 309 via a line 50.

Liquid extracted from line 46 was a solution containing about 99% by weight of 4-t-octylphenol. In addition, liquid extracted from line 50 was a liquid containing about 99% by weight of bisphenol A.

Example 2

Step (2-1): Preparation of Mixture of Aromatic Polycarbonate and Aromatic Hydroxy Compound A mixture was prepared by carrying out the same method as step (1-1) of Example 1 with the exception of using 14.1 kg of 2,4-di-t-amylphenol (Tokyo Chemical Industry Co., Ltd., Japan) instead of 4-t-octylphenol, and using 8.64 kg of bisphenol A polycarbonate.

Step (2-2): Production of Carbamic Acid Ester

The same method as step (1-2) of Example 1 was carried out with the exception of supplying the mixture prepared in step (2-1) at 9.08 kg/hr instead of the mixture produced in step (1-1) and supplying hexamethylene diamine at 0.46 kg/hr to the reactor 202.

As a result of analyzing the solution following the reaction by gas chromatography, hexamethylene diamine was not detected.

Step (2-3): Production of Isocyanate by Thermal Decomposition of Carbamic Acid Ester The same method as step (1-3) of Example 1 was carried out with the exception of supplying the mixture recovered in step (2-2) instead of the mixture recovered in step (1-2) to the thin film distillation apparatus 301 at 150° C. and at a rate of about 1165 g/hr, condensing gas distilled from the top of the continuous multistage distillation column 312 in condenser 308 via line 34, continuously extracting from line 35 at a rate of about 69 g/hr and recovering in storage tank 309. The liquid extracted from a line 35 was a solution containing 99.8% by weight of hexamethylene diisocyanate, and the yield based on hexamethylene diamine was about 85%.

Step (2-4): Recovery of Aromatic Hydroxy Compound

An apparatus was used like that shown in FIG. 3.

The same method as step (1-4) of Example 1 was carried out with the exception of using the liquid phase component recovered in step (2-3) instead of the liquid phase component recovered in storage tank 307 in step (1-3), a solution containing about 99% by weight of 2,4-di-t-amylphenol was recovered from a line 46 at a rate of about 640 g/hr, and a liquid containing about 99% by weight of bisphenol A was recovered from line 50 at the rate of about 370 g/hr.

Example 3

Step (3-1): Preparation of Mixture of Aromatic Polycarbonate and Aromatic Hydroxy Compound A mixture was prepared by carrying out the same method as step (1-1) of Example 1 with the exception of using 13.2 kg of 4-nonylphenol (Aldrich Corp., USA) instead of 4-t-octylphenol, and using 8.64 kg of bisphenol A polycarbonate.

Step (3-2): Production of Carbamic Acid Ester

The same method as step (1-2) of Example 1 was carried out with the exception of supplying the mixture prepared in step (3-1) at a rate of 10.9 kg/hr instead of the mixture produced in step (1-1) and supplying hexamethylene diamine at a rate of 0.58 kg/hr to the reactor 202.

As a result of analyzing the solution following the reaction by gas chromatography, hexamethylene diamine was not detected.

Step (3-3): Production of Isocyanate by Thermal Decomposition of Carbamic Acid Ester The same method as step (1-3) of Example 1 was carried out with the exception of supplying the mixture recovered in step (3-2) instead of the mixture recovered in step (1-2) to the thin film distillation apparatus 301 at 150° C. and at a rate of 1.2 kg/hr, condensing gas distilled from the top of the continuous multistage distillation column 312 in condenser 308 via a line 34, continuously extracting from a line 35 at a rate of about 73 g/hr and recovering in storage tank 309. The liquid extracted from the line 35 was a solution containing 99.8% by weight of hexamethylene diisocyanate, and the yield based on hexamethylene diamine was about 84%.

Step (3-4): Recovery of Aromatic Hydroxy Compound

The same method as step (1-4) of Example 1 was carried out with the exception of using the liquid phase component recovered in step (3-3) instead of the liquid phase component recovered in storage tank 307 in step (1-3), a solution containing about 99% by weight of 4-nonylphenol was recovered from line 46 at the rate of about 630 g/hr, and a liquid containing about 99% by weight of bisphenol A was recovered from line 50 at a rate of about 382 g/hr.

Example 4

Step (4-1): Preparation of Mixture of Aromatic Polycarbonate and Aromatic Hydroxy Compound A mixture was prepared by carrying out the same method as step (1-1) of Example 1 with the exception of using 24.3 kg of 4-dodecylphenol (Aldrich Corp., USA) instead of 4-t-octylphenol, and using 10.7 kg of bisphenol A polycarbonate.

Step (4-2): Production of Carbamic Acid Ester

The same method as step (1-2) of Example 1 was carried out with the exception of supplying the mixture prepared in step (4-1) at 17.5 kg/hr instead of the mixture produced in step (1-1) and supplying hexamethylene diamine at 0.62 kg/hr to the reactor 202.

As a result of analyzing the solution following the reaction by gas chromatography, hexamethylene diamine was not detected.

Step (4-3): Production of Isocyanate by Thermal Decomposition of Carbamic Acid Ester The same method as step (1-3) of Example 1 was carried out with the exception of supplying the mixture recovered in step (4-2) instead of the mixture recovered in step (1-2) to the thin film distillation apparatus 301 at 150° C. and at a rate of 2.0 kg/hr, condensing gas distilled from the top of the continuous multistage distillation column 312 in condenser 308 via a line 34, continuously extracting from a line 35 at a rate of about 83 g/hr and recovering in storage tank 309. The liquid extracted from the line 35 was a solution containing about 99.8% by weight of hexamethylene diisocyanate, and the yield based on hexamethylene diamine was about 85%.

Step (4-4): Recovery of Aromatic Hydroxy Compound

The same method as step (1-4) of Example 1 was carried out with the exception of using the liquid phase component recovered in step (4-3) instead of the liquid phase component recovered in storage tank 307 in step (1-3), a solution containing about 99% by weight of 4-dodecylphenol was recovered from a line 46 at the rate of about 1250 g/hr, and a liquid containing about 99% by weight of bisphenol A was recovered from a line 50 at a rate of about 445 g/hr.

Example 5

Step (5-1): Preparation of Mixture of Aromatic Polycarbonate and Aromatic Hydroxy Compound A mixture was prepared by carrying out the same method as step (1-1) of Example 1 with the exception of using 11.3 kg of 4-cumylphenol (Aldrich Corp., USA) instead of 4-t-octylphenol, and using 7.7 kg of bisphenol A polycarbonate.

Step (5-2): Production of Carbamic Acid Ester

The same method as step (1-2) of Example 1 was carried out with the exception of supplying the mixture prepared in step (5-1) at 9.50 kg/hr instead of the mixture produced in step (1-1) and supplying hexamethylene diamine at 0.50 kg/hr to the reactor 202.

As a result of analyzing the solution following the reaction by gas chromatography, hexamethylene diamine was not detected.

Step (5-3): Production of Isocyanate by Thermal Decomposition of Carbamic Acid Ester The same method as step (1-3) of Example 1 was carried out with the exception of supplying the mixture recovered in step (5-2) instead of the mixture recovered in step (1-2) to the thin film distillation apparatus 301 at 150° C. and at a rate of 2.1 kg/hr, condensing gas distilled from the top of the continuous multistage distillation column 312 in condenser 308 via a line 34, continuously extracting from a line 35 at a rate of about 125 g/hr and recovering in storage tank 309. The liquid extracted from the line 35 was a solution containing about 99.8% by weight of hexamethylene diisocyanate, and the yield based on hexamethylene diamine was about 83%.

Step (5-4): Recovery of Aromatic Hydroxy Compound

The same method as step (1-4) of Example 1 was carried out with the exception of using the liquid phase component recovered in step (5-3) instead of the liquid phase component recovered in storage tank 307 in step (1-3), a solution containing about 99% by weight of 4-cumylphenol was recovered from line 46 at a rate of about 1110 g/hr, and a liquid containing about 99% by weight of bisphenol A was recovered from line 50 at a rate of about 660 g/hr.

Example 6

Step (6-1): Preparation of Mixture of Aromatic Polycarbonate and Aromatic Hydroxy Compound A mixture was prepared by carrying out the same method as step (1-1) of Example 1 with the exception of using 18.2 kg of 2,4-dicumylphenol (Aldrich Corp., USA) instead of 4-t-octylphenol, and using 6.34 kg of bisphenol A polycarbonate.

Step (6-2): Production of Carbamic Acid Ester

The same method as step (1-2) of Example 1 was carried out with the exception of supplying the mixture prepared in step (6-1) at 12.3 kg/hr instead of the mixture produced in step (1-1) and supplying hexamethylene diamine at 0.51 kg/hr to the reactor 202.

As a result of analyzing the solution following the reaction by gas chromatography, hexamethylene diamine was not detected.

Step (6-3): Production of Isocyanate by Thermal Decomposition of Carbamic Acid Ester The same method as step (1-3) of Example 1 was carried out with the exception of supplying the mixture recovered in step (6-2) instead of the mixture recovered in step (1-2) to the thin film distillation apparatus 301 at 150° C. and at a rate of 2.1 kg/hr, condensing gas distilled from the top of the continuous multistage distillation column 312 in condenser 308 via a line 34, continuously extracting from a line 35 at a rate of about 100 g/hr and recovering in storage tank 309. The liquid extracted from the line 35 was a solution containing about 99.8% by weight of hexamethylene diisocyanate, and the yield based on hexamethylene diamine was about 82%.

Step (6-4): Recovery of Aromatic Hydroxy Compound

The same method as step (1-4) of Example 1 was carried out with the exception of using the liquid phase component recovered in step (6-3) instead of the liquid phase component recovered in storage tank 307 in step (1-3), a solution containing about 99% by weight of 2,4-dicumylphenol was recovered from a line 46 at a rate of about 1410 g/hr, and a liquid containing about 99% by weight of bisphenol A was recovered from line 50 at the rate of about 510 g/hr.

Example 7

Step (7-1): Preparation of Mixture of Aromatic Polycarbonate and Aromatic Hydroxy Compound A mixture was prepared by carrying out the same method as step (1-1) of Example 1 with the exception of using 16.8 kg of 2,4-di-t-amylphenol (Aldrich Corp., USA) instead of 4-t-octylphenol, using 6.91 kg of bisphenol A polycarbonate, and mixing 0.10 kg of titanium tetra-isopropoxide (Aldrich Corp., USA) into the 2,4-di-t-amylphenol.

Step (7-2): Production of Carbamic Acid Ester

The same method as step (1-2) of Example 1 was carried out with the exception of supplying the mixture prepared in step (7-1) at 11.9 kg/hr instead of the mixture produced in step (1-1) and supplying hexamethylene diamine at 0.46 kg/hr to the reactor 202.

As a result of analyzing the solution following the reaction by gas chromatography, hexamethylene diamine was not detected.

Step (7-3): Production of Isocyanate by Thermal Decomposition of Carbamic Acid Ester The same method as step (1-3) of Example 1 was carried out with the exception of supplying the mixture recovered in step (7-2) instead of the mixture recovered in step (1-2) to the thin film distillation apparatus 301 at 150° C. and at a rate of 1.98 kg/hr, condensing gas distilled from the top of the continuous multistage distillation column 312 in condenser 308 via a line 34, continuously extracting from a line 35 at a rate of about 86 g/hr and recovering in storage tank 309. The liquid extracted from the line 35 was a solution containing about 99.8% by weight of hexamethylene diisocyanate, and the yield based on hexamethylene diamine was about 80%.

Step (7-4): Recovery of Aromatic Hydroxy Compound

The same method as step (1-4) of Example 1 was carried out with the exception of using the liquid phase component recovered in step (7-3) instead of the liquid phase component recovered in storage tank 307 in step (1-3), a solution containing about 99% by weight of 2,4-di-t-amylphenol was recovered from a line 46 at a rate of about 1203 g/hr, and a liquid containing about 99% by weight of bisphenol A was recovered from a line 50 at a rate of about 430 g/hr.

Example 8

Step (8-1): Preparation of Mixture of Aromatic Polycarbonate and Aromatic Hydroxy Compound A mixture was prepared by carrying out the same method as step (1-1) of Example 1 with the exception of using 15.6 kg of bisphenol A (Aldrich Corp., USA) instead of 4-t-octylphenol, and using 6.57 kg of bisphenol A polycarbonate.

Step (8-2): Production of Carbamic Acid Ester

The same method as step (1-2) of Example 1 was carried out with the exception of supplying the mixture prepared in step (8-1) at 11.3 kg/hr instead of the mixture produced in step (1-1) and supplying hexamethylene diamine at 0.44 kg/hr to the reactor 202.

As a result of analyzing the solution following the reaction by gas chromatography, hexamethylene diamine was not detected.

Step (8-3): Production of Isocyanate by Thermal Decomposition of Carbamic Acid Ester The same method as step (1-3) of Example 1 was carried out with the exception of supplying the mixture recovered in step (8-2) instead of the mixture recovered in step (1-2) to the thin film distillation apparatus 301 at 180° C. and at a rate of 2.12 kg/hr, condensing gas distilled from the top of the continuous multistage distillation column 312 in condenser 308 via a line 34, continuously extracting from a line 35 at a rate of about 90 g/hr and recovering in storage tank 309. The liquid extracted from the line 35 was a solution containing about 99.8% by weight of hexamethylene diisocyanate, and the yield based on hexamethylene diamine was about 77%.

Step (8-4): Recovery of Aromatic Hydroxy Compound

The same method as step (1-4) of Example 1 was carried out with the exception of using the liquid phase component recovered in step (8-3) instead of the liquid phase component recovered in storage tank 307 in step (1-3), and a solution containing about 99% by weight of bisphenol A was recovered from a line 50 at a rate of about 1633 g/hr.

Example 9

Step (9-1): Preparation of Mixture of Aromatic Polycarbonate and Aromatic Hydroxy Compound A mixture was prepared by carrying out the same method as step (1-1) of Example 1 with the exception of using 25.3 kg of 2,4-di-t-amylphenol instead of 4-t-octylphenol, and using 10.4 kg of bisphenol A polycarbonate.

Step (9-2): Production of Carbamic Acid Ester

The same method as step (1-2) of Example 1 was carried out with the exception of supplying the mixture prepared in step (9-1) at 8.92 kg/hr instead of the mixture produced in step (1-1) and supplying 3-aminomethyl-3,5,5-trimethyl cyclohexylamine at 0.51 kg/hr to the reactor 202.

As a result of analyzing the solution following the reaction by gas chromatography, 3-aminomethyl-3,5,5-trimethyl cyclohexylamine was not detected.

Step (9-3): Production of Isocyanate by Thermal Decomposition of Carbamic Acid Ester The same method as step (1-3) of Example 1 was carried out with the exception of supplying the mixture recovered in step (9-2) instead of the mixture recovered in step (1-2) to the thin film distillation apparatus 301 at 180° C. and at a rate of 2.10 kg/hr, condensing gas distilled from the top of the continuous multistage distillation column 312 in condenser 308 via a line 34, continuously extracting from a line 35 at a rate of about 119 g/hr and recovering in storage tank 309. The liquid extracted from the line 35 was a solution containing about 99.8% by weight of isophorone diisocyanate, and the yield based on 3-aminomethyl-3,5,5-trimethyl cyclohexylamine was about 80%.

Step (9-4): Recovery of Aromatic Hydroxy Compound

The same method as step (1-4) of Example 1 was carried out with the exception of using the liquid phase component recovered in step (9-3) instead of the liquid phase component recovered in storage tank 307 in step (1-3), and a solution containing about 99% by weight of bisphenol A was recovered from a line 50 at a rate of about 500 g/hr.

Example 10

Step (10-1): Preparation of Mixture of Aromatic Polycarbonate and Aromatic Hydroxy Compound Waste compact disks (polycarbonate vapor-deposited with aluminum and coated with lacquer) were crushed with a shredder to a particle diameter of about 1 to 15 mm.

A mixture was prepared by carrying out the same method as step (1-1) of Example 1 with the exception of using 33.8 kg of 2,4-di-t-amylphenol instead of 4-t-octylphenol, and using 13.8 kg of the polycarbonate crushed according to the method described above instead of bisphenol A polycarbonate.

Step (10-2): Production of Carbamic Acid Ester

The same method as step (1-2) of Example 1 was carried out with the exception of supplying the mixture prepared in step (10-1) at 11.9 kg/hr instead of the mixture produced in step (1-1) and supplying 3-aminomethyl-3,5,5-trimethyl cyclohexylamine at 0.68 kg/hr to the reactor 202.

As a result of analyzing the solution following the reaction by gas chromatography, 3-aminomethyl-3,5,5-trimethyl cyclohexylamine was not detected.

Step (10-3): Production of Isocyanate by Thermal Decomposition of Carbamic Acid Ester The same method as step (1-3) of Example 1 was carried out with the exception of supplying the mixture recovered in step (10-2) instead of the mixture recovered in step (1-2) to the thin film distillation apparatus 301 at 175° C. and at a rate of 1.90 kg/hr, condensing gas distilled from the top of the continuous multistage distillation column 312 in condenser 308 via a line 34, continuously extracting from a line 35 at a rate of about 90 g/hr and recovering in storage tank 309. The liquid extracted from the line 35 was a solution containing about 99.8% by weight of isophorone diisocyanate, and the yield based on 3-aminomethyl-3,5,5-trimethyl cyclohexylamine was about 67%.

Step (10-4): Recovery of Aromatic Hydroxy Compound

The same method as step (1-4) of Example 1 was carried out with the exception of using the liquid phase component recovered in step (10-3) instead of the liquid phase component recovered in storage tank 307 in step (1-3), and a solution containing about 99% by weight of bisphenol A was recovered from line 50 at the rate of about 390 g/hr.

Example 11

Step (11-1): Preparation of Mixture of Aromatic Polycarbonate and Aromatic Hydroxy Compound A mixture was prepared by carrying out the same method as step (1-1) of Example 1 with the exception of using 33.3 kg of 2,4,-di-cumylphenol instead of 4-t-octylphenol, and using 9.8 kg of bisphenol A polycarbonate.

Step (11-2): Production of Carbamic Acid Ester

The same method as step (1-2) of Example 1 was carried out with the exception of supplying the mixture prepared in step (11-1) at 10.7 kg/hr instead of the mixture produced in step (1-1) and supplying 3-aminomethyl-3,5,5-trimethyl cyclohexylamine at 0.47 kg/hr to the reactor 202.

As a result of analyzing the solution following the reaction by gas chromatography, 3-aminomethyl-3,5,5-trimethyl cyclohexylamine was not detected.

Step (11-3): Production of Isocyanate by Thermal Decomposition of Carbamic Acid Ester The same method as step (1-3) of Example 1 was carried out with the exception of supplying the mixture recovered in step (11-2) instead of the mixture recovered in step (1-2) to the thin film distillation apparatus 301 at 180° C. and at a rate of 2.20 kg/hr, condensing gas distilled from the top of the continuous multistage distillation column 312 in condenser 308 via a line 34, continuously extracting from a line 35 at a rate of about 94 g/hr and recovering in storage tank 309. The liquid extracted from the line 35 was a solution containing about 99.8% by weight of isophorone diisocyanate, and the yield based on 3-aminomethyl-3,5,5-trimethyl cyclohexylamine was about 77%.

Step (11-4): Recovery of Aromatic Hydroxy Compound

The same method as step (1-4) of Example 1 was carried out with the exception of using the liquid phase component recovered in step (11-3) instead of the liquid phase component recovered in storage tank 307 in step (1-3), and a solution containing about 99% by weight of bisphenol A was recovered from line 50 at the rate of about 395 g/hr.

Example 12

Step (12-1): Preparation of Mixture of Aromatic Polycarbonate and Aromatic Hydroxy Compound A mixture was prepared by carrying out the same method as step (1-1) of Example 1 with the exception of using 25.5 kg of bisphenol A instead of 4-t-octylphenol, and using 10.7 kg of bisphenol A polycarbonate.

Step (12-2): Production of Carbamic Acid Ester

The same method as step (1-2) of Example 1 was carried out with the exception of supplying the mixture prepared in step (12-1) at 9.04 kg/hr instead of the mixture produced in step (1-1) and supplying 3-aminomethyl-3,5,5-trimethyl cyclohexylamine at 0.53 kg/hr to the reactor 202.

As a result of analyzing the solution following the reaction by gas chromatography, 3-aminomethyl-3,5,5-trimethyl cyclohexylamine was not detected.

Step (12-3): Production of Isocyanate by Thermal Decomposition of Carbamic Acid Ester The same method as step (1-3) of Example 1 was carried out with the exception of supplying the mixture recovered in step (12-2) instead of the mixture recovered in step (1-2) to the thin film distillation apparatus 301 at 180° C. and at a rate of 1.89 kg/hr, condensing gas distilled from the top of the continuous multistage distillation column 312 in condenser 308 via a line 34, continuously extracting from a line 35 at a rate of about 99 g/hr and recovering in storage tank 309. The liquid extracted from the line 35 was a solution containing about 99.8% by weight of isophorone diisocyanate, and the yield based on 3-aminomethyl-3,5,5-trimethyl cyclohexylamine was about 72%.

Step (12-4): Recovery of Aromatic Hydroxy Compound

The same method as step (1-4) of Example 1 was carried out with the exception of using the liquid phase component recovered in step (12-3) instead of the liquid phase component recovered in storage tank 307 in step (1-3), and a solution containing about 99% by weight of bisphenol A was recovered from a line 50 at the rate of about 420 g/hr.

Example 13

Step (13-1): Preparation of Mixture of Aromatic Polycarbonate and Aromatic Hydroxy Compound A mixture was prepared by carrying out the same method as step (1-1) of Example 1 with the exception of using 34.1 kg of 4-t-octylphenol and using 11.1 kg of bisphenol A polycarbonate.

Step (13-2): Production of Carbamic Acid Ester

The same method as step (1-2) of Example 1 was carried out with the exception of supplying the mixture prepared in step (13-1) at 11.3 kg/hr instead of the mixture produced in step (1-1) and supplying 4,4'-methylenebis(cyclohexylamine) (Aldrich Corp., USA) at 0.63 kg/hr to the reactor 202.

As a result of analyzing the solution following the reaction by gas chromatography, 4,4'-methylenebis(cyclohexylamine) was not detected.

Step (13-3): Production of Isocyanate by Thermal Decomposition of Carbamic Acid Ester The reaction was carried out using an apparatus like that shown in FIG. 4. A thin film distillation apparatus 401 (Kobelco Eco-Solutions Co., Ltd., Japan) having a heat-conducting surface area of 0.1 m$^2$ was heated to 280° C., and the internal pressure was set to about 0.5 kPa. The mixture recovered in storage tank 203 in step (13-2) was heated to 180° C. and supplied to the top of the thin film distillation apparatus 401 at a rate of about 2210 g/hr via a line 61. A portion of a liquid phase component extracted from the bottom of the thin film distillation apparatus 401 was circulated to the top of the thin film distillation apparatus 401 via a line 66 and a line 60, while the remainder was extracted into a storage tank 407. On the other hand, a gaseous phase component was extracted from a line 62 and supplied to a continuous multistage distillation column 402.

The gaseous phase component extracted via the line 62 from the thin film distillation apparatus 401 was continuously fed to the intermediate stage of the continuous multistage distillation column 402 having an inner diameter of about 5 cm and a column length of 2 m and packed with Dixon packing (diameter: 6 mm) to carry out distillative separation of the gaseous phase component. The amount of heat required for distillative separation was supplied by circulating the liquid in the bottom of the column through a line 69 and a reboiler 405. The liquid temperature in the bottom of the continuous multistage distillation column 402 was 220° C., and the pressure at the top of the column was about 3 kPa. A liquid phase component was supplied from the bottom of the continuous multistage distillation column 402 to a continuous multistage distillation column 412 via the line 69 and the line 63. The continuous multistage distillation column 412 was a continuous multistage distillation column having an inner diameter of about 5 cm and a column length of 2 m and packed with Dixon packing (diameter: 6 mm), and distillative separation of the liquid phase component supplied from the continuous multistage distillation column 402 was carried out with this distillation column. The amount of heat required for distillative separation was supplied by circulating liquid in the bottom of the column through a line 71 and a reboiler 410. The liquid temperature in the bottom of the multistage continuous distillation column 412 was 230° C., and the pressure at the top of the column was about 0.5 kPa. Gas distilled from the top of the continuous multistage distillation column 412 was condensed in a condenser 408 via a line 64, continuously extracted from a line 65 at a rate of about 105 g/hr and recovered in a storage tank 409.

Liquid extracted from the line 65 was a solution containing about 99% by weight of 4,4'-methylenebis(cyclohexylisocyanate), and the yield based on 4,4'-methylenebis(cyclohexylamine) was about 72%.

Step (13-4) Recovery of Aromatic Hydroxy Compound

Figure 4:
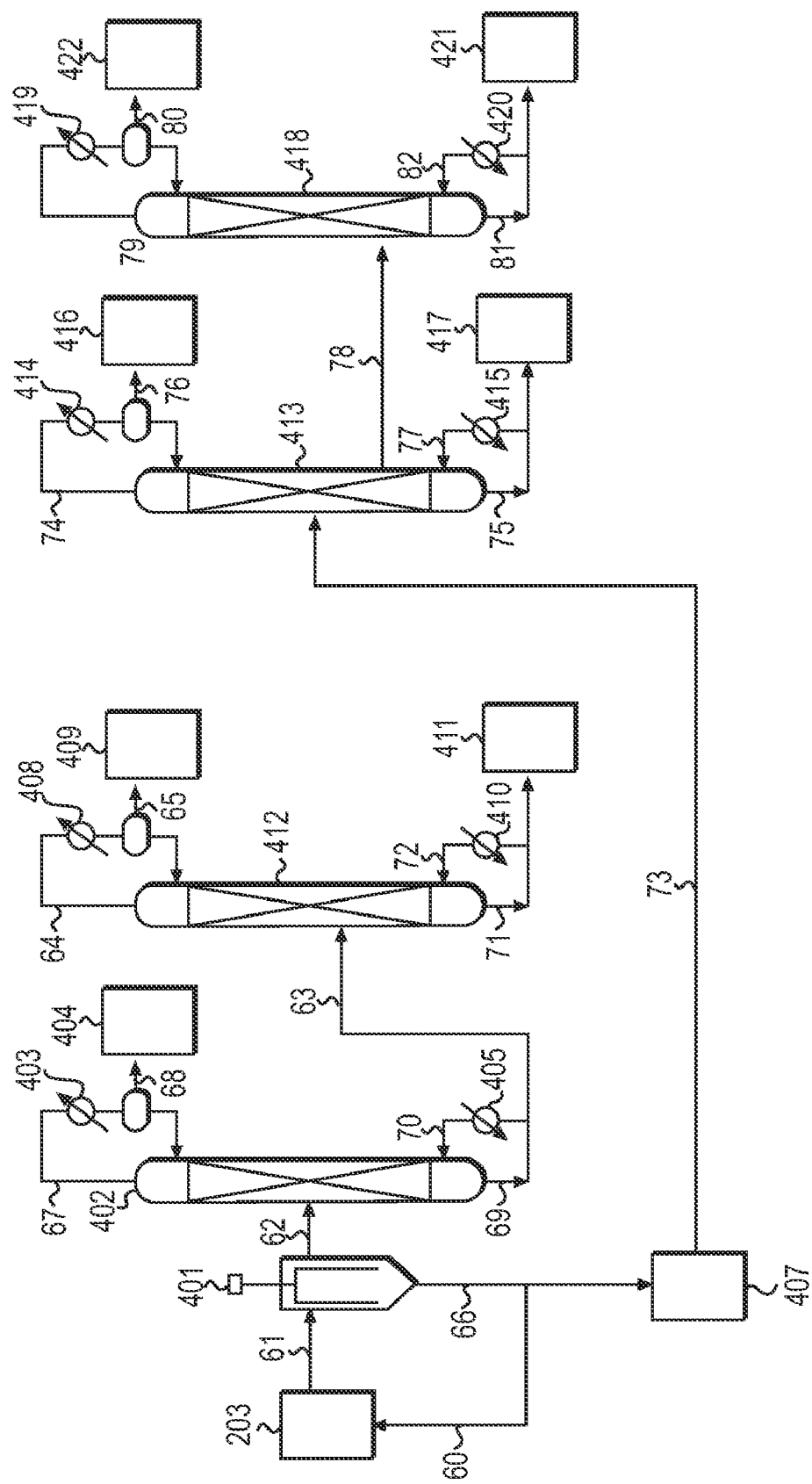
FIG. 4 illustrates a conceptual drawing showing an apparatus for producing an isocyanate and aromatic hydroxy compound used in an example of the present invention.
Figure 5:
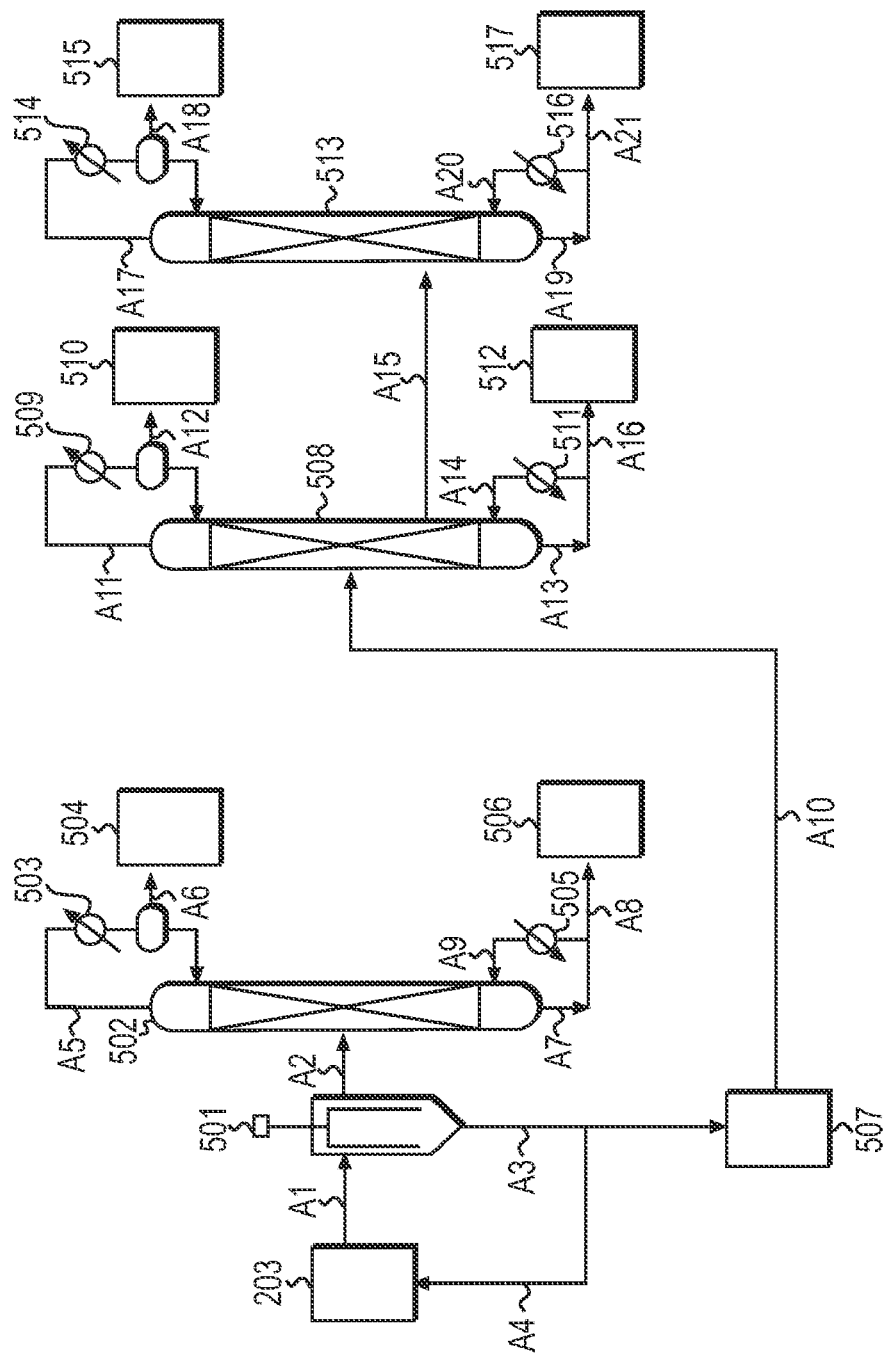
FIG. 5 illustrates a conceptual drawing showing an apparatus for producing an isocyanate and aromatic hydroxy compound used in an example of the present invention.

Next, an apparatus was used like that shown in FIG. 4.

The liquid phase component recovered in storage tank 407 in step (13-3) was continuously fed to an intermediate stage of a continuous multistage distillation column 413 having an inner diameter of about 5 cm and a column length of 2 m and packed with Dixon packing (diameter: 6 mm) to carry out separative distillation of the liquid phase component. The amount of heat required for distillative separation was supplied by circulating a portion of the liquid in the bottom of the column through a line 75 and a reboiler 415. The liquid temperature of the liquid in the bottom of continuous multistage distillation column 413 was 170° C. and the pressure at the top of column was about 1.3 kPa. Gas distilled from the top of continuous multistage distillation column 413 was condensed in a condenser 414 via a line 74 and continuously extracted into a storage tank 416 via a line 76. A liquid phase component was extracted from a line 78 of the continuous multistage distillation column 413 provided at a location lower than a line 73 and supplied to a continuous multistage distillation column 418.

The liquid phase component supplied to the continuous multistage distillation column 418 via the line 78 was separated by distillation in that distillation column. The liquid temperature at the bottom of the continuous multistage distillation column 418 was 240° C. and the pressure at the top of the column was 0.5 kPa. Gas distilled from the top of the distillation column 418 was condensed in a condenser 419 via a line 79 and continuously extracted at a rate of about 350 g/hr into a storage tank 409 via a line 80. Liquid extracted from the line 80 was a solution containing about 99% by weight of bisphenol A.

Example 14

Step (14-1): Preparation of Mixture of Aromatic Polycarbonate and Aromatic Hydroxy Compound A mixture was prepared by carrying out the same method as step (1-1) of Example 1 with the exception of using 25.3 kg of 2,4-di-t-amylphenol instead of 4-t-octylphenol and using 10.4 kg of bisphenol A polycarbonate.

Step (14-2): Production of Carbamic Acid Ester

The same method as step (1-2) of Example 1 was carried out with the exception of supplying the mixture prepared in step (14-1) at 8.92 kg/hr instead of the mixture produced in step (1-1) and supplying 4,4'-methylenebis(cyclohexylamine) at 0.63 kg/hr to the reactor 202.

As a result of analyzing the solution following the reaction by gas chromatography, 4,4'-methylenebis(cyclohexylamine) was not detected.

Step (14-3): Production of Isocyanate by Thermal Decomposition of Carbamic Acid Ester The same method as step (13-3) of Example 13 was carried out with the exception of supplying the mixture recovered in step (14-2) instead of the mixture recovered in step (13-2) to the thin film distillation apparatus 401 at 180° C. and at a rate of 2.28 kg/hr, condensing gas distilled from the top of the continuous multistage distillation column 412 in condenser 408 via a line 64, continuously extracting from a line 65 at a rate of about 132 g/hr and recovering in storage tank 409. The liquid extracted from the line 65 was a solution containing about 99.8% by weight of 4,4'-methylenebis(cyclohexylisocyanate), and the yield based on 4,4'-methylenebis(cyclohexylamine) was about 70%.

Step (14-4): Recovery of Aromatic Hydroxy Compound

The same method as step (13-4) of Example 13 was carried out with the exception of using the liquid phase component recovered in step (14-3) instead of the liquid phase component recovered in storage tank 407 in step (13-3), and a liquid containing about 99% by weight of bisphenol A was recovered from line 80 at a rate of about 433 g/hr.

Example 15

Step (15-1): Preparation of Mixture of Aromatic Polycarbonate and Aromatic Hydroxy Compound A mixture was prepared by carrying out the same method as step (1-1) of Example 1 with the exception of using 28.3 kg of 4-dodecylphenol (Aldrich Corp., USA) instead of 4-t-octylphenol, and using 10.4 kg of bisphenol A polycarbonate.

Step (15-2): Production of Carbamic Acid Ester

The same method as step (1-2) of Example 1 was carried out with the exception of supplying the mixture prepared in step (15-1) at 9.67 kg/hr instead of the mixture produced in step (1-1) and supplying 2,4-toluenediamine (Aldrich Corp., USA) at 0.37 kg/hr to the reactor 202.

As a result of analyzing the solution following the reaction by gas chromatography, 2,4-toluenediamine was not detected.

Step (15-3): Production of Isocyanate by Thermal Decomposition of Carbamic Acid Ester The same method as step (1-3) of Example 1 was carried out with the exception of supplying the mixture recovered in step (15-2) instead of the mixture recovered in step (1-2) to the thin film distillation apparatus 301 at 160° C. and at a rate of 1.75 kg/hr, condensing gas distilled from the top of the continuous multistage distillation column 312 in condenser 308 via a line 34, continuously extracting from a line 35 at a rate of about 73 g/hr and recovering in storage tank 309. The liquid extracted from the line 35 was a solution containing about 99.8% by weight of 2,4-tolylenediisocyanate, and the yield based on 2,4-toluenediamine was about 79%.

Step (15-4): Recovery of Aromatic Hydroxy Compound

The same method as step (1-4) of Example 1 was carried out with the exception of using the liquid phase component recovered in step (15-3) instead of the liquid phase component recovered in storage tank 307 in step (1-3), and a solution containing about 99% by weight of bisphenol A was recovered from line 50 at a rate of about 380 g/hr.

Example 16

Step (16-1): Preparation of Mixture of Aromatic Polycarbonate and Aromatic Hydroxy Compound A mixture was prepared by carrying out the same method as step (1-1) of Example 1 with the exception of using 29.5 kg of 2,4-di-t-amylphenol instead of 4-t-octylphenol, and using 12.1 kg of bisphenol A polycarbonate.

Step (16-2): Production of Carbamic Acid Ester

The same method as step (1-2) of Example 1 was carried out with the exception of supplying the mixture prepared in step (16-1) at 10.4 kg/hr instead of the mixture produced in step (1-1) and supplying 2,4-toluenediamine at 0.43 kg/hr to the reactor 202. As a result of analyzing the solution following the reaction by gas chromatography, 2,4-toluenediamine was not detected.

Step (16-3): Production of Isocyanate by Thermal Decomposition of Carbamic Acid Ester The same method as step (1-3) of Example 1 was carried out with the exception of supplying the mixture recovered in step (16-2) instead of the mixture recovered in step (1-2) to the thin film distillation apparatus 301 at 160° C. and at a rate of 1.97 kg/hr, condensing gas distilled from the top of the continuous multistage distillation column 312 in condenser 308 via a line 34, continuously extracting from a line 35 at a rate of about 86 g/hr and recovering in storage tank 309. The liquid extracted from the line 35 was a solution containing about 99.8% by weight of 2,4-tolylenediisocyanate, and the yield based on 2,4-toluenediamine was about 78%.

Step (16-4): Recovery of Aromatic Hydroxy Compound

The same method as step (1-4) of Example 1 was carried out with the exception of using the liquid phase component recovered in step (16-3) instead of the liquid phase component recovered in storage tank 307 in step (1-3), and a solution containing about 99% by weight of bisphenol A was recovered from line 50 at a rate of about 460 g/hr.

Example 17

Step (17-1): Preparation of Mixture of Aromatic Polycarbonate and Aromatic Hydroxy Compound A mixture was prepared by carrying out the same method as step (1-1) of Example 1 with the exception of using 24.4 kg of 2-phenylphenol (Wako Pure Chemical Industries, Ltd., Japan) instead of 4-t-octylphenol, and using 12.9 kg of bisphenol A polycarbonate.

Step (17-2): Production of Carbamic Acid Ester

The same method as step (1-2) of Example 1 was carried out with the exception of supplying the mixture prepared in step (17-1) at 9.35 kg/hr instead of the mixture produced in step (1-1) and supplying 2,4-toluenediamine at 0.34 kg/hr to the reactor 202.

As a result of analyzing the solution following the reaction by gas chromatography, 2,4-toluenediamine was not detected.

Step (17-3): Production of Isocyanate by Thermal Decomposition of Carbamic Acid Ester The same method as step (1-3) of Example 1 was carried out with the exception of supplying the mixture recovered in step (17-2) instead of the mixture recovered in step (1-2) to the thin film distillation apparatus 301 at 250° C. and at a rate of 2.12 kg/hr, condensing gas distilled from the top of the continuous multistage distillation column 312 in condenser 308 via a line 34, continuously extracting from a line 35 at a rate of about 82 g/hr and recovering in storage tank 309. The liquid extracted from the line 35 was a solution containing about 99.8% by weight of 2,4-tolylenediisocyanate, and the yield based on 2,4-toluenediamine was about 76%.

Step (17-4): Recovery of Aromatic Hydroxy Compound

The same method as step (1-4) of Example 1 was carried out with the exception of using the liquid phase component recovered in step (17-3) instead of the liquid phase component recovered in storage tank 307 in step (1-3), and a solution containing about 99% by weight of bisphenol A was recovered from a line 50 at the rate of about 440 g/hr.

Example 18

Step (18-1): Preparation of Mixture of Aromatic Polycarbonate and Aromatic Hydroxy Compound A mixture was prepared by carrying out the same method as step (1-1) of Example 1 with the exception of using 24.4 kg of 4-nonylphenol instead of 4-t-octylphenol, and using 9.68 kg of bisphenol A polycarbonate.

Step (18-2): Production of Carbamic Acid Ester

The same method as step (1-2) of Example 1 was carried out with the exception of supplying the mixture prepared in step (18-1) at 8.53 kg/hr instead of the mixture produced in step (1-1) and supplying 4,4'-methylenedianiline at 0.59 kg/hr to the reactor 202.

As a result of analyzing the solution following the reaction by gas chromatography, 4,4'-methylenedianiline was not detected.

Step (18-3): Production of Isocyanate by Thermal Decomposition of Carbamic Acid Ester The same method as step (13-3) of Example 13 was carried out with the exception of supplying the mixture recovered in step (18-2) instead of the mixture recovered in step (13-2) to the thin film distillation apparatus 401 at 180° C. and at a rate of 2.10 kg/hr, condensing gas distilled from the top of the continuous multistage distillation column 412 in condenser 408 via a line 64, continuously extracting from a line 65 at a rate of about 107 g/hr and recovering in storage tank 409. The liquid extracted from the line 65 was a solution containing about 99.8% by weight of 4,4'-diphenylmethane diisocyanate, and the yield based on 4,4'-methylenedianiline was about 63%.

Step (18-4): Recovery of Aromatic Hydroxy Compound

The same method as step (13-4) of Example 13 was carried out with the exception of using the liquid phase component recovered in step (18-3) instead of the liquid phase component recovered in storage tank 407 in step (13-3), and a solution containing about 99% by weight of bisphenol A was recovered from a line 80 at a rate of about 410 g/hr.

Example 19

Step (19-1): Preparation of Mixture of Aromatic Polycarbonate and Aromatic Hydroxy Compound A mixture was prepared by carrying out the same method as step (1-1) of Example 1 with the exception of using 25.3 kg of 2,4-di-t-amylphenol instead of 4-t-octylphenol, and using 10.4 kg of bisphenol A polycarbonate.

Step (19-2): Production of Carbamic Acid Ester

The same method as step (1-2) of Example 1 was carried out with the exception of supplying the mixture prepared in step (19-1) at 8.92 kg/hr instead of the mixture produced in step (1-1) and supplying 4,4'-methylenedianiline at 0.59 kg/hr to the reactor 202.

As a result of analyzing the solution following the reaction by gas chromatography, 4,4'-methylenedianiline was not detected.

Step (19-3): Production of Isocyanate by Thermal Decomposition of Carbamic Acid Ester The same method as step (13-3) of Example 13 was carried out with the exception of supplying the mixture recovered in step (19-2) instead of the mixture recovered in step (13-2) to the thin film distillation apparatus 401 at 180° C. and at a rate of 1.98 kg/hr, condensing gas distilled from the top of the continuous multistage distillation column 412 in condenser 408 via a line 64, continuously extracting from a line 65 at a rate of about 104 g/hr and recovering in storage tank 409. The liquid extracted from the line 65 was a solution containing about 99.8% by weight of 4,4'-diphenylmethane diisocyanate, and the yield based on 4,4'-methylenedianiline was about 66%.

Step (19-4): Recovery of Aromatic Hydroxy Compound

The same method as step (13-4) of Example 13 was carried out with the exception of using the liquid phase component recovered in step (19-3) instead of the liquid phase component recovered in storage tank 407 in step (13-3), and a solution containing about 99% by weight of bisphenol A was recovered from a line 80 at a rate of about 397 g/hr.

Example 20

Step (20-1): Preparation of Mixture of Aromatic Polycarbonate and Aromatic Hydroxy Compound A mixture was prepared by carrying out the same method as step (1-1) of Example 1 with the exception of using 29.5 kg of 4-t-octylphenol and 11.8 kg of bisphenol A polycarbonate.

Step (20-2): Production of Carbamic Acid Ester

The same method as step (1-2) of Example 1 was carried out with the exception of supplying the mixture prepared in step (20-1) at 10.3 kg/hr instead of the mixture produced in step (1-1) and supplying 4,4'-methylenedianiline at 0.62 kg/hr instead of hexamethylene diamine to the reactor 202.

As a result of analyzing the solution following the reaction by gas chromatography, 4,4'-methylenedianiline was not detected.

Step (20-3): Production of Isocyanate by Thermal Decomposition of Carbamic Acid Ester The reaction was carried out using an apparatus like that shown in FIG. 5.

A thin film distillation apparatus 501 (Kobelco Eco-Solutions Co., Ltd., Japan) having a heat-conducting surface area of 0.1 m² was heated to 200° C., and the internal pressure was set to about 13 kPa. The mixture recovered in storage tank 203 in step (20-2) was heated to 180° C. and supplied to the top of the thin film distillation apparatus 501 at a rate of about 2200 g/hr via a line A1. A portion of a liquid phase component extracted from the bottom of the thin film distillation apparatus 501 was circulated to the top of the thin film distillation apparatus 501 via a line A3 and a line A4. On the other hand, a gaseous phase component was extracted from a line A2. In addition, the liquid phase component not circulated to the thin film distillation apparatus 501 was extracted into a storage tank 507.

The gaseous phase component extracted via the line A2 from the thin film distillation apparatus 501 was continuously fed to the intermediate stage of a continuous multistage distillation column 502 having an inner diameter of about 5 cm and a column length of 2 m and packed with Dixon packing (diameter: 6 mm) to carry out distillative separation of the gaseous phase component. The amount of heat required for distillative separation was supplied by circulating the liquid in the bottom of the column through a line A7 and a reboiler 505. The liquid temperature in the bottom of the continuous multistage distillation column 502 was 230° C., and the pressure at the top of the column was about 1.3 kPa. A gaseous phase component of the gas distilled from the top of the continuous multistage distillation column 502 was extracted via a line A5, and after condensing in a condenser 503, was continuously extracted into a storage tank 504 via a line A6. The solution obtained in storage tank 504 contained about 99% by weight of 4-t-octylphenol.

The liquid phase component extracted into storage tank 507 was supplied to a continuous multistage distillation column 508 via a line A10. The continuous multistage distillation column 508 was a continuous multistage distillation column having an inner diameter of about 5 cm and a column length of 2 m and packed with Dixon packing (diameter: 6 mm), and distillative separation of the liquid phase component supplied from storage tank 507 was carried out with this distillation column. The amount of heat required for distillative separation was supplied by circulating liquid in the bottom of the column through a line A13 and a reboiler 511. The liquid temperature in the bottom of the multistage continuous distillation column 508 was 210° C., and the pressure at the top of the column was about 0.5 kPa. A liquid phase component was extracted from a line A15 of the continuous multistage distillation column 508 provided at a location lower than a line A10 and supplied to a continuous multistage distillation column 513. The continuous multistage distillation column 513 was a continuous multistage distillation column having an inner diameter of about 5 cm and column length of 2 m and packed with Dixon packing (diameter: 6 mm), and distillative separation of the liquid phase component extracted from the continuous multistage distillation column 508 was carried out with this distillation column. Gas distilled from the top of the continuous multistage distillation column 513 was condensed in a condenser 514 via a line A17 and continuously extracted from a line A18 at a rate of about 81 g/hr and recovered in a storage tank 515.

Liquid extracted from the line A18 was a solution containing about 99% by weight of 4,4'-diphenylmethane diisocyanate, and the yield based on 4,4'-methylenedianiline was about 52%.

Step (20-4) Recovery of Aromatic Hydroxy Compound

Figure 6:
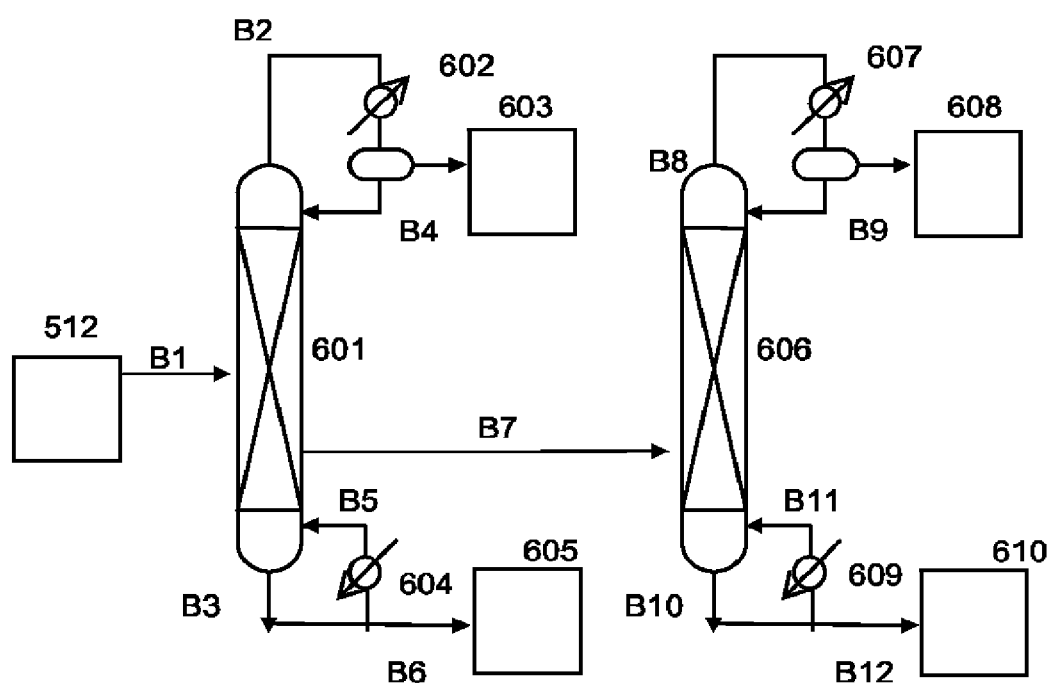
FIG. 6 illustrates a conceptual drawing showing an apparatus for producing an isocyanate and aromatic hydroxy compound used in an example of the present invention.

An apparatus was used like that shown in FIG. 6.

The liquid phase component recovered in storage tank 512 in step (20-3) was continuously fed through a line B1 to an intermediate stage of a continuous multistage distillation column 601 having an inner diameter of about 5 cm and a column length of 2 m and packed with Dixon packing (diameter: 6 mm) to carry out separative distillation of the liquid phase component. The amount of heat required for distillative separation was supplied by circulating a portion of the liquid in the bottom of the column through a line B3 and a reboiler 604. The liquid temperature of the liquid in the bottom of continuous multistage distillation column 601 was 200° C. and the pressure at the top of column was about 5.8 kPa. A liquid phase component was extracted from a line B7 of the continuous multistage distillation column 601 provided at a location lower than the line B1, and supplied to a continuous multistage distillation column 606 from line B7.

The liquid phase component supplied to the continuous multistage distillation column 606 was separated by distillation with this distillation column. The liquid temperature of the liquid in the bottom of continuous multistage distillation column 606 was 240° C. and the pressure at the top of column was 0.5 kPa. Gas distilled from the top of continuous multistage distillation column 606 was condensed in a condenser 607 via a line B8 and continuously extracted into a storage tank 608 via a line B9 at a rate of about 310 g/hr. Liquid extracted from line B9 was a solution containing about 99% by weight of bisphenol A.

Example 21

Step (21-1): Preparation of Mixture of Aromatic Polycarbonate and Methylene Chloride Solution A mixture was prepared by carrying out the same method as step (1-1) of Example 1 with the exception of using 9.36 kg of methylene chloride (Wako Pure Chemical Industries, Ltd., Japan) instead of 4-t-octylphenol, using 7.26 kg of bisphenol A polycarbonate, and holding at 30° C. in the reactor 102.

Step (21-2): Production of Carbamic Acid Ester

The reactor 202 was maintained at 35° C., and the same method as step (1-2) of Example 1 was carried out with the exception of supplying the mixture prepared in step (21-1) at 4.15 kg/hr instead of the mixture produced in step (1-1) and supplying hexamethylene diamine at 0.24 kg/hr to the reactor 202.

As a result of analyzing the solution following the reaction by gas chromatography, hexamethylene diamine was not detected.

Step (21-3): Production of Isocyanate by Thermal Decomposition of Carbamic Acid Ester The same method as step (1-3) of Example 1 was carried out with the exception of supplying the mixture recovered in step (21-2) instead of the mixture recovered in step (1-2) to the thin film distillation apparatus 301 at 35° C. and at a rate of 1660 g/hr, condensing gas distilled from the top of the continuous multistage distillation column 312 in condenser 308 via a line 34, continuously extracting from a line 35 at a rate of about 111 g/hr and recovering in storage tank 309. The liquid extracted from the line 35 was a solution containing about 99.8% by weight of hexamethylene diisocyanate, and the yield based on hexamethylene diamine was about 82%.

Step (21-4): Recovery of Aromatic Hydroxy Compound

An apparatus was used like that shown in FIG. 4.

The same method as step (1-4) of Example 1 was carried out with the exception of using the liquid phase component recovered in step (21-3) instead of the liquid phase component recovered in storage tank 307 in step (1-3), and a liquid containing about 99% by weight of bisphenol A was recovered from a line 50 at a rate of about 358 g/hr.

Example 22

Step (22-1): Preparation of Mixture of Aromatic Polycarbonate and Aromatic Hydroxy Compound A mixture was prepared by carrying out the same method as step (1-1) of Example 1 with the exception of using 14.0 kg of 4-t-octylphenol and using 10.3 kg of bisphenol A polycarbonate.

Step (22-2): Production of Carbamic Acid Ester

Figure 7:
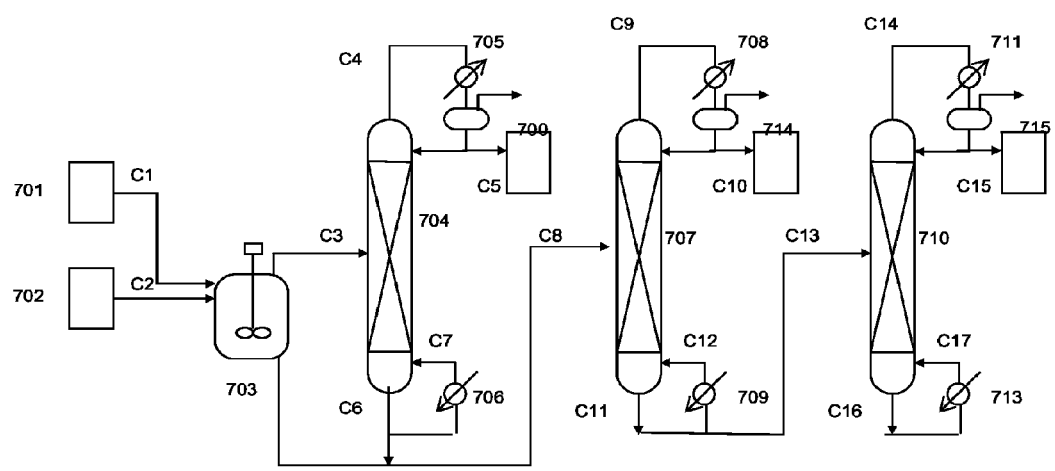
FIG. 7 illustrates a conceptual drawing showing an apparatus for producing an isocyanate and aromatic hydroxy compound used in an example of the present invention.

A reaction was carried out using an apparatus like that shown in FIG. 7.

The mixture prepared in step (22-1) was supplied from a storage tank 701 to a baffled SUS reactor 703 at a rate of about 6.09 kg/hr via a line C1 with a line C3 closed, and hexamethylene diamine was supplied from a storage tank 702 to the reactor 703 via a line C2 at a rate of about 0.37 kg/hr.

As a result of analyzing the solution following the reaction by liquid chromatography, hexamethylene diamine was not detected.

Step (22-3): Production of Isocyanate by Thermal Decomposition of Carbamic Acid Ester Subsequently, a reaction was carried out using an apparatus like that shown in FIG. 7.

The SUS reactor 703 was heated to 220° C. and the pressure inside the reactor was reduced to 1.3 kPa. A gaseous phase component was extracted from a line C3, and the gaseous phase component was continuously fed to an intermediate stage of a continuous multistage distillation column 704 having an inner diameter of about 5 cm and a column length of 2 m and packed with Dixon packing (diameter: 6 mm) to carry out distillative separation. The amount of heat required for distillative separation was supplied by circulating the liquid in the bottom of the column via a line C6 and a reboiler 706. The liquid temperature at the bottom of the continuous multistage distillation column 704 was 150° C. and the pressure at the top of the column was about 15 kPa. Gas distilled from the top of the continuous multistage distillation column 704 was condensed in a condenser 705 via a line C4 and continuously extracted from a line C5 at a rate of about 363 g/hr. The solution extracted from the line C5 was a solution containing about 99% by weight of hexamethylene diisocyanate, and the yield based on hexamethylene diamine was about 67%.

Step (22-4): Recovery of Aromatic Hydroxy Compound

The liquid phase component in step (22-3) was supplied from the bottom of the reactor 703 to a continuous multistage distillation column 707 via a line C18. The distillation column 707 was a continuous multistage distillation column having an inner diameter of about 5 cm and a column length of 2 m and packed with Dixon packing (diameter: 6 mm), and distillative separation of the liquid phase component was carried out with this distillation column. The amount of heat required for distillative separation was supplied by circulating the liquid in the bottom of the column via a line C11 and a reboiler 709. The liquid temperature at the bottom of the continuous multistage distillation column 707 was 200° C. and the pressure at the top of the column was about 1.5 kPa. Gas distilled from the top of the continuous multistage distillation column 707 was condensed in a condenser 708 via a line C9 and continuously extracted into a storage tank 714 via a line C10. The compound recovered in the storage tank 714 was 4-t-octylphenol. On the other hand, a portion of the liquid phase component of the continuous multistage distillation column 707 was supplied to a continuous multistage distillation column 710 from a line C11 via a line C13. The distillation column 710 was a continuous multistage distillation column having an inner diameter of about 5 cm and a column length of 2 m and packed with Dixon packing (diameter: 6 mm), and distillative separation of the liquid phase component was carried out with this distillation column. The amount of heat required for distillative separation was supplied by circulating liquid in the bottom of the column via a line C16 and reboiler 713. The liquid temperature at the bottom of the continuous multistage distillation column 710 was 250° C. and the pressure at the top of the column was about 0.5 kPa. Gas distilled from the top of the continuous multistage distillation column 710 was condensed in a condenser 711 via a line C14, and continuously extracted into a storage tank 715 via a line C15. The compound recovered in the storage tank 715 was bisphenol A.

Example 23

Figure 8:
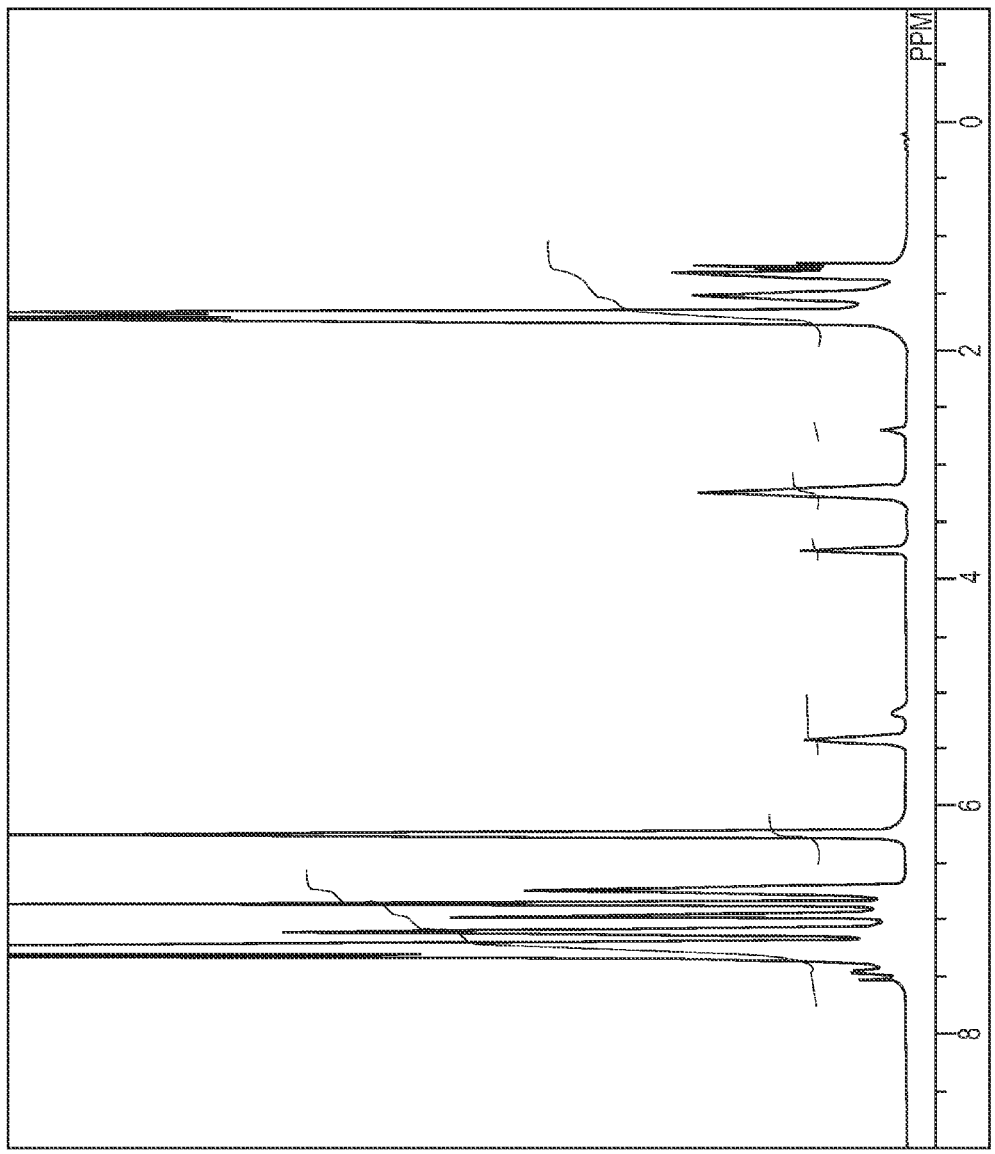
FIG. 8 is a drawing of NMR analysis ($^1$H-NMR) of a mixture containing a carbamic acid ester compound indicated in Example 23 of the present invention.
Figure 9:
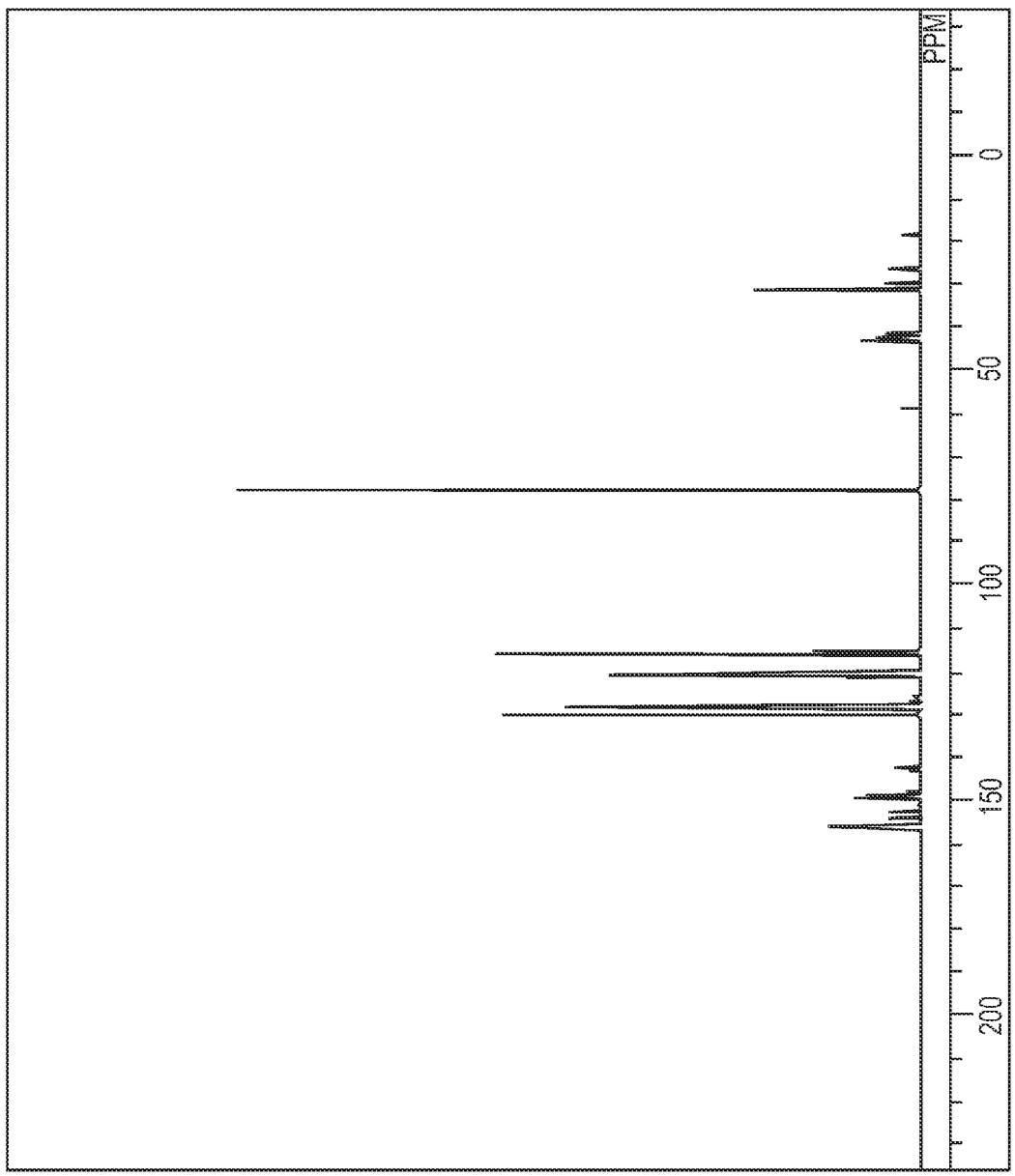
FIG. 9 is a drawing of NMR analysis ($^{13}$C-NMR) of a mixture containing a carbamic acid ester compound indicated in Example 23 of the present invention.

Step (23-1): Production of Carbamic Acid Ester Compound 134.2 g of poly(bisphenol A carbonate) (Aldrich Corp., USA, weight average molecular weight: 64,000 (catalog value)) and 280 g of methylene chloride were placed in a reaction vessel in the form of a 1000 mL volumetric four-mouth flask to which was attached a Dimroth condenser, dropping funnel and three-way valve followed by stirring to prepare a solution. A mixture of 11.6 g (0.10 mol) of hexamethylene diamine and 30 g of methylene chloride were placed in the dropping funnel and the inside of the reaction vessel was replaced with nitrogen. The reaction vessel was immersed in a water bath adjusted to 10° C. and a mixture of hexamethylene diamine and chloroform were dropped into the reaction vessel over the course of about 1 hour. Following completion of dropping, the mixture was stirred for about 4 hours. When a portion of the resulting mixed solution was sampled and subjected to $^1$H— and $^{13}$C-NMR analyses, the product was confirmed to be a carbamic acid ester compound as shown FIG. 8 and FIG. 9.

Step (23-2): Production of Isocyanate by Thermal Decomposition of Carbamic Acid Ester A vacuum pump and a vacuum controller were attached to a molecular distillation apparatus (Model MS-300, Sibata Scientific Technology Ltd., Japan) having a jacketed heating unit using oil circulation, and the purge line of the vacuum controller was connected to a nitrogen gas line. The inside of the molecular distillation apparatus was replaced with nitrogen and the heating unit was heated to 200° C. A solution was then prepared by mixing 405 g of the mixture containing carbamic acid ester compound obtained in Example 1 and 120 g of benzyl butyl phthalate (guaranteed reagent, Wako Pure Chemical Industries, Ltd., Japan). The inside of the molecular distillation apparatus was reduced to 1.3 kPa, and the slurry was charged into the molecular distillation apparatus at a rate of about 5 g/min while rotating the wiper of the molecular distillation apparatus at about 300 rpm to thermally decompose the polycarbamic acid ester compound. 12.1 g of a thermal decomposition product were obtained in the sample receiver. As a result of analysis, chloroform was recovered in the low boiling point trap, a mixture containing bisphenol A and benzyl butyl phthalate were recovered in the feedback receiver, and the liquid obtained in the sample receiver contained about 95% hexamethylene diisocyanate, and the yield based on hexamethylene diamine was 70%.

Step (23-3): Recovery of Aromatic Hydroxy Compound

The mixture containing bisphenol A and benzyl butyl phthalate obtained in the feedback receiver in step (23-2) was heated to 280° C. and charged into a molecular distillation apparatus (Model MS-300, Shibata Scientific Technology Ltd., Japan) at a rate of about 10 g/min after reducing the pressure inside the apparatus to 0.13 kPa followed by distilling off the benzyl butyl phthalate. About 200 mL of toluene were then added to the resulting liquid phase component while heating, and after filtering out the precipitating component, the toluene solution was allowed to stand undisturbed until it reached room temperature. The precipitated crystals were filtered out, and when a portion of the crystals were sampled and subjected to $^1$H— and $^{13}$C-NMR analysis, the crystals were found to contain about 99% by weight of bisphenol A.

Comparative Example 1

Step (A-1): Preparation of Mixture of Aromatic Polycarbonate and Aromatic Hydroxy Compound A mixture was prepared using an apparatus like that shown in FIG. 1.

11.1 kg of molten 4-t-octylphenol were transferred from storage tank 101 to storage tank 102 heated to 250° C. after replacing the inside of the tank with nitrogen with a line 12 closed. 5.19 kg of bisphenol A polycarbonate (Aldrich Corp. USA, weight average molecular weight: 65,000) were charged from a hopper 100 into the reactor 102 and stirred. After confirming that the bisphenol A polycarbonate had dissolved, line 12 was opened and the mixture was transferred to storage tank 103.

Step (A-2): Reaction of Aromatic Polycarbonate and Amine Compound

A reaction was carried out using an apparatus like that shown in FIG. 2.

The mixture produced in step (A-1) was supplied from storage tank 103 via a line 21 to baffled SUS reactor 202 held at about 150° after replacing the inside of the reactor with nitrogen at a rate of 4.08 kg/hr with a line 23 closed. Tributylamine (Aldrich Corp., USA) was supplied from storage tank 201 via a line 22 to the reactor 202 at a rate of about 0.33 kg/hr. One hour after the start of addition, the line 23 was opened and the reaction liquid was transferred to storage tank 203 via the line 23.

Step (A-3): Recovery of Amine Compound

An apparatus was used like that shown in FIG. 3.

Thin film distillation apparatus 301 (Kobelco Eco-Solutions Co., Ltd., Japan) having a heat-conducting surface area of 0.1 m² was heated to 220° C., and an internal pressure was set to about 13 kPa. The mixture recovered in storage tank 203 in step (A-2) was heated to 150° C. and supplied to the top of the thin film distillation apparatus 301 at a rate of about 1500 g/hr via a line 31. A liquid phase component was extracted from a line 32 from the bottom of the thin film distillation apparatus 301 and circulated to the top of the thin film distillation apparatus 301 via a line 36. The liquid phase component not circulated to the thin film distillation apparatus 301 was recovered in storage tank 307. A gaseous phase component was extracted from a line 33 from the thin film distillation apparatus 301 and supplied to continuous multistage distillation column 302.

The gaseous phase component extracted via the line 33 from the thin film distillation apparatus 301 was continuously fed to an intermediate stage of the continuous multistage distillation column 302 having an inner diameter of about 5 cm and a column length of 2 m and packed with Dixon packing (diameter: 6 mm) to carry out distillative separation of the gaseous phase component. The amount of heat required for distillative separation was supplied by circulating the liquid in the bottom of the column through a line 39 and a reboiler 305. The liquid temperature in the bottom of the continuous multistage distillation column 302 was 150° C., and the pressure at the top of the column was about 2.6 kPa. Gas distilled from the top of the continuous multistage distillation column 302 was condensed in a condenser 303 via a line 37, continuously extracted from a line 38 and recovered in storage tank 304. The liquid extracted from the line 38 was tributylamine.

Step (A-4) Recovery of Aromatic Hydroxy Compound

An apparatus was used like that shown in FIG. 3.

The liquid phase component recovered in storage tank 307 in step (A-3) was continuously fed to an intermediate stage of a continuous multistage distillation column 313 having an inner diameter of about 5 cm and a column length of 2 m and packed with Dixon packing (diameter: 6 mm) to carry out separative distillation of the liquid phase component. The amount of heat required for distillative separation was supplied by circulating a portion of the liquid in the bottom of the column through a line 45 and a reboiler 315. The liquid temperature of the liquid in the bottom of continuous multistage distillation column 315 was 180° C. and the pressure at the top of column was about 1.3 kPa. Gas distilled from the top of continuous multistage distillation column 315 was condensed in a condenser 314 via a line 44 and continuously extracted into a storage tank 316 via a line 46.

A liquid phase component was extracted from a line 48 of the continuous multistage distillation column 313 provided at a location lower than a line 43 and supplied to continuous multistage distillation column 318.

The liquid phase component supplied to the continuous multistage distillation column 318 via the line 48 was separated by distillation in that distillation column. The liquid temperature at the bottom of the continuous multistage distillation column 318 was 240° C. and the pressure at the top of the column was 0.5 kPa. Gas distilled from the top of the distillation column 318 was condensed in a condenser 319 via a line 49 and continuously extracted at a rate of about 50 g/hr into storage tank 309 via a line 50.

Liquid extracted from the line 46 was a solution containing about 99% by weight of 4-t-octylphenol. In addition, liquid extracted from the line 50 was a liquid containing about 99% by weight of bisphenol A.

The present application is based on Japanese patent applications filed on Nov. 19, 2007 (Japanese Patent Application Nos. 2007-299497, 2007-299504 and 2007-299703), the contents of which are incorporated herein by reference.

INDUSTRIAL APPLICABILITY

A carbamic acid ester obtained with the process according to the present embodiment is preferable as a raw material for producing isocyanate without using extremely toxic phosgene, and isocyanate obtained with the process according to the present embodiment can be preferably used as a production raw material of polyurethane foam, paints, adhesives and the like. In addition, divalent aromatic hydroxy compounds obtained with the process according to the present embodiment can be preferably used as production raw materials of aromatic polycarbonates. The process according to the present embodiment also demonstrates the aspect of chemical recycling of aromatic polycarbonates. On the basis of the above, the process according to the present invention is extremely industrially useful and has high commercial value.

We claim:

1. A carbamic acid ester compound represented by the following formula (1):

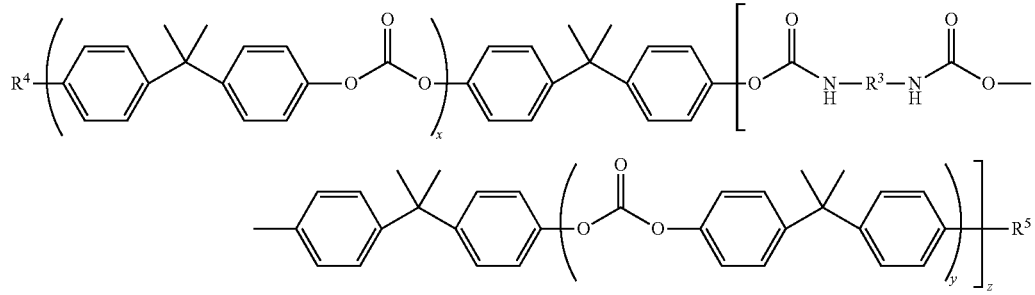

(wherein $R^3$ represents a group selected from the group consisting of aliphatic groups having 1 to 20 carbon atoms, each of $R^4$ and $R^5$ independently represents a substituent selected from the group represented by the following formula (2):

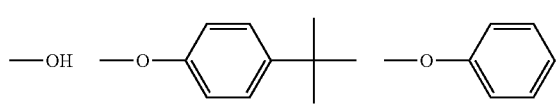

and x represents an integer of 0 or more, and each of y and z independently represents an integer of 1 or more).

2. The carbamic acid ester compound according to claim 1, wherein the $R^3$ represents the aliphatic group, and $R^4$ and $R^5$ together contain —OH and

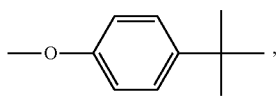

or —OH and

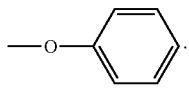

3. The carbamic acid ester compound according to claim 1, wherein the $R^3$ represents the aliphatic group, and $R^4$ and $R^5$ contain —OH and

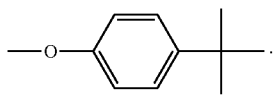

4. The carbamic acid ester compound according to claim 1, wherein the $R^3$ represents the aliphatic group, and $R^4$ and $R^5$ contain —OH and

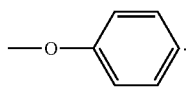

5. The carbamic acid ester compound according to claim 1, wherein the $R^3$ represents —$(CH)_6$—.

6. A carbamic acid ester compound composition comprising:
(i) the carbamic acid ester compound of claim 2,
(ii) a second carbamic acid ester compound represented the following formula (1):

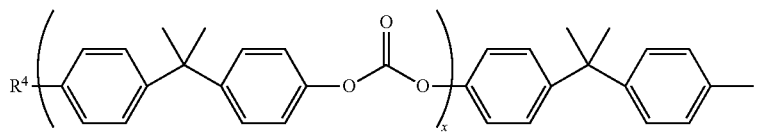 (1)

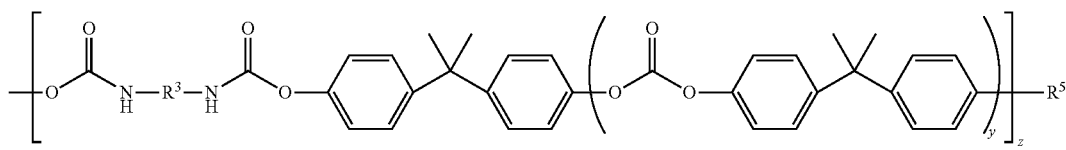

(wherein $R^3$ represents an aliphatic group having 1 to 20 carbon atoms,
each of $R^4$ and $R^5$ represents —OH, and
x represents an integer of 0 or more, and each of y and z independently represents an integer of 1 or more).

7. A carbamic acid ester compound composition comprising:
(i) the carbamic acid ester compound of claim 2,
(ii) a third carbamic acid ester compound represented the following formula (1):

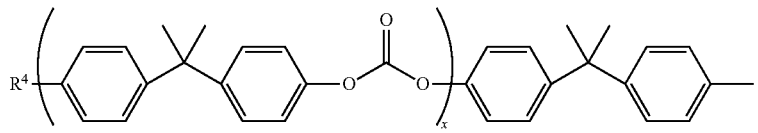 (1)

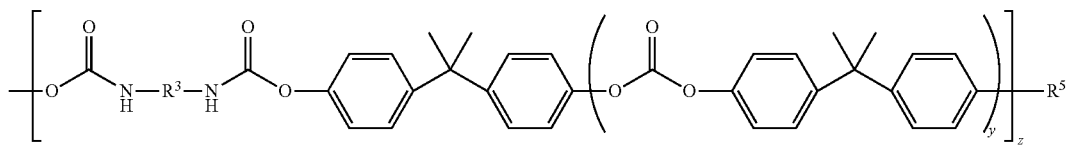

(wherein R³ represents an aliphatic group having 1 to 20 carbon atoms, each of R⁴ and R⁵ represents

, and x represents an integer of 0 or more, and each of y and z independently represents an integer of 1 or more).

8. A carbamic acid ester compound composition comprising:
(i) the carbamic acid ester compound of claim 2,
(ii) a fourth carbamic acid ester compound represented the following formula (1):

each of R⁴ and R⁵ represents

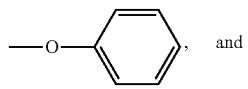, and x represents an integer of 0 or more, and each of y and z independently represents an integer of 1 or more).

9. A carbamic acid ester compound composition comprising:
(i) the carbamic acid ester compound of claim 2,
(ii) a fifth carbamic acid ester compound represented by the following formula (1):

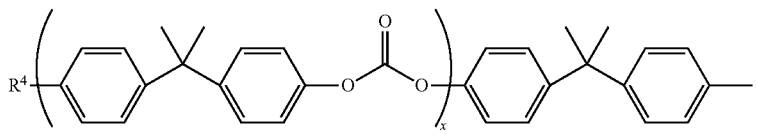 (1)

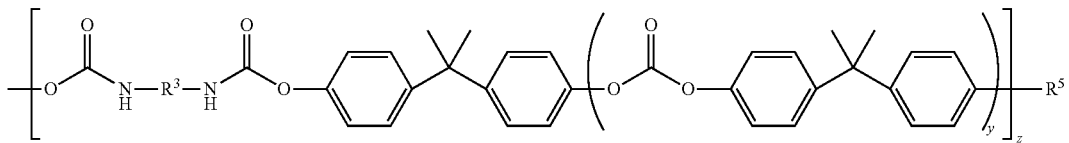

(wherein R³ represents an aliphatic group having 1 to 20 carbon atoms,

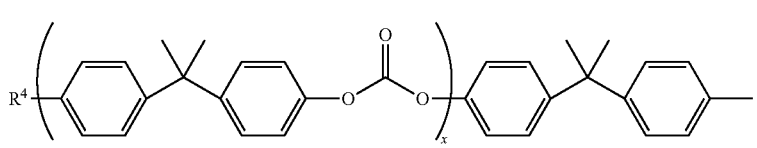 (1)

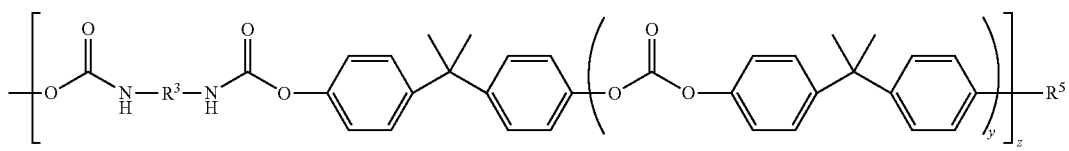

(wherein R³ represents an aliphatic group having 1 to 20 carbon atoms,

R⁴ and R⁵ together contain

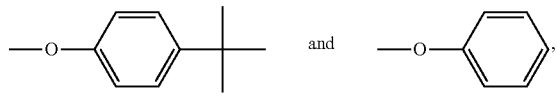 and 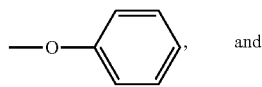, and x represents an integer of 0 or more, and each of y and z independently represents an integer of 1 or more).

10. A carbamic acid ester compound composition comprising:
(i) the carbamic acid ester compound of claim 2,
(ii) a second carbamic acid ester compound represented the following formula (1):

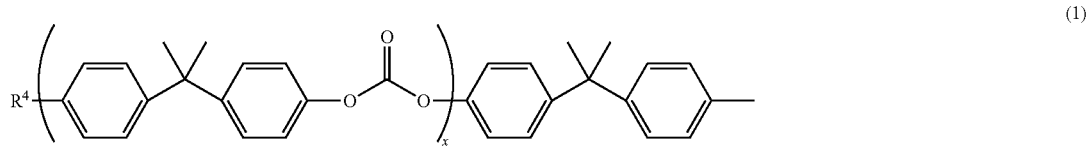

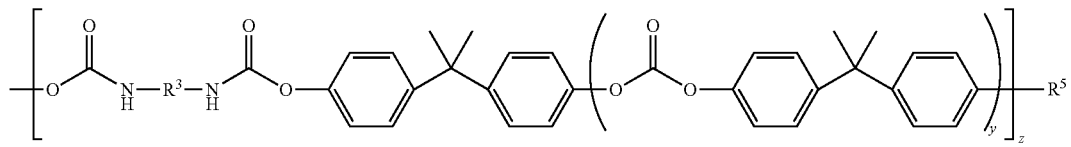

(1)

(wherein R³ represents an aliphatic group having 1 to 20 carbon atoms, each of R⁴ and R⁵ represents —OH, and x represents an integer of 0 or more, and each of y and z independently represents an integer of 1 or more), and (iii) a third carbamic acid ester compound represented by the formula (1)

(wherein R³ represents an aliphatic group having 1 to 20 carbon atoms, each of R⁴ and R⁵ represents

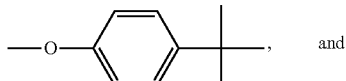, and x represents an integer of 0 or more, and each of y and z independently represents an integer of 1 or more), (iv) a fourth carbamic acid ester compound represented by the formula (1)

(wherein R³ represents an aliphatic group having 1 to 20 carbon atoms, each of R⁴ and R⁵ represents

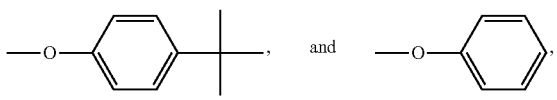

x represents an integer of 0 or more, and each of y and z independently represents an integer of 1 or more)

(v) a fifth carbamic acid ester compound represented by the formula (1)

(wherein R³ represents an aliphatic group having 1 to 20 carbon atoms,

R⁴ and R⁵ together contain

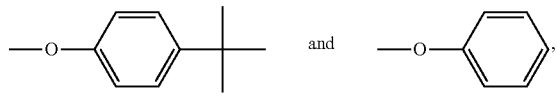, and 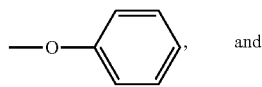, and x represents an integer of 0 or more, and each of y and z independently represents an integer of 1 or more).

11. The carbamic acid ester compound composition according to claim 10, wherein each of the R³ in the formula (1) of the carbamic acid ester compound of claim 2 and the second, third, fourth, and fifth carbamic acid ester compounds represents —(CH)₆—.

* * * * *